(12) United States Patent
Kamiya et al.

(10) Patent No.: US 6,884,355 B2
(45) Date of Patent: Apr. 26, 2005

(54) PROCESS FOR TREATING ORGANIC WASTEWATER AND APPARATUS FOR TREATING THE ORGANIC WASTEWATER

(75) Inventors: Toshiyuki Kamiya, Tokyo (JP); Junji Hirotsuji, Tokyo (JP); Nozomu Yasunaga, Tokyo (JP); Seiji Furukawa, Tokyo (JP); Naoki Nakatsugawa, Tokyo (JP)

(73) Assignee: Mitsubishi Denki Kabushiki Kaisha, Tokyo (JP)

( * ) Notice: Subject to any disclaimer, the term of this patent is extended or adjusted under 35 U.S.C. 154(b) by 0 days.

(21) Appl. No.: 10/453,643

(22) Filed: Jun. 4, 2003

(65) Prior Publication Data

US 2003/0226803 A1 Dec. 11, 2003

(30) Foreign Application Priority Data

Jun. 5, 2002 (JP) ........................................ 2002-164400
Apr. 30, 2003 (JP) ........................................ 2003-125377

(51) Int. Cl.⁷ .............................. C02F 3/30; C02F 1/78; C02F 3/28
(52) U.S. Cl. ..................... 210/631; 210/198.1; 210/205
(58) Field of Search ................................ 210/603, 630, 210/631, 198.1, 205, 206, 252, 259, 906; 435/262, 262.5

(56) References Cited

U.S. PATENT DOCUMENTS

| 4,609,469 A | * | 9/1986 | Keoteklian ................. 210/609 |
| 5,370,801 A | * | 12/1994 | Sorensen et al. ............ 210/742 |
| 6,254,779 B1 | * | 7/2001 | Jeffery et al. ............... 210/620 |
| 6,706,185 B1 | * | 3/2004 | Goel et al. ................. 210/605 |
| 2003/0178364 A1 | * | 9/2003 | Yum et al. ................... 210/623 |

FOREIGN PATENT DOCUMENTS

| JP | 6-269797 | * | 9/1994 |
| JP | 8-10791 A | * | 1/1996 |
| JP | 09-066298 | | 3/1997 |
| JP | 09-206785 | | 8/1997 |
| JP | P2000-246280 | * | 9/2000 |
| JP | P2000-350995 | * | 12/2000 |
| JP | 2001-239298 | | 9/2001 |

OTHER PUBLICATIONS

Jardin et al., "Refixation of phosphates released during Bio–P sludge handling as struvite or aluminium phosphate", *Environmental Technology*, 2001, pp. 1253–1262, vol. 22, Germany.

* cited by examiner

*Primary Examiner*—Fred G. Prince
(74) *Attorney, Agent, or Firm*—Leydig, Voit & Mayer, Ltd.

(57) ABSTRACT

A process for treating organic wastewater which comprises treating organic wastewater with ozone and successively with alkali and introducing said alkali treated organic wastewater into an anaerobic digestion tank for anaerobic digestion. Instead of the ozone and successive alkali treatments, ozone treatment in the presence of hydrogen peroxide or ozone treatment under UV radiation is applicable. Prior to introduction into the anaerobic digestion tank, the treated wastewater may be separated into solids and phosphorus is preferably recovered from the solution. Solubilization of solids in the organic wastewater and transformation of organic substances into methane are greatly enhanced and sludge to be disposed is greatly reduced. Moreover, phosphorus is efficiently eluted out and recovered from solids in the organic wastewater.

14 Claims, 44 Drawing Sheets

PROCESS FOR TREATING ORGANIC WASTEWATER AND APPARATUS FOR TREATING THE ORGANIC WASTEWATER

FIELD OF THE INVENTION

The present invention relates to a process for treating organic wastewater and an apparatus for treating the organic wastewater.

BACKGROUND OF THE INVENTION

As a process to treat a slurry of high concentration organic wastewater such as wastewater, from food manufacturing, organic sludge from sewage processing, and excrement from animate beings, anaerobic digestion is known in which methane that is reusable as an energy source is produced. However, anaerobic digestion is time-consuming and, moreover, about 50% of solid matter in influent wastewater is barely solubilized and the yield of methane is as low as about 50%.

As a method to increase solubility of solid matter in organic wastewater and improve transformation into methane gas, Japanese Unexamined Patent Publication No. 206785/1997 discloses a process wherein digested sludge is drawn out from an anaerobic digestion tank, denatured with ozone or high-voltage pulse discharge and, then, returned to the anaerobic digestion tank. Japanese Unexamined Patent Publication No. 179285/2001 discloses another process in which microorganisms producing lytic enzyme are employed. In this process, digested sludge is drawn out from an anaerobic digestion tank, subjected to solid-liquid separation and, then, thickened. Thereafter, the thickened digester sludge is treated with microorganisms producing lytic enzyme, treated with ozone under alkaline conditions and, then, returned to the anaerobic digestion tank.

Also since it has recently been found that the amount of deposited phosphorus is not enough for future demand, recycle of phosphorus is considered most important. Since organic wastewater, especially organic sludge from wastewater treatment, has a higher concentration of phosphorus, an attempt has been made to recover phosphorus from organic sludge. For example, "Renovation of polluted environment utilizing bio-remediation technology; biotechnology for recycling phosphorus", Journal of Society of Environmental Science, Japan, Vol. 12, No. 4, pp. 433–441 (1999), discloses a process wherein activated sludge from a wastewater treatment plant is treated with heat at 70 to 90° C. for a maximum of 120 minutes to elute out phosphorus in the sludge into liquid phase.

Sludge in the anaerobic digestion tank forms sludge flocs where microorganisms and/or organic polymer are highly congested. In the above conventional process, however, ozone treatment is directly applied to solid matter in digested sludge so ozone hardly permeates into the sludge flocs and acts only on the surface of solids in the sludge. As a result, hardly soluble substances in the digested sludge are not sufficiently denatured, i.e. not sufficiently converted into easily soluble substances, and improvement in solubility of sludge solids and transformation into methane are not satisfactory.

In the above conventional process, it is possible to disperse the solid matter with ozone in order to treat the hardly soluble substances inside the solid matter with ozone. However, when both dispersion and denaturation are performed with ozone treatment alone, ozone consumption increases. In other words, a large amount of ozone is required in denaturing the hardly soluble substances, i.e. in achieving conversion to easily soluble substances, so the process becomes inefficient and running costs thereof rise.

In the process of Japanese Unexamined Patent Publication No. 179285/2001, meanwhile, sludge is treated with ozone under alkaline conditions in order to produce radicals that are much more active than ozone. Since ozone is easily and rapidly decomposed into radicals under alkaline conditions, such conditions are preferable for producing radicals but the effects of ozone itself are neither obtained nor utilized through the process. In addition, since radicals derived from ozone are extremely active, they quickly react with dissolved contents (i.e. organic substances already dissolved) in the sludge rather than react with solid matter in the sludge. Accordingly, radicals for solubilizing the solid matter in the sludge are wasted and solublization of the solid matter is hardly enhanced under alkaline conditions. If improvement in solubilizing the sludge is sought under such alkaline conditions, a great amount of ozone must be injected.

In the above conventional processes in which ozone is utilized, ozone treatment is only intended to improve solubility of the sludge so neither the effect of ozone treatment to elute out phosphorus in the sludge into the liquid phase, nor a process to recover phosphorus, nor an apparatus for recovering phosphorus, is suggested. In the above conventional process in which phosphorus is recovered from the sludge of wastewater, the sludge is treated with heat to elute phosphorus out into the liquid phase. However, this heat treatment is only for eluting phosphorus out and other effects of this heat treatment, such as improvement in recovery of energy source, is not suggested. Therefore, an efficient process or apparatus, in which energy source and phosphorus resource are simultaneously recovered, is not realized.

Accordingly, the object of the present invention is to provide a process and apparatus in which solubility of solids in organic wastewater, organic sludge or digested sludge is improved, transformation of organic substances into methane is enhanced, and sludge disposal is reduced.

Another object of the present invention is to provide a process and apparatus, in which energy and resource are simultaneously recovered, where phosphorus is eluted out and recovered from solids in organic wastewater, organic sludge or digested sludge while organic substances are transformed into methane.

That is, the object of the present invention is to provide a process and apparatus in which solubility of sludge is efficiently improved with less energy and lower costs, the rate of energy recovery is increased, the amount of disposed sludge is reduced, and phosphorus is eluted out for recovery as a resource.

SUMMARY OF THE INVENTION

The present invention relates to a process for treating organic wastewater by anaerobic digestion, which comprises treating organic wastewater with ozone and successively with alkali and introducing said alkali treated organic wastewater into an anaerobic digestion tank.

The present invention relates to a process for treating organic wastewater by anaerobic digestion, which comprises treating organic wastewater with ozone in the presence of hydrogen peroxide and introducing said ozone treated organic wastewater into an anaerobic digestion tank.

The present invention relates to an apparatus for treating organic wastewater comprising a means for treating organic wastewater with ozone, a means for treating the ozone treated organic wastewater with alkali and an anaerobic digestion tank for anaerobically digesting the alkali treated organic wastewater.

The present invention relates to an apparatus for treating organic wastewater comprising a means for treating organic wastewater with ozone in the presence of hydrogen peroxide and an anaerobic digestion tank for anaerobically digesting the ozone treated organic wastewater.

DETAILED DESCRIPTION

Hereinafter, preferred embodiments of the present invention are described with reference to the accompanying drawings. However, the present invention is not limited thereto.

Embodiment 1

An apparatus according to the present invention and a process of treating organic wastewater with the apparatus is described.

Figure 11:
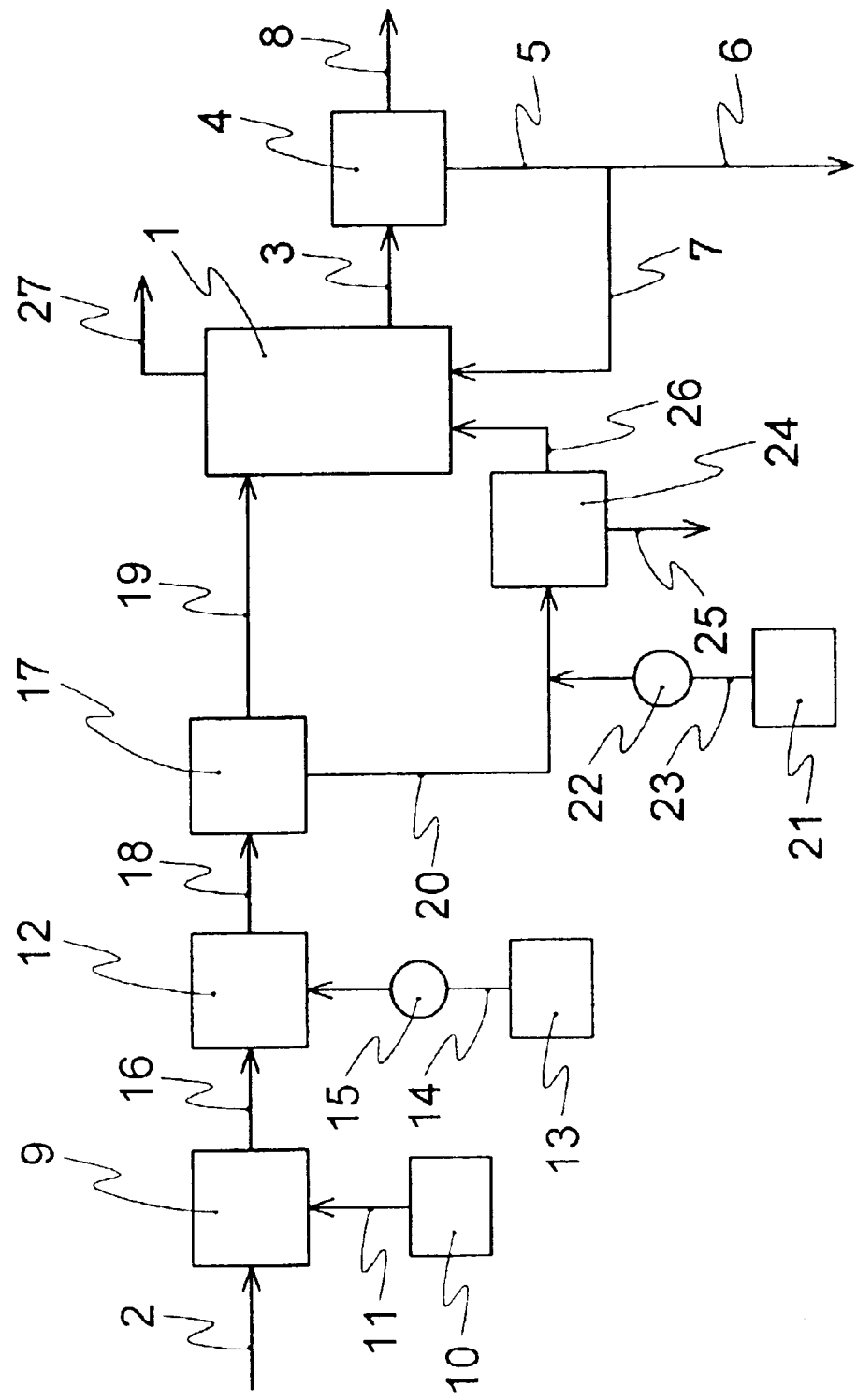
FIG. 11 is a diagram showing an apparatus embodying the present invention and a process flow of treating organic wastewater according to the present invention.

FIG. 11 is a diagram of an apparatus embodying the present invention and shows a process flow of treating organic wastewater with the apparatus.

As shown in FIG. 11, ozonization tank 9, alkalization tank 12 and solid-liquid separation tank 17 are arranged between anaerobic digestion tank 1 and organic wastewater feed conduit 2. Ozone generator 10 is connected to ozonization tank 9 via ozone gas supply conduit 11. Alkaline solution storage tank 13 is connected to alkalization tank 12 via alkaline solution supply conduit 14 and conduit 14 is equipped with pump 15 for supplying alkaline solution. Ozonization tank 9 is connected to alkalization tank 12 via drain 16 and alkalization tank 12 is connected to solid-liquid separation tank 17 via drain 18. Solid-liquid separation tank 17 is connected to anaerobic digestion tank 1 via conduit 19 for feeding treated sludge.

Solid-liquid separation tank 17 is also connected to phosphorus recovery tank 24 via drain 20 for phosphorus containing water and phosphorus recovery tank 24 is connected to anaerobic digestion tank 1 via conduit 26 for feeding phosphorus removed water. Coagulant supply conduit 23 equipped with coagulant supply pump 22 connects coagulant storage tank 21 to drain 20. Conduit 25 for recovered phosphorus is also connected to phosphorus recovery tank 24.

Moreover, anaerobic digestion tank 1 is connected, to solid-liquid separation tank 4 via drain 3 for drawing digested sludge. Drain 5 for thickened sludge and drain 8 for supernatant water are connected to solid-liquid separation tank 4. Drain 5 branches into two conduits; one, i.e. conduit 6, is for disposing sludge and the other, i.e. conduit 7, is for returning sludge to anaerobic digestion tank 1. Anaerobic digestion tank 1 has vent 27 for digester gas.

Hereinafter, workings of the apparatus according to the present embodiment are described.

As organic wastewater to be treated, organic sludge from a water treatment plant, which is a mixture of raw sludge from a primary sedimentation tank and excess sludge from an aeration tank, is introduced into ozonization tank 9 via conduit 2. The organic sludge is treated with ozone by injecting ozone gas from ozone generator 10 into ozonization tank 9 via conduit 11. In this ozone treatment process, the ozone injection rate is preferably 0.01 to 0.10 g-$O_3$/g-SS and more preferably 0.03 to 0.07 g-$O_3$/g-SS. With an ozone injection rate smaller than 0.01 g-$O_3$/g-SS, organic sludge is not sufficiently denatured and digestion thereof, that is, yield of methane hardly increases. In addition thereto, phosphorus in the sludge is hardly eluted out with such a small ozone injection rate. Although a larger ozone injection rate enhances both yield of methane and elution of phosphorus, this enhancement becomes slower with an ozone injection rate larger than 0.10 g-$O_3$/g-SS. Therefore, an ozone injection rate larger than 0.10 g-$O_3$/g-SS is considered uneconomical.

The organic sludge treated with ozone is sent to alkalization tank 12 via drain 16 for ozone treated sludge. Pump 15 works to supply sodium hydroxide solution from alkaline solution storage tank 13 to the alkalization tank 12 via the alkaline solution supply conduit 14 and, thereby, the organic sludge is treated with alkali. The organic sludge may preferably be treated with alkali for 5 to 30 minutes maintaining pH within a range of 9 to 13. With a pH smaller than 9, organic sludge is not sufficiently denatured and digestion thereof, that is, yield of methane hardly increases. In addition thereto, phosphorus in the sludge is hardly eluted out with a pH smaller than 9. Although higher alkalinity enhances both yield of methane and elution of phosphorus, this enhancement becomes slower with a pH higher than 13. Therefore, a pH higher than 13 is considered uneconomical. Similarly, in case where the treatment is shorter than 5 minutes, organic sludge is not sufficiently denatured and digestion thereof, that is, yield of methane hardly increases. In addition thereto, phosphorus in the sludge is hardly eluted out with treatment shorter than 5 minutes. Although longer alkali treatment enhances both yield of methane and elution of phosphorus, this enhancement becomes slower with treatment longer than 30 minutes. Therefore, alkali treatment longer than 30 minutes is considered uneconomical.

The organic sludge treated with alkali is sent to solid-liquid separation tank 17 via drain 18 and separated into sludge solid component and sludge dissolved component. Hereinafter, the term "sludge solid component" means solution containing many solids of the organic sludge and the term "sludge dissolved component" means a solution containing substantially no solids of the organic sludge. After being separated from the organic sludge, the sludge solid component is introduced into anaerobic digestion tank 1 via conduit 19 and anaerobically digested by microorganisms. Meanwhile, the sludge dissolved component rich in phosphorus is introduced into phosphorus recovery tank 24 via drain 20. At the same time, calcium carbonate solution in coagulant storage tank 21 is injected into the phosphorus containing solution flowing through drain 20 by coagulant supply pump 22 via coagulant supply conduit 23 and, thereby, phosphorus in the sludge dissolved component is fixed and precipitates as calcium phosphate. The precipitate in phosphorus recovery tank 24, i.e. calcium phosphate, is separated from the solution and drawn out from conduit 25, while the remaining solution without phosphorus is introduced into anaerobic digestion tank 1 via conduit 26 for feeding phosphorus removed water.

The digested sludge in anaerobic digestion tank 1 is discharged from drain 3 and separated into sludge solid component and sludge dissolved component in solid-liquid separation tank 4. The sludge dissolved component is discharged from drain 8 for supernatant water and the sludge solid component is discharged from drain 5 for thickened sludge.

The sludge solid component in drain 5 is discharged through conduit 6 for disposing sludge, but part of the sludge solid component is returned to anaerobic digestion tank 1 through conduit 7 for returning sludge. Meanwhile, the digester gas in anaerobic digestion tank 1 is recovered from vent 27.

With the above described combination of preceding ozone and succeeding alkali treatments, organic sludge is synergistically affected by strong oxidation by ozone and decomposition by alkali and, more specifically, decomposition of organic substances by alkali treatment is highly enhanced by previously oxidizing the surface thereof with ozone. As a result of this synergistic effect, hardly soluble substances of the solids in organic sludge, such as fibers and cell walls, can be denatured and converted into easily soluble substances and, thereby, easily digested by sludge in the anaerobic digestion tank. This improvement in solubilization is much greater than that obtained with ozone treatment alone or alkali treatment alone and, importantly, greater than the sum of these improvements so yield of methane is greatly improved and sludge to be disposed is greatly reduced.

In addition, dissolution of cell walls is enhanced with the above synergistic effect of preceding ozone and succeeding alkali treatments, as decomposition of organic substances with alkali is highly enhanced by previously oxidizing the surface thereof with ozone. As a result, phosphorus in the solids of organic sludge is efficiently eluted out, solidified with a coagulant and recovered as reusable phosphorus. According to the present embodiment, therefore, it is possible to treat organic sludge while simultaneously recovering energy and resources, i.e. digester gas and phosphorus.

In the present embodiment, all the organic wastewater introduced into the anaerobic digestion tank is treated with ozone and alkali. However, part of the organic sludge may be treated with ozone and alkali, while the rest may be introduced into the anaerobic digestion tank without ozone and/or alkali treatment.

In the present embodiment, influent organic wastewater is introduced to the ozonization tank. However, influent organic wastewater may be introduced to the anaerobic digestion tank and digested sludge drawn from the anaerobic digestion tank may be introduced to the ozonization tank. Moreover, the digested sludge drawn from the anaerobic digestion tank may be subjected to solid-liquid separation and thickened digested sludge may be introduced to the ozonization tank. Furthermore, two or more of influent organic wastewater, digested sludge and thickened digested sludge may be introduced to the ozonization tank.

Embodiment 2

Another apparatus embodying the present invention and a process of treating organic wastewater with the apparatus is described.

Figure 12:
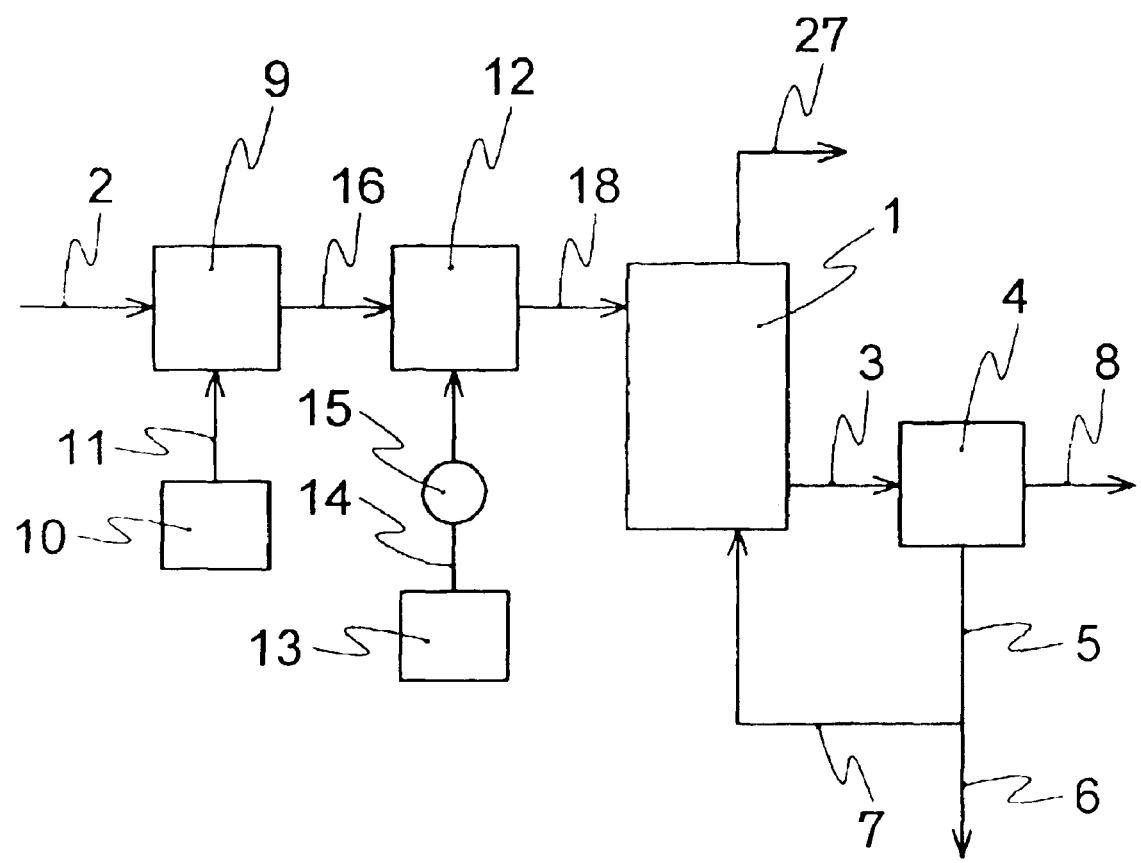
FIG. 12 is a diagram showing an apparatus embodying the present invention and a process flow of treating organic wastewater according to the present invention.

FIG. 12 is a diagram of an apparatus embodying the present invention and shows a process flow of treating organic wastewater with the apparatus. In the apparatus of the present embodiment shown in FIG. 12, components for recovering phosphorus are left out from the apparatus of Embodiment 1 shown in FIG. 11. More specifically, solid-liquid separation tank 17, conduit 19, drain 20, coagulant storage tank 21, coagulant supply pump 22, coagulant supply conduit 23, phosphorus recovery tank 24, conduit 25 for recovering phosphorus and conduit 26 for feeding phosphorus removed water arc left out and drain 18 for alkali treated sludge is connected to anaerobic digestion tank 1 in FIG. 12. Other than those above, the apparatus of the present embodiment conforms to that of Embodiment 1 shown in FIG. 11.

Hereinafter, workings of the apparatus according to the present embodiment are described.

As the organic wastewater to be treated, organic sludge from a water treatment plant, which is a mixture of raw sludge from a primary sedimentation tank and excess sludge from an aeration tank, is introduced into ozonization tank 9 via conduit 2. The organic sludge is treated with ozone by injecting ozone gas from ozone generator 10 into ozonization tank 9 via conduit 11.

The organic sludge treated with ozone is sent to alkalization tank 12 via drain 16 for ozone treated sludge. Pump 15 works to supply sodium hydroxide solution from alkaline solution storage tank 13 to alkalization tank 12 via alkaline solution supply conduit 14 and, thereby, the organic sludge is treated with alkali.

The organic sludge treated with alkali is introduced into anaerobic digestion tank 1 via drain 18 for alkali treated sludge. The organic sludge is digested by microorganisms in anaerobic digestion tank 1 and, then, the sludge inside anaerobic digestion tank 1 is discharged from drain 3 for digested sludge. The digested sludge discharged from drain 3 is separated into sludge solid component and sludge dissolved component in solid-liquid separation tank 4. The sludge dissolved component is discharged from drain 8 for supernatant water and the sludge solid component is discharged from drain 5 for thickened sludge.

The sludge solid component in drain 5 is discharged through conduit 6 for disposing sludge, but part of the sludge solid component is returned to anaerobic digestion tank 1 through conduit 7 for returning sludge. Meanwhile, the digester gas in the anaerobic digestion tank 1 is recovered from vent 27.

The present embodiment is preferable when the organic sludge contains little phosphorus and recovering energy from the sludge is a priority. With the above described combination of preceding ozone and succeeding alkali treatments, organic sludge is synergistically affected by strong oxidation by ozone and decomposition by alkali and, more specifically, decomposition of organic substances by alkali treatment is highly enhanced by previously oxidizing the surface thereof with ozone. As a result of this synergistic effect, hardly soluble substances of the solids in organic sludge, such as fibers and cell walls, can be denatured and converted into easily soluble substances and, thereby, easily digested by sludge in the anaerobic digestion tank. This improvement in solubilization is much greater than that obtained with ozone treatment alone or alkali treatment alone and, importantly, greater than the sum of these improvements so yield of methane is greatly improved and sludge to be disposed is greatly reduced.

In the present embodiment, all the organic wastewater to the anaerobic digestion tank is treated with ozone and alkali. However, part of the organic wastewater may be treated with ozone and alkali, while the rest may be introduced into the anaerobic digestion tank without ozone and/or alkali treatment.

Embodiment 3

Another apparatus embodying the present invention and a process of treating organic wastewater with the apparatus is described. In Embodiment 1, influent organic wastewater is treated with ozone and successively treated with alkali. In the present embodiment, digested sludge drawn from the anaerobic digestion tank is treated with ozone and successively treated with alkali.

Figure 13:
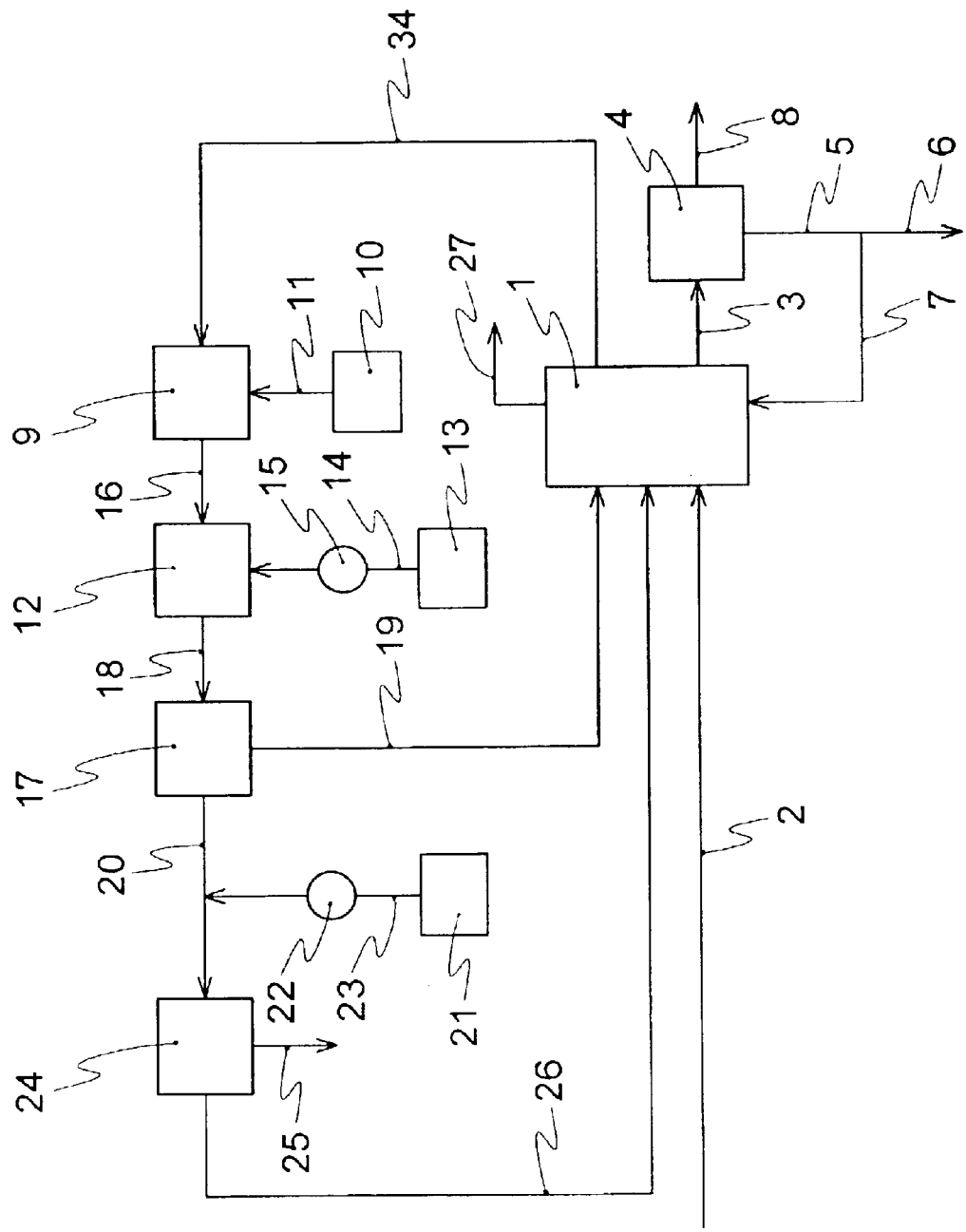
FIG. 13 is a diagram showing an apparatus embodying the present invention and a process flow of treating organic wastewater according to the present invention.

FIG. 13 is a diagram of an apparatus embodying the present invention and shows a process flow of treating organic wastewater with the apparatus. As shown in FIG. 13, organic wastewater feed conduit 2 is connected to anaerobic digestion tank 1. Conduit 34 for drawing digested sludge out is connected to anaerobic digestion tank 1 and leads to ozonization tank 9. Ozonization tank 9 is connected to alkalization tank 12 via drain 16 for ozone treated sludge and alkalization tank 12 is connected to solid-liquid separation tank 17 via drain 18 for alkali treated sludge. Ozone generator 10 is connected to ozonization tank 9 via ozone gas supply conduit 11. Alkaline solution storage tank 13 is connected to alkalization tank 12 via alkaline solution supply conduit 14 and conduit 14 is equipped with pump 15 for supplying alkaline solution. Solid-liquid separation tank 17 is connected to anaerobic digestion tank 1 via conduit 19 for feeding treated sludge.

Solid-liquid separation tank 17 is also connected to phosphorus recovery tank 24 via drain 20 for phosphorus containing water and phosphorus recovery tank 24 is connected to anaerobic digestion tank 1 via conduit 26 for feeding phosphorus removed water. Coagulant supply conduit 23 equipped with coagulant supply pump 22 connects coagulant storage tank 21 to drain 20. Conduit 25 for recovered phosphorus is also connected to phosphorus recovery tank 24.

Moreover, anaerobic digestion tank 1 is connected to solid-liquid separation tank 4 via drain 3 for drawing digested sludge. Drain 5 for thickened sludge and drain 8 for supernatant water are connected to solid-liquid separation tank 4. Drain 5 branches into two conduits; one, i.e. conduit 6, is for disposing sludge and the other, i.e. conduit 7, is for returning sludge to anaerobic digestion tank 1. Anaerobic digestion tank 1 has vent 27 for digester gas.

Hereinafter, workings of the apparatus according to the present embodiment are described.

As organic wastewater to be treated, organic sludge from a water treatment plant, which is a mixture of raw sludge from a primary sedimentation tank and excess sludge from an aeration tank, is introduced into anaerobic digestion tank 1 via conduit 2. The organic sludge is digested with microorganisms in anaerobic digestion tank 1 and, then, the sludge inside anaerobic digestion tank 1 is drawn out from drain 3. The sludge from the drain 3 is separated into sludge solid component and sludge dissolved component in solid-liquid separation tank 4. The sludge dissolved component is discharged from drain 8 for supernatant water and the sludge solid component is discharged from drain 5 for thickened sludge.

The sludge solid component in drain 5 is discharged through conduit 6 for disposing sludge, but part of the sludge solid component is returned to anaerobic digestion tank 1 through conduit 7 for returning sludge. Meanwhile, the digester gas in the anaerobic digestion tank 1 is recovered from vent 27.

In the above anaerobic digestion process, the digested sludge inside anaerobic digestion tank 1 is drawn out from conduit 34 and sent to ozonization tank 9. The digested sludge is treated with ozone by injecting ozone gas from ozone generator 10 into ozonization tank 9 via conduit 11.

The digested sludge treated with ozone is sent to alkalization tank 12 via drain 16 for ozone treated sludge. Pump 15 works to supply sodium hydroxide solution from alkaline solution storage tank 13 to alkalization tank 12 via alkaline solution supply conduit 14 and, thereby, the digested sludge is treated with alkali.

The digested sludge treated with alkali is sent to solid-liquid separation tank 17 via drain 18 and separated into sludge solid component and sludge dissolved component. The sludge solid component is introduced into anaerobic digestion tank 1 via conduit 19 and anaerobically digested by microorganisms. Meanwhile, the sludge dissolved component rich in phosphorus is introduced into phosphorus recovery tank 24 via drain 20. At the same time, calcium carbonate solution in coagulant storage tank 21 is injected into and mixed with the phosphorus containing solution flowing through drain 20 by coagulant supply pump 22 via coagulant supply conduit 23 and, thereby, phosphorus in the sludge dissolved component is fixed and precipitates as calcium phosphate. The precipitate in phosphorus recovery tank 24, i.e. calcium phosphate, is separated from the solution and drawn out from conduit 25, while the remaining solution without phosphorus is introduced into anaerobic digestion tank 1 via conduit 26 for feeding phosphorus removed water.

With the above described combination of preceding ozone and succeeding alkali treatments, digested sludge is synergistically affected by strong oxidation by ozone and decomposition by alkali and, more specifically, decomposition of organic substances by alkali treatment is highly enhanced by previously oxidizing the surface thereof with ozone. As a result of this synergistic effect, hardly soluble substances of the solids in digested sludge, such as fibers and cell walls, can be denatured and converted into easily soluble substances and, thereby, easily digested by sludge in the anaerobic digestion tank. This improvement in solubilization is much greater than that obtained with ozone treatment alone or alkali treatment alone and, importantly, greater than the sum of these improvements so yield of methane is greatly improved and sludge to be disposed is greatly reduced.

In addition, dissolution of cell walls is enhanced with the above synergistic effect of preceding ozone and succeeding alkali treatments, as decomposition of organic substances with alkali is highly enhanced by previously oxidizing the surface thereof with ozone. As a result, phosphorus in the solids of digested sludge is efficiently eluted out, solidified with coagulant and recovered as reusable phosphorus. According to the present embodiment, therefore, it is possible to treat digested sludge while simultaneously recovering energy and resources, i.e. digester gas and phosphorus.

In the digested sludge of the anaerobic digestion tank, hardly soluble substances, i.e. substances which organisms cannot decompose, remain and accumulate. According to the present embodiment, therefore, recovery of energy is achieved more efficiently by drawing out part of the digested sludge inside the anaerobic digestion tank and denaturing solid substances in the drawn digested sludge into easily soluble substances.

Embodiment 4

Another apparatus embodying the present invention and a process of treating organic wastewater with the apparatus is described.

Figure 14:
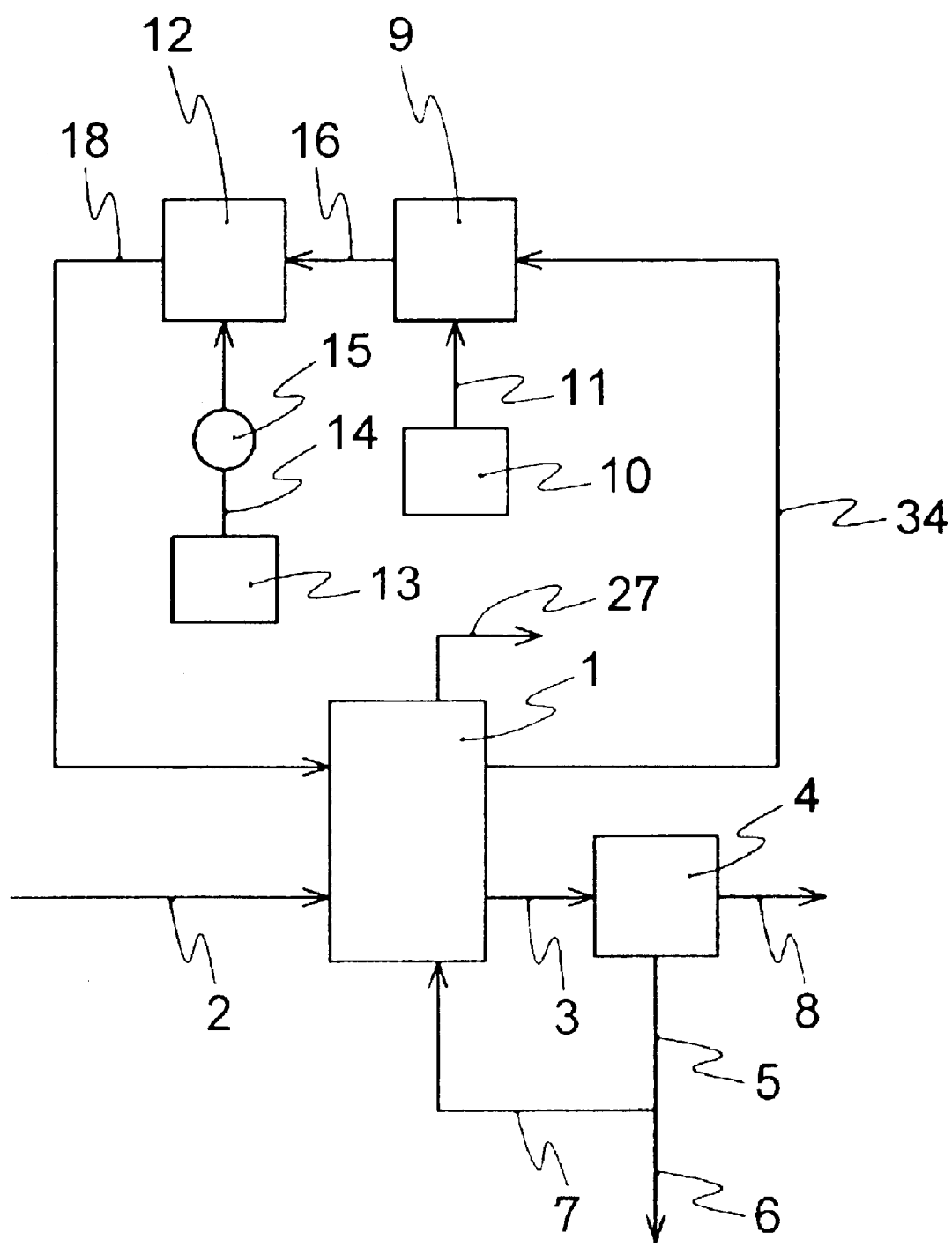
FIG. 14 is a diagram showing an apparatus embodying the present invention and a process flow of treating organic wastewater according to the present invention.

FIG. 14 is a diagram of an apparatus embodying the present invention and shows a process flow of treating organic wastewater with the apparatus. In the apparatus of the present embodiment shown in FIG. 14, components for recovering phosphorus are left out from the apparatus of Embodiment 3 shown in FIG. 13. More specifically, solid-liquid separation tank 17, conduit 19, drain 20, coagulant storage tank 21, coagulant supply pump 22, coagulant supply conduit 23, phosphorus recovery tank 24, conduit 25 for recovering phosphorus and conduit 26 for feeding phosphorus removed water are left out and drain 18 for alkali treated sludge is connected to anaerobic digestion tank 1 in FIG. 14. Other than those above, the apparatus of the present embodiment conforms to that of Embodiment 3 shown in FIG. 13.

Hereinafter, workings of the apparatus according to the present embodiment are described.

As organic wastewater to be treated, organic sludge from a water treatment plant, which is a mixture of raw sludge from a primary sedimentation tank and excess sludge from an aeration tank, is introduced into anaerobic digestion tank 1 via conduit 2. The organic sludge is digested with microorganisms in anaerobic digestion tank 1 and, then, the sludge inside the anaerobic digestion tank 1 is drawn out from drain 3. The sludge from drain 3 is separated into sludge solid component and sludge dissolved component in solid-liquid separation tank 4. The sludge dissolved component is discharged from drain 8 for supernatant water and the sludge solid component is discharged from drain 5 for thickened sludge.

The sludge solid component in drain 5 is discharged through conduit 6 for disposing sludge, but part of the sludge solid component is returned to anaerobic digestion tank 1 through conduit 7 for returning sludge. Meanwhile, the digester gas in the anaerobic digestion tank 1 is recovered from vent 27.

In the above anaerobic digestion process, the digested sludge inside anaerobic digestion tank 1 is drawn out from conduit 34 and sent to ozonization tank 9. The digested sludge is treated with ozone by injecting ozone gas from ozone generator 10 into ozonization tank 9 via conduit 11.

The digested sludge treated with ozone is sent to the alkalization tank 12 via the drain 16 for ozone treated sludge. The pump 15 works to supply sodium hydroxide solution from the alkaline solution storage tank 13 to alkalization tank 12 via alkaline solution supply conduit 14 and, thereby, the digested sludge is treated with alkali.

The digested sludge treated with alkali is introduced into anaerobic digestion tank 1 via drain 18 and anaerobically digested by microorganisms.

The present embodiment is preferable when the organic sludge contains little phosphorus and recovering energy from the sludge is a priority. With the above described combination of preceding ozone and succeeding alkali treatments, digested sludge is synergistically affected by strong oxidation by ozone and decomposition by alkali and, more specifically, decomposition of organic substances by alkali treatment is highly enhanced by previously oxidizing the surface thereof with ozone. As a result of this synergistic effect, hardly soluble substances of the solids in digested sludge, such as fibers and cell walls, can be denatured and converted into easily soluble substances and, thereby, easily digested by sludge in the anaerobic digestion tank. This improvement in solubilization is much greater than that obtained with ozone treatment alone or alkali treatment alone and, importantly, greater than the sum of these improvements so yield of methane is greatly improved and sludge to be disposed is greatly reduced.

In the digested sludge of the anaerobic digestion tank, hardly soluble substances, i.e. substances which organisms cannot decompose, remain and accumulate. According to the present embodiment, therefore, recovery of energy is achieved more efficiently by drawing out a part of digested sludge inside the anaerobic digestion tank and denaturing solid substances in the drawn digested sludge into easily soluble substances.

Embodiment 5

Another apparatus embodying the present invention and a process of treating organic wastewater with the apparatus is described. In Embodiment 1, influent organic wastewater is treated with ozone and, successively, treated with alkali. In Embodiment 3, digested sludge drawn from the anaerobic digestion tank is treated with ozone and, successively, treated with alkali. In the present embodiment, digested sludge drawn from the anaerobic digestion tank is thickened through solid-liquid separation and the thickened digested sludge is treated with ozone and, successively, treated with alkali.

Figure 15:
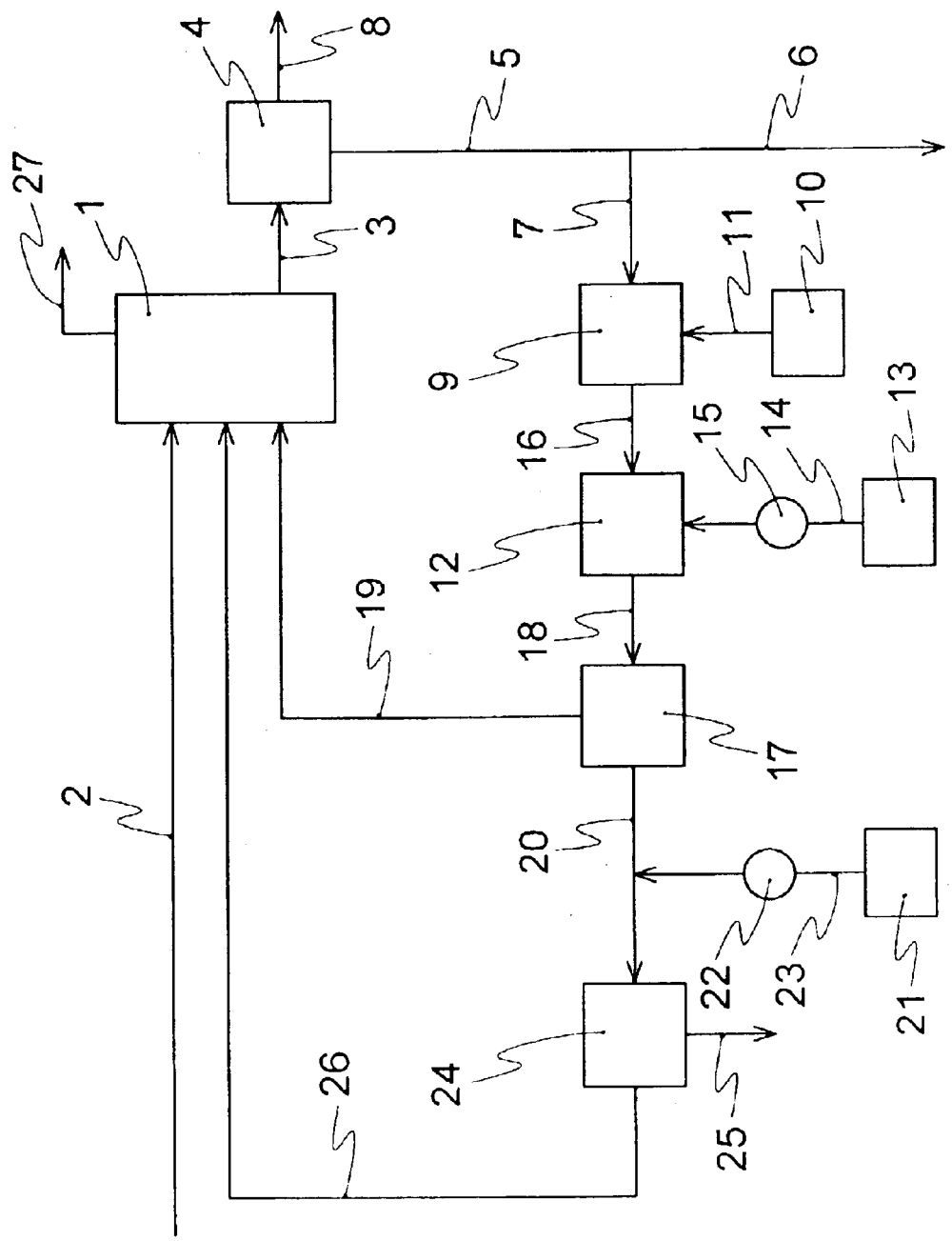
FIG. 15 is a diagram showing an apparatus embodying the present invention and a process flow of treating organic wastewater according to the present invention.

FIG. 15 is a diagram of an apparatus embodying the present invention and shows a process flow of treating organic wastewater with the apparatus. As shown in FIG. 15, organic wastewater feed conduit 2 is connected to anaerobic digestion tank 1. Anaerobic digestion tank 1 is connected to solid-liquid separation tank 4 via drain 3 for drawing digested sludge. Drain 5 for thickened sludge and drain 8 for supernatant water are connected to solid-liquid separation tank 4. Drain 5 branches into two conduits; one, i.e. conduit 6, is for disposing sludge and the other, i.e. conduit 7, is for returning sludge to ozonization tank 9. Ozonization tank 9 is connected to alkalization tank 12 via drain 16 for ozone treated sludge and alkalization tank 12 is connected to solid-liquid separation tank 17 via drain 18 for alkali treated sludge. Solid-liquid separation tank 17 is connected to anaerobic digestion tank 1 via a conduit 19 for feeding treated sludge and connected to phosphorus recovery tank 24 via drain 20 for phosphorus containing water. Phosphorus recovery tank 24 is connected to anaerobic digestion tank 1 via conduit 26 for feeding phosphorus removed water. Anaerobic digestion tank 1 has vent 27 for digester gas.

Moreover, ozone generator 10 is connected to ozonization tank 9 via ozone gas supply conduit 11. Alkaline solution storage tank 13 is connected to alkalization tank 12 via alkaline solution supply conduit 14 and conduit 14 is equipped with pump 15 for supplying alkaline solution. Solid-liquid separation tank 17 is connected to phosphorus recovery tank 24 via drain 20 for phosphorus containing water and coagulant supply conduit 23 equipped with a coagulant supply pump 22 connects coagulant storage tank 21 to the drain 20. Furthermore, conduit 25 for recovered phosphorus is connected to phosphorus recovery tank 24.

Hereinafter, workings of the apparatus according to the present embodiment are described.

As organic wastewater to be treated, organic sludge from a water treatment plant, which is a mixture of raw sludge from a primary sedimentation tank and excess sludge from an aeration tank, is introduced into anaerobic digestion tank 1 via conduit 2. The organic sludge is digested with microorganisms in anaerobic digestion tank 1 and, then, the sludge inside anaerobic digestion tank 1 is drawn out from drain 3. The sludge from drain 3 is separated into sludge solid component and sludge dissolved component in solid-liquid separation tank 4. The sludge dissolved component is discharged from drain 8 for supernatant water and the sludge solid component is discharged from drain 5 for thickened sludge.

The sludge solid component in drain 5 is discharged through conduit 6 for disposing sludge, but part of the sludge solid component is sent to ozonization tank 9 through conduit 7 for returning sludge. Meanwhile, the digester gas in anaerobic digestion tank 1 is recovered from vent 27.

After being introduced into ozonization tank 9 through conduit 7, the thickened sludge is treated with ozone by injecting ozone gas from ozone generator 10 into ozonization tank 9 via conduit 11.

The thickened sludge treated with ozone is sent to alkalization tank 12 via drain 16 for ozone treated sludge. Pump 15 works to supply sodium hydroxide solution from alkaline solution storage tank 13 to alkalization tank 12 via alkaline solution supply conduit 14 and, thereby, the thickened sludge is treated with alkali.

The thickened sludge treated with alkali is sent to solid-liquid separation tank 17 via drain 18 and separated into sludge solid component and sludge dissolved component. The sludge solid component is introduced into anaerobic digestion tank 1 via conduit 19 and anaerobically digested by microorganisms. Meanwhile, the sludge dissolved component rich in phosphorus is introduced into phosphorus recovery tank 24 via drain 20. At the same time, calcium carbonate solution in coagulant storage tank 21 is injected into and mixed with the phosphorus containing solution flowing through drain 20 by coagulant supply pump 22 via coagulant supply conduit 23 and, thereby, phosphorus in the sludge dissolved component is fixed and precipitates as calcium phosphate. The precipitate in the phosphorus recovery tank 24, i.e. calcium phosphate, is separated from the solution and drawn out from conduit 25, while the remaining solution without phosphorus is introduced into anaerobic digestion tank 1 via conduit 26 for feeding phosphorus removed water.

With the above described combination of preceding ozone and succeeding alkali treatments, thickened digested sludge is synergistically affected by strong oxidation by ozone and decomposition by alkali and, more specifically, decomposition of organic substances by alkali treatment is highly enhanced by previously oxidizing the surface thereof with ozone. As a result of this synergistic effect, hardly soluble substances of solids in thickened sludge, such as fibers and cell walls, can be denatured and converted into easily soluble substances and, thereby, easily digested by sludge in the anaerobic digestion tank. This improvement in solubilization is much greater than that obtained with ozone treatment alone or alkali treatment alone and, importantly, greater than the sum of these improvements so yield of methane is greatly improved and sludge to be disposed is greatly reduced.

In addition, dissolution of cell walls is enhanced with the above synergistic effect of preceding ozone and succeeding alkali treatments, as decomposition of organic substances with alkali is highly enhanced by previously oxidizing the surface thereof with ozone. As a result, phosphorus in the solids of thickened sludge is efficiently eluted out, solidified with a coagulant and recovered as reusable phosphorus. According to the present embodiment, therefore, it is possible to treat organic sludge while simultaneously recovering energy and resources, i.e. digester gas and phosphorus.

In the digested sludge of the anaerobic digestion tank, hardly soluble substances, i.e. substances which organisms cannot decompose, remain and accumulate. According to the present embodiment, therefore, recovery of energy is achieved more efficiently by thickening the sludge inside the anaerobic digestion tank and denaturing solid substances in the thickened digested sludge into easily soluble substances.

In the present embodiment, all the digested sludge returning to the anaerobic digestion tank is treated with ozone and alkali. However, part of the digested sludge returning to the anaerobic digestion tank may be treated with ozone and alkali, while the rest may be introduced into the anaerobic digestion tank without ozone and/or alkali treatment.

Embodiment 6

Another apparatus embodying the present invention and a process of treating organic wastewater with the apparatus is described.

Figure 16:
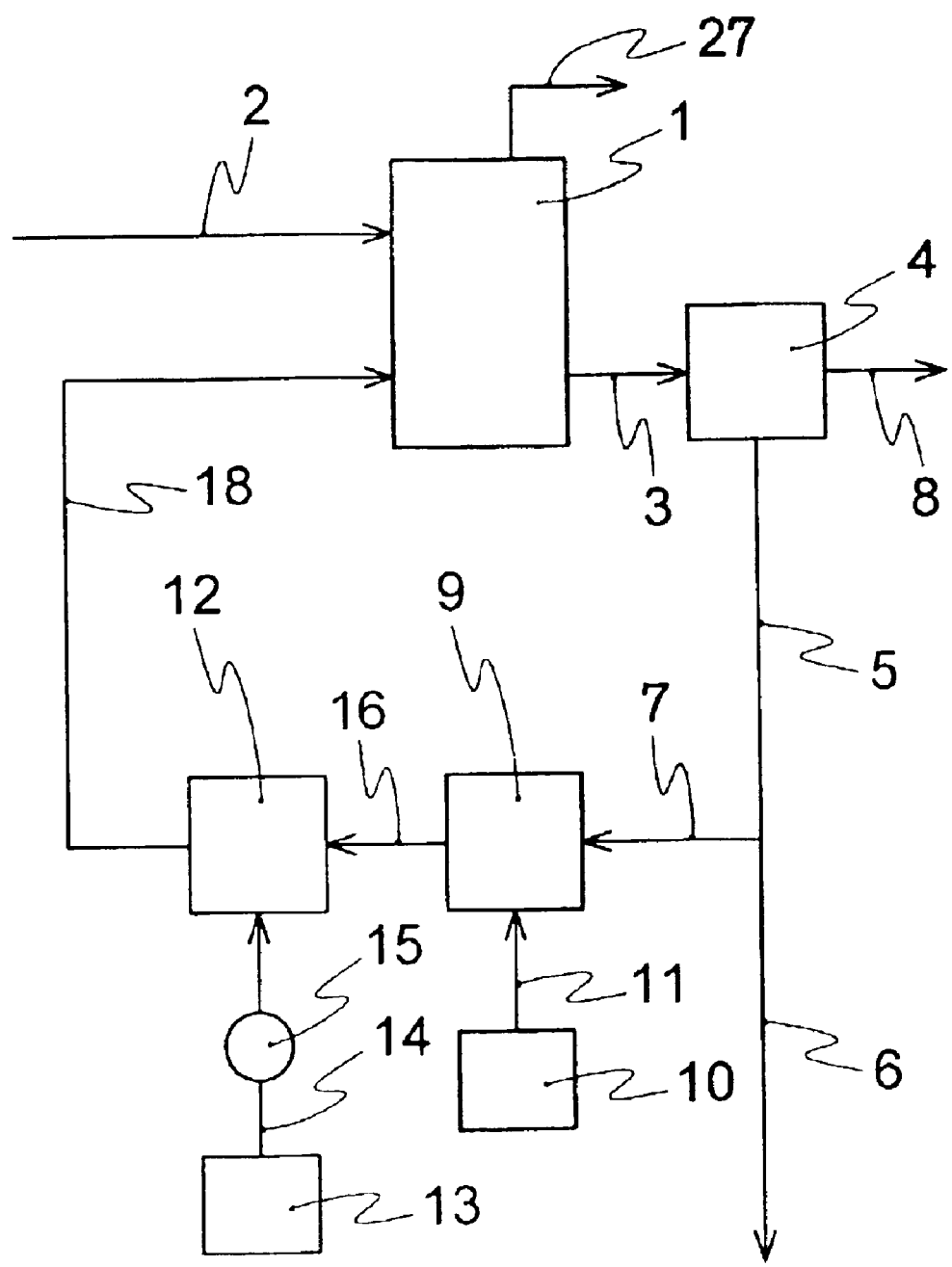
FIG. 16 is a diagram showing an apparatus embodying the present invention and a process flow of treating organic wastewater according to the present invention.

FIG. 16 is a diagram of an apparatus embodying the present invention and shows a process flow of treating organic wastewater with the apparatus. In the apparatus of the present embodiment shown in FIG. 16, components for recovering phosphorus are left out from the apparatus of Embodiment 5 shown in FIG. 15. More specifically, solid-liquid separation tank 17, conduit 19, drain 20, coagulant storage tank 21, coagulant supply pump 22, coagulant supply conduit 23, phosphorus recovery tank 24, conduit 25 for recovering phosphorus and conduit 26 for feeding phosphorus removed water are left out and drain 18 for alkali treated sludge is connected to anaerobic digestion tank 1 in FIG. 16. Other than those above, the apparatus of the present embodiment conforms to that of Embodiment 5 shown in FIG. 15.

Hereinafter, workings of the apparatus according to the present embodiment are described.

As organic wastewater to be treated, organic sludge from a water treatment plant, which is a mixture of raw sludge from a primary sedimentation tank and excess sludge from an aeration tank, is introduced into anaerobic digestion tank 1 via conduit 2. The organic sludge is digested with microorganisms in the anaerobic digestion tank 1 and, then, the sludge inside anaerobic digestion tank 1 is drawn out from drain 3. The sludge from drain 3 is separated into sludge solid component and sludge dissolved component in solid-liquid separation tank 4. The sludge dissolved component is discharged from drain 8 for supernatant water and the sludge solid component is discharged from drain 5 for thickened sludge.

The sludge solid component in drain 5 is discharged through conduit 6 for disposing sludge, but part of the sludge solid component is sent to ozonization tank 9 through conduit 7 for returning sludge. Meanwhile, the digester gas in anaerobic digestion tank 1 is recovered from vent 27.

After being introduced into ozonization tank 9 through conduit 7, the thickened sludge is treated with ozone by injecting ozone gas from ozone generator 10 into ozonization tank 9 via conduit 11.

The thickened sludge treated with ozone is sent to alkalization tank 12 via drain 16 for ozone treated sludge. Pump 15 works to supply sodium hydroxide solution from alkaline solution storage tank 13 to alkalization tank 12 via alkaline solution supply conduit 14 and, thereby, the thickened sludge is treated with alkali.

The thickened sludge treated with alkali is sent to anaerobic digestion tank 1 via drain 18 for alkali treated sludge and anaerobically digested by microorganisms.

The present embodiment is preferable when organic sludge contains little phosphorus and recovering energy from the sludge is a priority. With the above described combination of preceding ozone and succeeding alkali treatments, thickened digested sludge is synergistically affected by strong oxidation by ozone and decomposition by alkali and, more specifically, decomposition of organic substances by alkali treatment is highly enhanced by previously oxidizing the surface thereof with ozone. As a result of this synergistic effect, hardly soluble substances of the solids in thickened sludge, such as fibers and cell walls, can be denatured and converted into easily soluble substances and, thereby, easily digested by sludge in the anaerobic digestion tank. This improvement in solubilization is much greater than that obtained with ozone treatment alone or alkali treatment alone and, importantly, greater than the sum of these improvements so yield of methane is greatly improved and sludge to be disposed is greatly reduced.

In the digested sludge of the anaerobic digestion tank, hardly soluble substances, i.e. substances which organisms cannot decompose, remain and accumulate. According to the present embodiment, therefore, recovery of energy is achieved more efficiently by thickening the sludge inside the anaerobic digestion tank and denaturing solid substances in the thickened digested sludge into easily soluble substances.

In the present embodiment, all the digested sludge returning to the anaerobic digestion tank is treated with ozone and alkali. However, part of the digested sludge returning to the anaerobic digestion tank may be treated with ozone and alkali, while the rest may be introduced into the anaerobic digestion tank without ozone and/or alkali treatment.

Embodiment 7

Another apparatus embodying the present invention and a process of treating organic wastewater with the apparatus is described.

Figure 17:
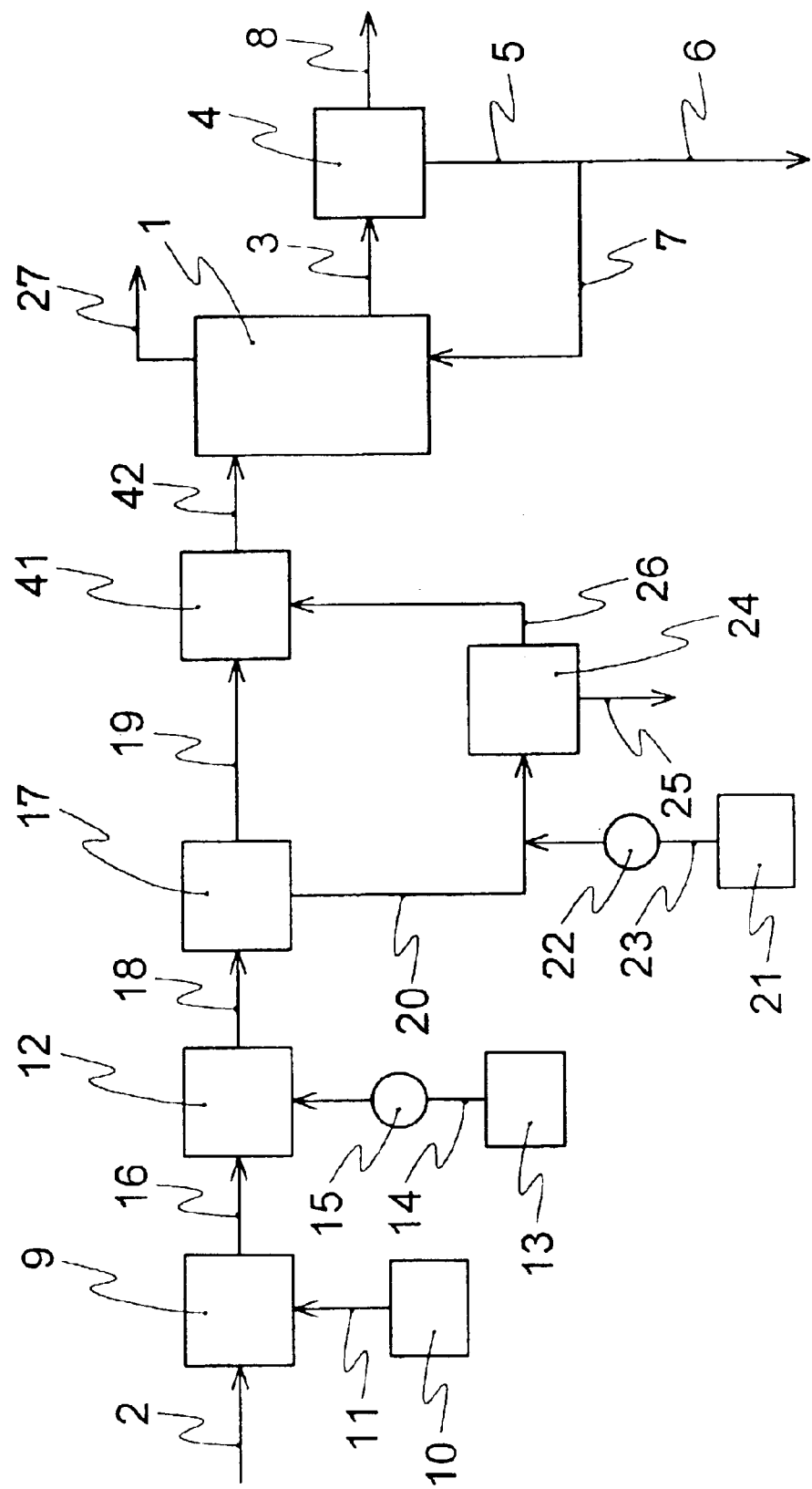
FIG. 17 is a diagram showing an apparatus embodying the present invention and a process flow of treating organic wastewater according to the present invention.

FIG. 17 is a diagram of an apparatus embodying the present invention and shows a process flow of treating organic wastewater with the apparatus. In the apparatus of the present embodiment shown in FIG. 17, the apparatus of Embodiment 1 shown in FIG. 11 is modified in such a way that conduit 19 for feeding treated sludge and conduit 26 for feeding phosphorus removed water are connected to pH regulator 41 and pH regulator 41 is connected to anaerobic digestion tank 1 via conduit 42 for introducing pH regulated sludge. Other than those above, the apparatus of the present embodiment conforms to that of Embodiment 1 shown in FIG. 11.

Hereinafter, workings of the apparatus according to the present embodiment are described.

As described in Embodiment 1, organic sludge from a water treatment plant, which is a mixture of raw sludge from a primary sedimentation tank and excess sludge from an aeration tank, is introduced into ozonization tank 9 via conduit 2 and treated with ozone. The organic sludge treated with ozone is sent to alkalization tank 12 and treated with alkali. The organic sludge treated with alkali is sent to solid-liquid separation tank 17 and separated into sludge solid component and sludge dissolved component. The sludge solid component is introduced into pH regulator 41 via the conduit 19. The sludge dissolved component is mixed with calcium carbonate solution from coagulant supply pump 22 to precipitate calcium phosphate. This precipitate is drawn out from conduit 25 and the remaining solution without phosphorus is introduced into pH regulator 41 via conduit 26. In pH regulator 41, the pH of the mixture comprising the sludge solid component and the phosphorus removed sludge dissolved component is measured and adjusted to neutral, preferably 6 to 8, by adding hydrochloric acid. Thereafter, the pH adjusted mixture is introduced into anaerobic digestion tank 1 via conduit 42 for introducing pH regulated sludge. Other than those above, the process of the present embodiment conforms to that of Embodiment 1.

With the combination of preceding ozone and succeeding alkali treatments according to the present embodiment, organic sludge is synergistically affected by strong oxidation by ozone as well as decomposition by alkali. In other words, decomposition of organic substances by alkali treatment is highly enhanced by previously oxidizing the surface thereof with ozone. As a result of this synergistic effect, hardly soluble substances of the solids in organic sludge, such as fibers and cell walls, can be denatured and converted into easily soluble substances and, thereby, easily digested by sludge in the anaerobic digestion tank. In addition, since dissolution of cell walls is enhanced with the above synergistic effect of preceding ozone and succeeding alkali treatments, phosphorus in the solids of organic sludge is efficiently eluted out. Therefore, solubility of sludge, yield of methane and the amount of eluted phosphorus are greatly increased in comparison to the effects of ozone treatment alone or alkali treatment alone and, further, the sum of the effects of these treatments.

Meanwhile, the pH of the sludge solid component separated in the solid-liquid separation tank after alkali treatment may be high due to residue of sodium hydroxide from the alkali treatment and if such sludge solid component is introduced into the anaerobic digestion tank, the pH inside the tank may suddenly change to make operations thereof unstable. Moreover, sludge dissolved component from which phosphorus is removed is preferably introduced into the anaerobic digestion tank to produce methane effectively, as the sludge dissolved component contains a great deal of organic substances that are eluted out from the sludge throughout the treatments. However, since the pH of the phosphorus removed sludge dissolved component is equal to or higher than that of the above sludge solid component after separation, introduction of such sludge dissolved component may also make the operations of the anaerobic digestion tank unstable. According to the present embodiment, therefore, acid such as hydrochloric acid is added to the sludge solid component after solid-liquid separation and/or the sludge dissolved component after phosphorus removal to make the pH substantially neutral. By introducing the sludge solid component and/or the sludge dissolved component into the anaerobic digestion tank after pH neutralization, the pH of the tank hardly changes and stable operation of the tank becomes possible.

Accordingly, a more stable and efficient treatment of organic sludge, in which energy and resources are simultaneously recovered, is achieved by the process of the present embodiment comprising preceding ozone and succeeding alkali treatments, separation into sludge solid component and sludge dissolved component, phosphorus removal from the sludge dissolved component, pH neutralization of sludge solid component and/or sludge dissolved component, and introduction to the anaerobic digestion tank.

In the present embodiment, the sludge solid component after solid-liquid separation and the sludge dissolved component after phosphorus removal are mixed and the pH of the mixture is adjusted. However, the pH of the sludge solid component after solid-liquid separation and that of the sludge dissolved component after phosphorus removal may be independently adjusted before introduction to the anaerobic digestion tank. Moreover, depending on the effects on the anaerobic digestion tank, either one of the pH of the sludge solid component after solid-liquid separation or that of the sludge dissolved component after phosphorus removal may be adjusted.

Embodiment 8

Another apparatus embodying the present invention and a process of treating organic wastewater with the apparatus is described.

Figure 18:
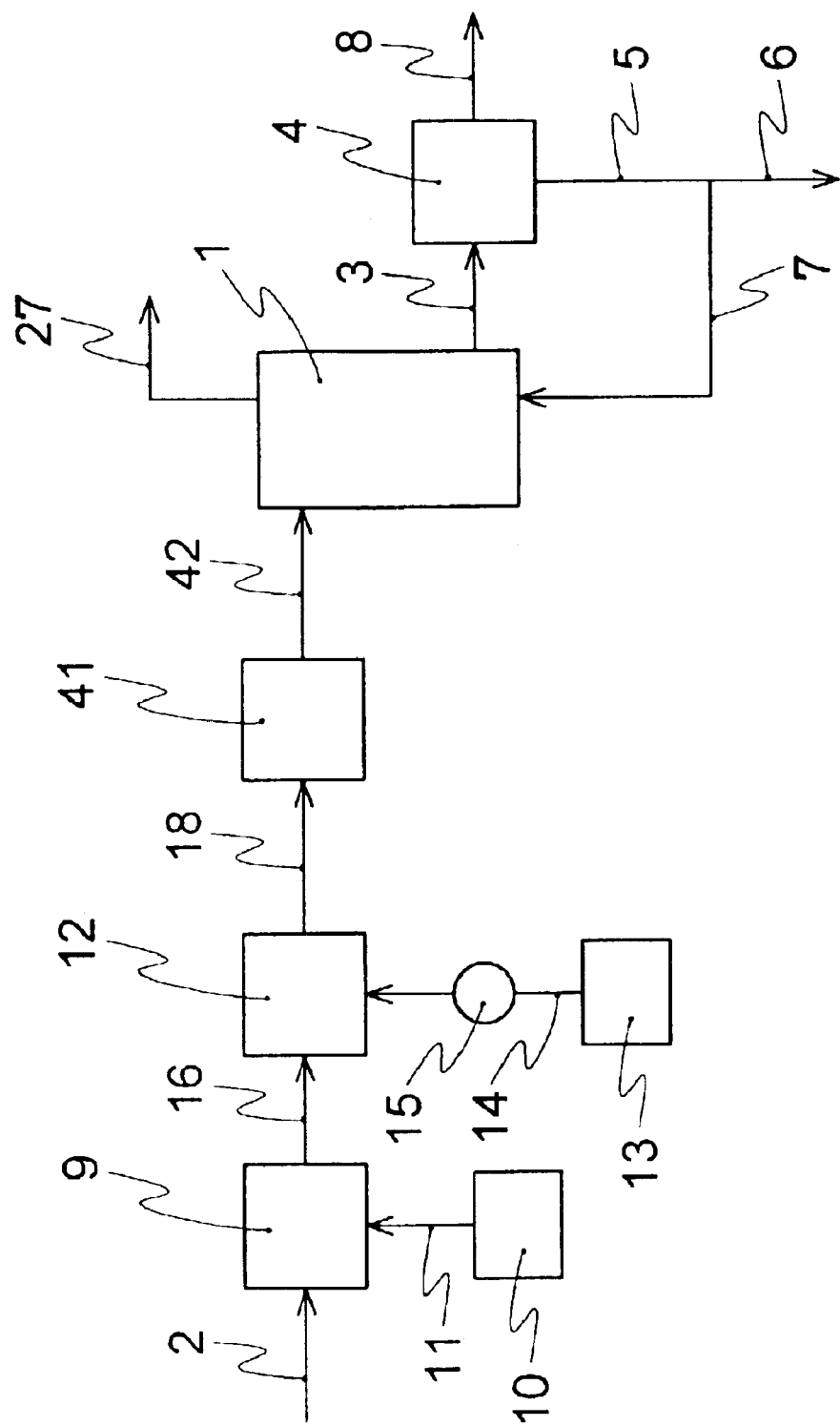
FIG. 18 is a diagram showing an apparatus embodying the present invention and a process flow of treating organic wastewater according to the present invention.

FIG. 18 is a diagram of an apparatus embodying the present invention and shows a process flow of treating organic wastewater with the apparatus. In the apparatus of the present embodiment shown in FIG. 18, components for recovering phosphorus are left out from the apparatus of Embodiment 7 shown in FIG. 17. More specifically, solid-liquid separation tank 17, conduit 19, drain 20, coagulant storage tank 21, coagulant supply pump 22, coagulant supply conduit 23, phosphorus recovery tank 24, conduit 25 for recovering phosphorus and conduit 26 for feeding phosphorus removed water are left out and drain 18 for alkali treated sludge is connected to pH regulator 41 in FIG. 18. Other than those above, the apparatus of the present embodiment conforms to that of Embodiment 7 shown in FIG. 17.

Hereinafter, workings of the apparatus according to the present embodiment are described.

As described in Embodiment 7, organic sludge from a water treatment plant, which is a mixture of raw sludge from a primary sedimentation tank and excess sludge from an aeration tank, is introduced into ozonization tank 9 via conduit 2 and treated with ozone. The organic sludge treated with ozone is introduced into alkalization tank 12 and treated with alkali. The organic sludge treated with alkali is introduced into pH regulator 41 via drain 18 for alkali treated sludge. In pH regulator 41, the pH of the organic sludge treated with ozone and alkali is measured and adjusted to neutral, preferably 6 to 8, by adding hydrochloric acid. Thereafter, the pH adjusted organic sludge is introduced into anaerobic digestion tank 1 via conduit 42 for introducing pH regulated sludge. Other than those above, the process of the present embodiment conforms to that of Embodiment 7.

The present embodiment is preferable when organic sludge contains little phosphorus and recovering energy from the sludge is a priority. With the above described combination of preceding ozone and succeeding alkali treatments according to the present embodiment, organic sludge is synergistically affected by strong oxidation by ozone and decomposition by alkali. In other words, decomposition of organic substances by alkali treatment is highly enhanced by previously oxidizing the surface thereof with ozone. As a result of this synergistic effect, hardly soluble substances of the solids in organic sludge, such as fibers and cell walls, can be denatured and converted into easily soluble substances and, thereby, easily digested by sludge in the anaerobic digestion tank. This improvement in solubilization is much greater than that obtained with ozone treatment alone or alkali treatment alone and, importantly, greater than the sum of these improvements so yield of methane is greatly improved and sludge to be disposed is greatly reduced.

Meanwhile, the pH of the organic sludge treated with alkali may be high due to residue of sodium hydroxide from alkali treatment and if such organic sludge is introduced into the anaerobic digestion tank, the pH inside the tank may suddenly change to make operations thereof unstable. According to the present embodiment, therefore, acid such as hydrochloric acid is added to the organic sludge after alkali treatment to make the pH substantially neutral. Since the organic sludge is introduced into the anaerobic digestion tank after pH neutralization, the pH of the tank hardly changes and stable operation of the tank becomes possible.

Embodiment 9

Another apparatus embodying the present invention and a process of treating organic wastewater with the apparatus is described. In Embodiment 7, influent organic wastewater is treated with ozone and successively with alkali and, then, introduced into an anaerobic digestion tank after the pH thereof is regulated. In the present embodiment, digested sludge drawn from an anaerobic digestion tank is treated with ozone and successively with alkali and, then, introduced into the anaerobic digestion tank after the pH thereof is regulated.

Figure 19:
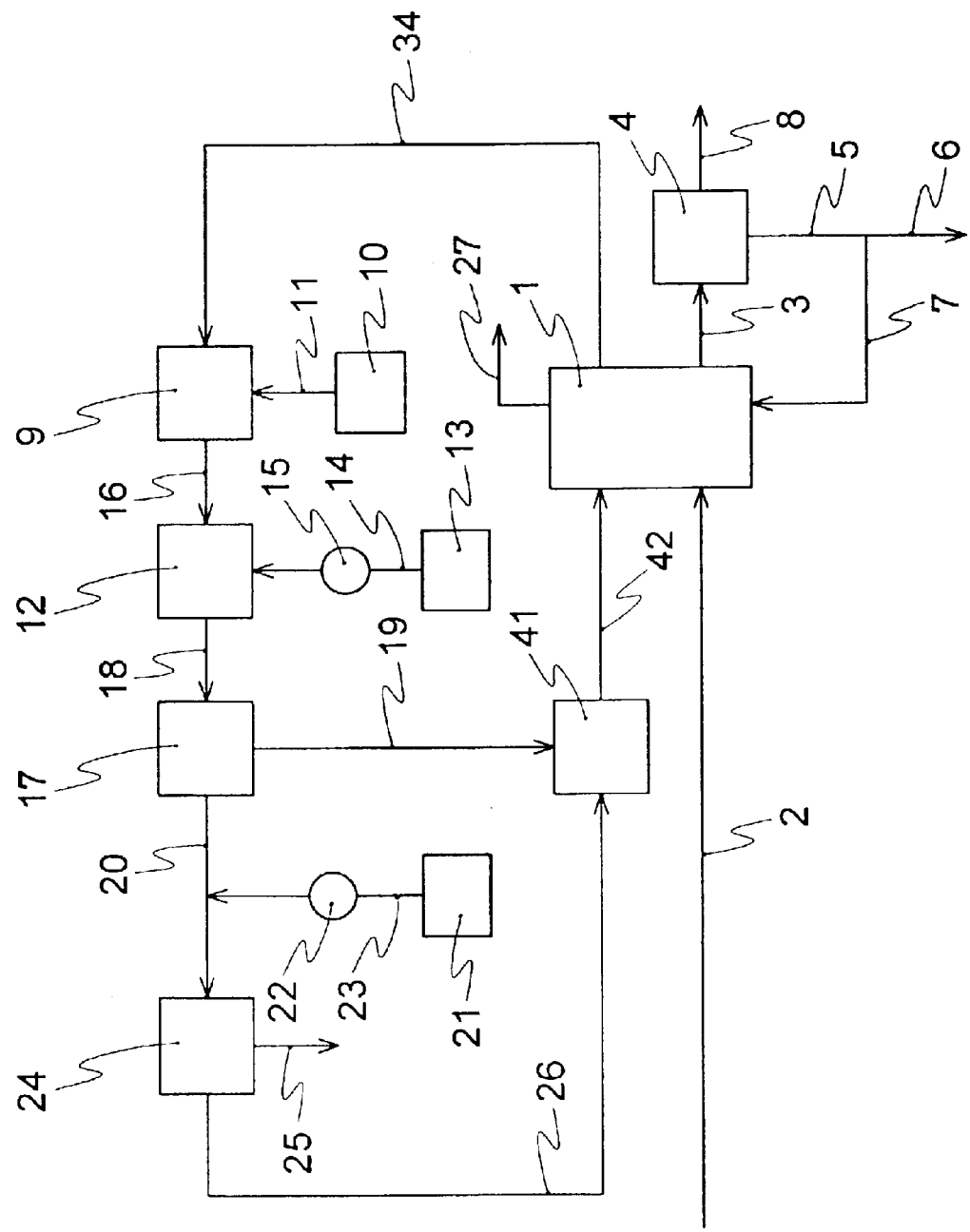
FIG. 19 is a diagram showing an apparatus embodying the present invention and a process flow of treating organic wastewater according to the present invention.

FIG. 19 is a diagram of an apparatus embodying the present invention and shows a process flow of treating organic wastewater with the apparatus. In the apparatus of the present embodiment shown in FIG. 19, the apparatus of Embodiment 3 shown in FIG. 13 is modified in such a way that conduit 19 for feeding treated sludge and conduit 26 for feeding phosphorus removed water are connected to pH regulator 41 and pH regulator 41 is connected to anaerobic digestion tank 1 via conduit 42 for introducing pH regulated sludge. Other than those above, the apparatus of the present embodiment conforms to that of Embodiment 3 shown in FIG. 13.

Hereinafter, workings of the apparatus according to the present embodiment are described.

As described in Embodiment 3, organic sludge from a water treatment plant, which is a mixture of raw sludge from a primary sedimentation tank and excess sludge from an aeration tank, is introduced into anaerobic digestion tank 1 and digested with microorganisms in anaerobic digestion tank 1. In this anaerobic digestion process, the digested sludge inside anaerobic digestion tank 1 is introduced into ozonization tank 9 through conduit 34 and treated with ozone. Then, the digested sludge treated with ozone is introduced into alkalization tank 12 and treated with alkali. Thereafter, the digested sludge treated with alkali is separated into sludge solid component and sludge dissolved component in solid-liquid separation tank 17. The sludge solid component is introduced into pH regulator 41 via the conduit 19. The sludge dissolved component is mixed with calcium carbonate solution from coagulant supply pump 22 to precipitate calcium phosphate. This precipitate is drawn out from conduit 25 and the remaining solution without phosphorus is introduced into pH regulator 41 via conduit 26. In pH regulator 41, the pH of the mixture comprising the sludge solid component and the phosphorus removed sludge dissolved component is measured and adjusted to 6 to 8 by adding hydrochloric acid. Thereafter, the pH adjusted mixture is introduced into anaerobic digestion tank 1 via conduit 42 for introducing pH regulated sludge. Other than those above, the process of the present embodiment conforms to that of Embodiment 3.

With the combination of preceding ozone and succeeding alkali treatments according to the present embodiment, digested sludge drawn from an anaerobic digestion tank is synergistically affected by strong oxidation by ozone as well as decomposition by alkali. In other words, decomposition of organic substances by alkali treatment is highly enhanced by previously oxidizing the surface thereof with ozone. As a result of this synergistic effect, hardly soluble substances of the solids in digested sludge, such as fibers and cell walls, can be denatured and converted into easily soluble substances and, thereby, easily digested by sludge in the anaerobic digestion tank. In addition, since dissolution of cell walls is enhanced with the above synergistic effect of preceding ozone and succeeding alkali treatments, phosphorus in the solids of digested sludge is efficiently eluted out. Therefore, solubility of sludge, yield of methane and the amount of eluted phosphorus are greatly increased in comparison to the effects of ozone treatment alone or alkali treatment alone and, further, the sum of the effects of these treatments.

Meanwhile, the pH of the sludge solid component separated in the solid-liquid separation tank after alkali treatment may be high due to residue of sodium hydroxide from the alkali treatment and if such sludge solid component is introduced into the anaerobic digestion tank, the pH inside the tank may suddenly change to make operations thereof unstable. Moreover, sludge dissolved component from which phosphorus is removed is preferably introduced into the anaerobic digestion tank to produce methane effectively, as the sludge dissolved component contains a great deal of organic substances that are eluted out from the sludge throughout the treatments. However, since the pH of the phosphorus removed sludge dissolved component is equal to or higher than that of the above sludge solid component after separation, introduction of such sludge dissolved component may also make the operations of the anaerobic digestion tank unstable. According to the present embodiment, therefore, acid such as hydrochloric acid is added to the sludge solid component after solid-liquid separation and/or the sludge dissolved component after phosphorus removal to make the pH substantially neutral. By introducing the sludge solid component and/or the sludge dissolved component into the anaerobic digestion tank after pH neutralization, the pH of the tank hardly changes and stable operation of the tank becomes possible.

Accordingly, a more stable and efficient treatment of organic sludge, in which energy and resources are simultaneously recovered, is achieved by treating the digested sludge drawn from the anaerobic digestion tank with the process comprising preceding ozone and succeeding alkali treatments, separation into sludge solid component and sludge dissolved component, phosphorus removal from the sludge dissolved component, pH neutralization of sludge solid component and/or sludge dissolved component, and introduction to the anaerobic digestion tank.

In the present embodiment, the sludge solid component after solid-liquid separation and the sludge dissolved component after phosphorus removal are mixed and the pH of the mixture is adjusted. However, the pH of the sludge solid component after solid-liquid separation and that of the sludge dissolved component after phosphorus removal may be independently adjusted before introduction to the anaerobic digestion tank. Moreover, depending on the effects on the anaerobic digestion tank, either one of the pH of the sludge solid component after solid-liquid separation or that of the sludge dissolved component after phosphorus removal may be adjusted.

Embodiment 10

Another apparatus embodying the present invention and a process of treating organic wastewater with the apparatus is described.

Figure 20:
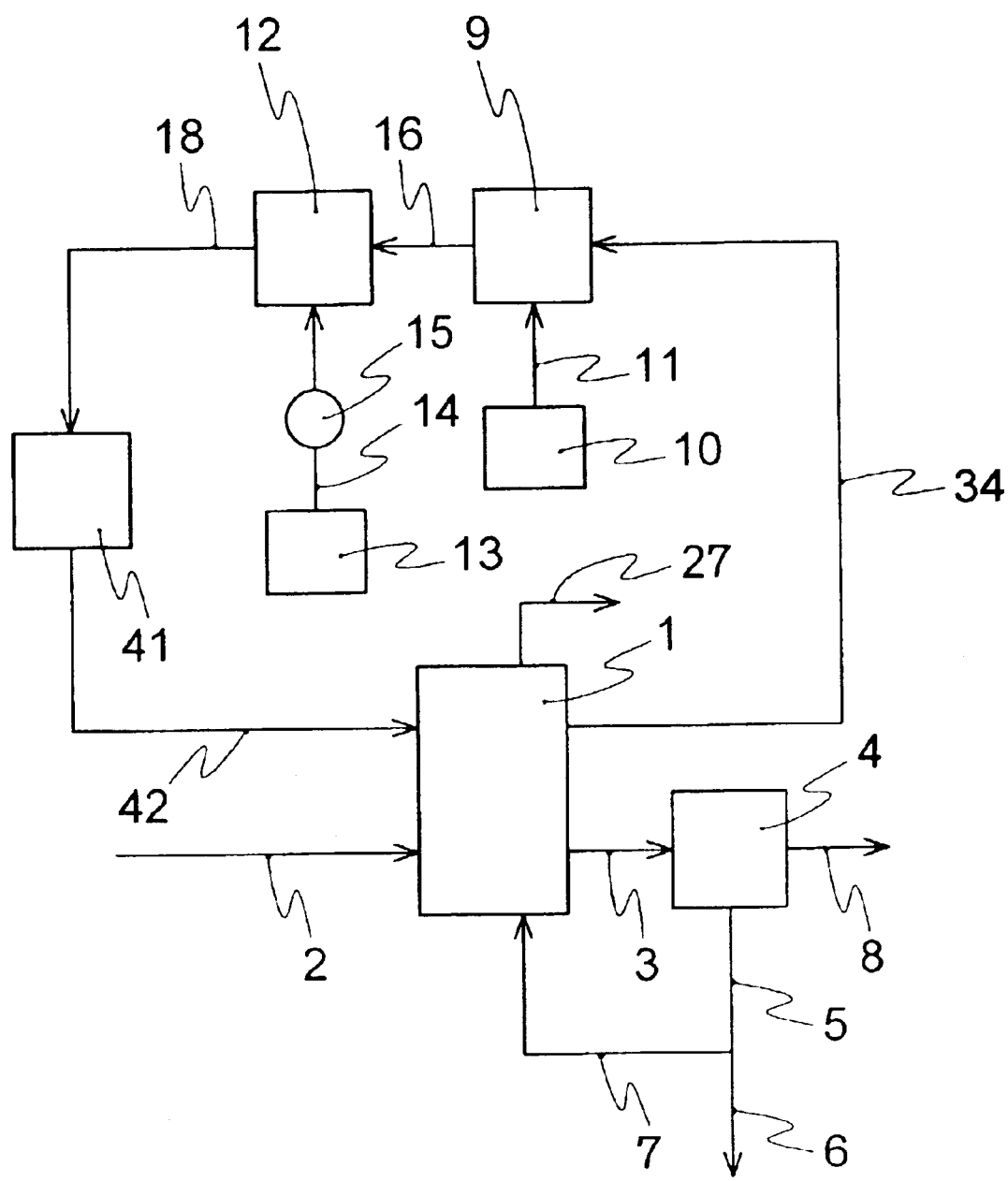
FIG. 20 is a diagram showing an apparatus embodying the present invention and a process flow of treating organic wastewater according to the present invention.

FIG. 20 is a diagram of an apparatus embodying the present invention and shows a process flow of treating organic wastewater with the apparatus. In the apparatus of the present embodiment shown in FIG. 20, components for recovering phosphorus are left out from the apparatus of Embodiment 9 shown in FIG. 19. More specifically, solid-liquid separation tank 17, conduit 19, drain 20, coagulant storage tank 21, coagulant supply pump 22, coagulant supply conduit 23, phosphorus recovery tank 24, conduit 25 for recovering phosphorus and conduit 26 for feeding phosphorus removed water are left out and drain 18 for alkali treated sludge is connected to pH regulator 41 in FIG. 20. Other than those above, the apparatus of the present embodiment conforms to that of Embodiment 9 shown in FIG. 19.

Hereinafter, workings of the apparatus according to the present embodiment are described.

As described in Embodiment 9, organic sludge from a water treatment plant, which is a mixture of raw sludge from a primary sedimentation tank and excess sludge from an aeration tank, is introduced into anaerobic digestion tank 1 and digested with microorganisms in anaerobic digestion tank 1. In this anaerobic digestion process, the digested sludge inside anaerobic digestion tank 1 is introduced into ozonization tank 9 through conduit 34 and treated with ozone. Then, the digested sludge treated with ozone is introduced into alkalization tank 12 and treated with alkali. Thereafter, the digested sludge treated with alkali is introduced into pH regulator 41 via drain 18 for alkali treated sludge. In pH regulator 41, the pH of the digested sludge treated with ozone and alkali is measured and adjusted to 6 to 8 by adding hydrochloric acid. Thereafter, the pH adjusted digested sludge is introduced into anaerobic digestion tank 1 via conduit 42 for introducing pH regulated sludge. Other than those above, the process of the present embodiment conforms to that of Embodiment 9.

The present embodiment is preferable when organic sludge contains little phosphorus and recovering energy from the sludge is a priority. With the above described combination of preceding ozone and succeeding alkali treatments according to the present embodiment, digested sludge drawn from an anaerobic digestion tank is synergistically affected by strong oxidation by ozone and decomposition by alkali. In other words, decomposition of organic substances by alkali treatment is highly enhanced by previously oxidizing the surface thereof with ozone. As a result of this synergistic effect, hardly soluble substances of the solids in digested sludge, such as fibers and cell walls, can be denatured and converted into easily soluble substances and, thereby, easily digested by sludge in the anaerobic digestion tank. This improvement in solubilization is much greater than that obtained with ozone treatment alone or alkali treatment alone and, importantly, greater than the sum of these improvements so yield of methane is greatly improved and sludge to be disposed is greatly reduced.

Meanwhile, the pH of the digested sludge treated with alkali may be high due to residue of sodium hydroxide from alkali treatment and if such digested sludge is introduced into the anaerobic digestion tank, the pH inside the tank may suddenly change to make operations thereof unstable. According to the present embodiment, therefore, acid such as hydrochloric acid is added to the organic sludge after alkali treatment to make the pH substantially neutral. Since the organic sludge is introduced into the anaerobic digestion tank after pH neutralization, the pH of the tank hardly changes and stable operation of the tank becomes possible.

Embodiment 11

Another apparatus embodying the present invention and a process of treating organic wastewater with the apparatus is described. In Embodiment 7, influent organic wastewater is treated with ozone and successively with alkali and, then, introduced into an anaerobic digestion tank after pH thereof is regulated. In Embodiment 9, digested sludge drawn from an anaerobic digestion tank is treated with ozone and successively with alkali and, then, introduced into the anaerobic digestion tank after pH thereof is regulated. In the present embodiment, meanwhile, digested sludge is thickened through solid-liquid separation, the thickened digested sludge is treated with ozone and successively with alkali and, then, introduced into the anaerobic digestion tank after pH thereof is regulated.

Figure 21:
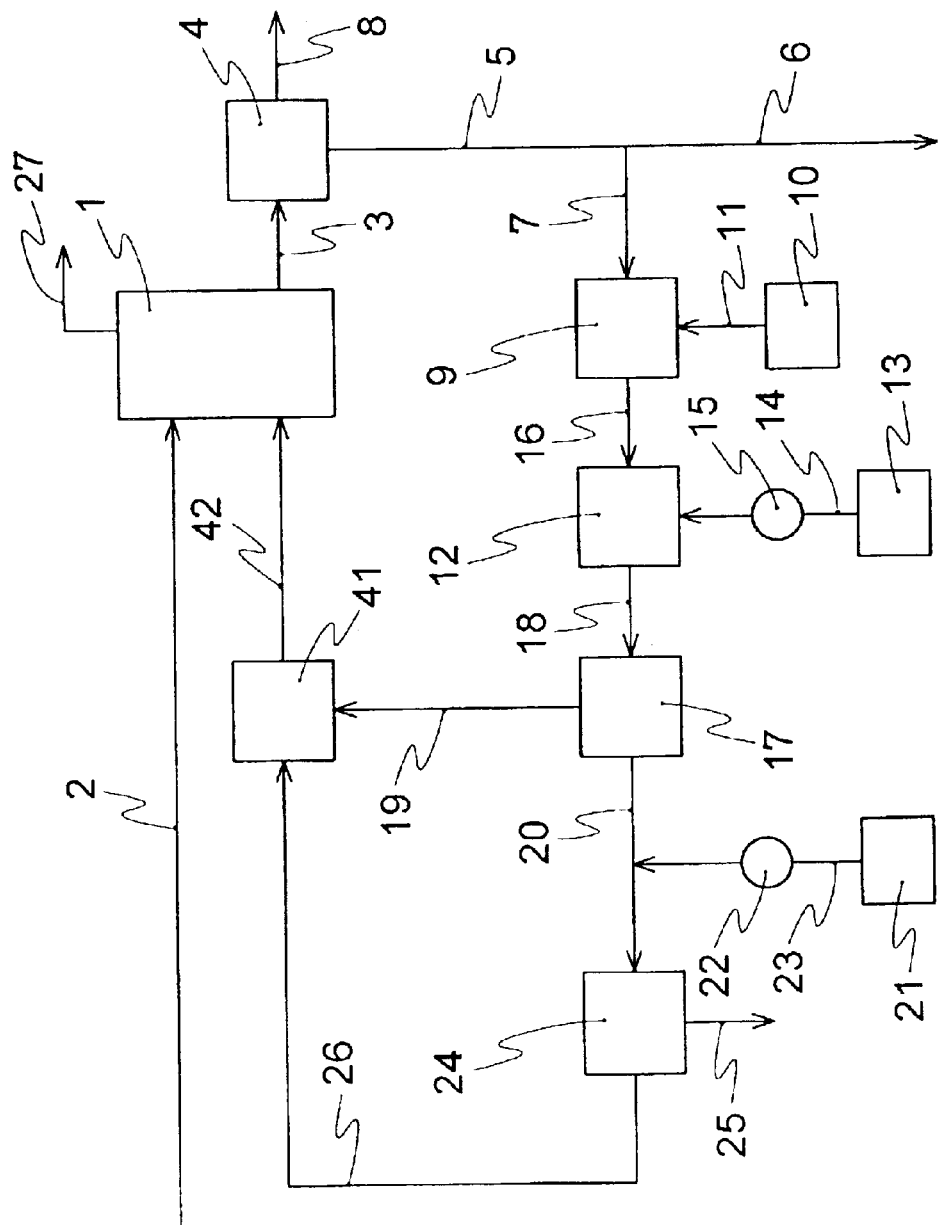
FIG. 21 is a diagram showing an apparatus embodying the present invention and a process flow of treating organic wastewater according to the present invention.

FIG. 21 is a diagram of an apparatus embodying the present invention and shows a process flow of treating organic wastewater with the apparatus. In the apparatus of the present embodiment shown in FIG. 21, the apparatus of Embodiment 5 shown in FIG. 15 is modified in such a way that conduit 19 for feeding treated sludge and conduit 26 for feeding phosphorus removed water are connected to pH regulator 41 and pH regulator 41 is connected to anaerobic digestion tank 1 via conduit 42 for introducing pH regulated sludge. Other than those above, the apparatus of the present embodiment conforms to that of Embodiment 5 shown in FIG. 15.

Hereinafter, workings of the apparatus according to the present embodiment are described.

As described in Embodiment 5, organic sludge from a water treatment plant, which is a mixture of raw sludge from a primary sedimentation tank and excess sludge from an aeration tank, is introduced into anaerobic digestion tank 1 and digested with microorganisms in anaerobic digestion tank 1. In this anaerobic digestion process, the thickened digested sludge in drain 5 is discharged through conduit 6 for disposing sludge, but part of the thickened digested sludge is introduced into ozonization tank 9 through conduit 7 and treated with ozone. Then, the thickened sludge treated with ozone is introduced into alkalization tank 12 and treated with alkali. Thereafter, the thickened sludge treated with alkali is separated into sludge solid component and sludge dissolved component in solid-liquid separation tank 17. The sludge solid component is introduced into pH regulator 41 via conduit 19. The sludge dissolved component is mixed with calcium carbonate solution from the coagulant supply pump 22 to precipitate calcium phosphate. This precipitate is drawn out from conduit 25 and the remaining solution without phosphorus is introduced into pH regulator 41 via conduit 26. In pH regulator 41, the pH of the mixture comprising the sludge solid component and the phosphorus removed sludge dissolved component is measured and adjusted to 6 to 8 by adding hydrochloric acid. Thereafter, the pH adjusted mixture is introduced into anaerobic digestion tank 1 via conduit 42 for introducing pH regulated sludge. Other than those above, the process of the present embodiment conforms to that of Embodiment 5.

With the combination of preceding ozone and succeeding alkali treatments according to the present embodiment, digested sludge drawn from an anaerobic digestion tank is thickened and, then, synergistically affected by strong oxidation by ozone as well as decomposition by alkali. In other words, decomposition of organic substances by alkali treatment is highly enhanced by previously oxidizing the surface thereof with ozone. As a result of this synergistic effect, hardly soluble substances of the solids in the thickened sludge, such as fibers and cell walls, can be denatured and converted into easily soluble substances and, thereby, easily digested by sludge in the anaerobic digestion tank. In addition, since dissolution of cell walls is enhanced with the above synergistic effect of preceding ozone and succeeding alkali treatments, phosphorus in the solids of thickened sludge is efficiently eluted out. Therefore, solubility of sludge, yield of methane and the amount of eluted phosphorus are greatly increased in comparison to the effects of ozone treatment alone or alkali treatment alone and, further, the sum of the effects of these treatments.

Meanwhile, the pH of the sludge solid component separated in the solid-liquid separation tank after alkali treatment may be high due to residue of sodium hydroxide from the alkali treatment and if such sludge solid component is introduced into the anaerobic digestion tank, the pH inside the tank may suddenly change to make operations thereof unstable. Moreover, sludge dissolved component from which phosphorus is removed is preferably introduced into the anaerobic digestion tank to produce methane effectively, as the sludge dissolved component contains a great deal of organic substances that are eluted out from the sludge throughout the treatments. However, since the pH of the phosphorus removed sludge dissolved component is equal to or higher than that of the above sludge solid component after separation, introduction of such sludge dissolved component may also make the operations of the anaerobic digestion tank unstable. According to the present embodiment, therefore, acid such as hydrochloric acid is added to the sludge solid component after solid-liquid separation and/or the sludge dissolved component after phosphorus removal to make the pH substantially neutral. By introducing sludge solid component and/or sludge dissolved component into the anaerobic digestion tank after pH neutralization, the pH of the tank hardly changes and stable operation of the tank becomes possible.

Accordingly, a more stable and efficient treatment of organic sludge, in which energy and resources are simultaneously recovered, is achieved by thickening the digested sludge drawn from the anaerobic digestion tank and treating the thickened sludge with the process comprising preceding ozone and succeeding alkali treatments, separation into sludge solid component and sludge dissolved component, phosphorus removal from the sludge dissolved component, pH neutralization of sludge solid component and/or sludge dissolved component, and introduction to the anaerobic digestion tank.

In the present embodiment, the sludge solid component after solid-liquid separation and the sludge dissolved component after phosphorus removal are mixed and the pH of the mixture is adjusted. However, the pH of the sludge solid component after solid-liquid separation and that of the sludge dissolved component after phosphorus removal may be independently adjusted before introduction to the anaerobic digestion tank. Moreover, depending on the effects on the anaerobic digestion tank, either one of the pH of the sludge solid component after solid-liquid separation or that of the sludge dissolved component after phosphorus removal may be adjusted.

Embodiment 12

Another apparatus embodying the present invention and a process of treating organic wastewater with the apparatus is described.

Figure 22:
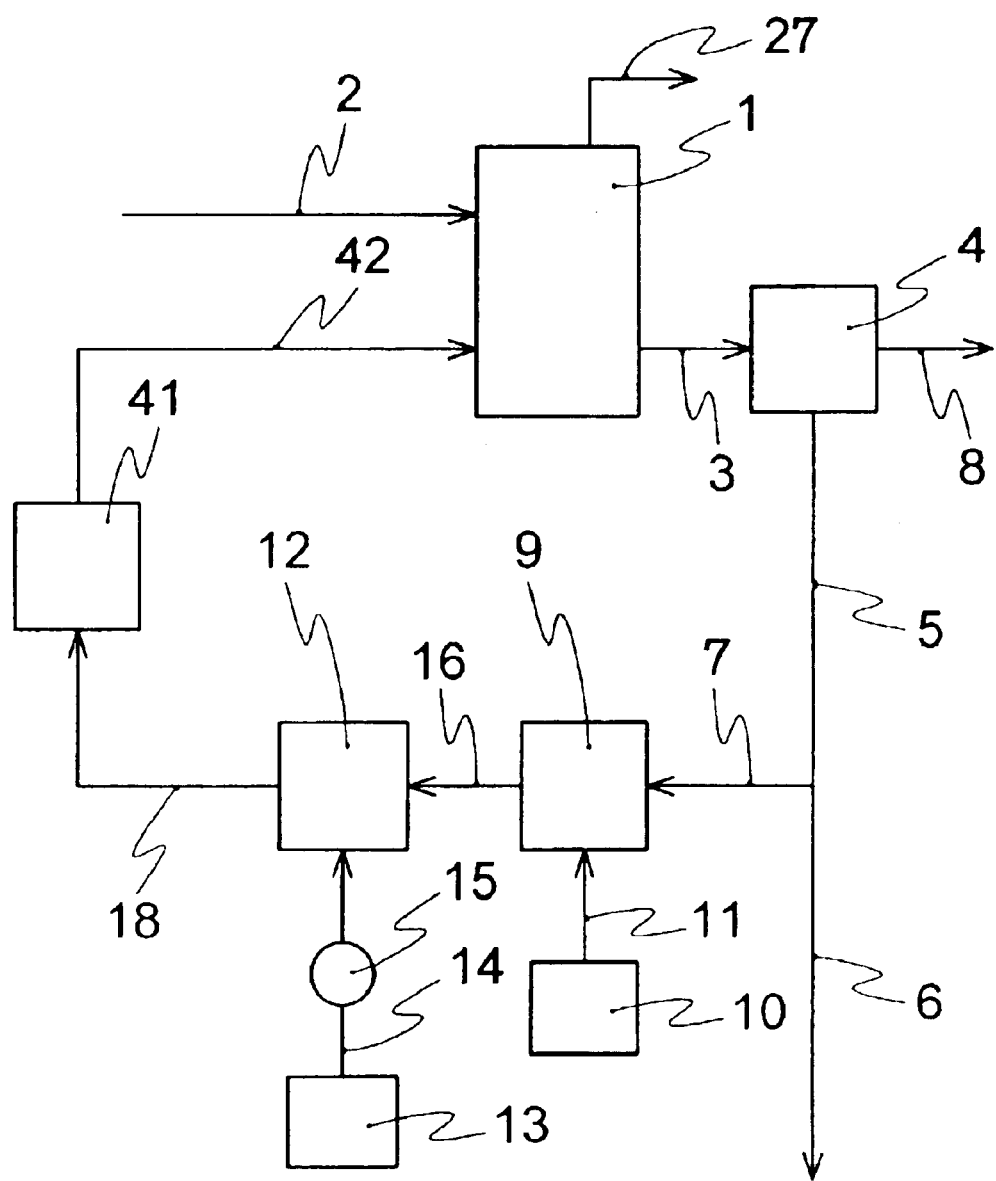
FIG. 22 is a diagram showing an apparatus embodying the present invention and a process flow of treating organic wastewater according to the present invention.

FIG. 22 is a diagram of an apparatus embodying the present invention and shows a process flow of treating organic wastewater with the apparatus. In the apparatus of the present embodiment shown in FIG. 22, components for recovering phosphorus are left out from the apparatus of Embodiment 11 shown in FIG. 21. More specifically, solid-liquid separation tank 17, conduit 19, drain 20, coagulant storage tank 21, coagulant supply pump 22, coagulant supply conduit 23, phosphorus recovery tank 24, conduit 25 for recovering phosphorus and conduit 26 for feeding phosphorus removed water are left out and drain 18 for alkali treated sludge is connected to pH regulator 41 in FIG. 22. Other than those above, the apparatus of the present embodiment conforms to that of Embodiment 11 shown in FIG. 21.

Hereinafter, workings of the apparatus according to the present embodiment are described.

As described in Embodiment 11, organic sludge from a water treatment plant, which is a mixture of raw sludge from a primary sedimentation tank and excess sludge from an aeration tank, is introduced into anaerobic digestion tank 1 and digested with microorganisms in anaerobic digestion tank 1. In this anaerobic digestion process, the thickened digested sludge in drain 5 is discharged through conduit 6 for disposing sludge, but part of the thickened digested sludge is introduced into ozonization tank 9 through conduit 7 and treated with ozone. Then, the thickened sludge treated with ozone is introduced into alkalization tank 12 and treated with alkali. Thereafter, the thickened sludge treated with alkali is introduced into pH regulator 41 via drain 18 for alkali treated sludge. In pH regulator 41, the pH of the thickened sludge treated with ozone and alkali is measured and adjusted to 6 to 8 by adding hydrochloric acid. Thereafter, the pH adjusted thickened sludge is introduced into anaerobic digestion tank 1 via conduit 42 for introducing pH regulated sludge. Other than those above, the process of the present embodiment conforms to that of Embodiment 11.

The present embodiment is preferable when organic sludge contains little phosphorus and recovering energy from the sludge is a priority. With the above described combination of preceding ozone and succeeding alkali treatments according to the present embodiment, digested sludge drawn from an anaerobic digestion tank is thickened and, then, synergistically affected by strong oxidation by ozone as well as decomposition by alkali. In other words, decomposition of organic substances by alkali treatment is highly enhanced by previously oxidizing the surface thereof with ozone. As a result of this synergistic effect, hardly soluble substances of the solids in thickened sludge, such as fibers and cell walls, can be denatured and converted into easily soluble substances and, thereby, easily digested by sludge in the anaerobic digestion tank. This improvement in solubilization is much greater than that obtained with ozone treatment alone or alkali treatment alone and, importantly, greater than the sum of these improvements so yield of methane is greatly improved and sludge to be disposed is greatly reduced.

Meanwhile, the pH of the thickened sludge treated with alkali may be high due to residue of sodium hydroxide from alkali treatment and if such thickened sludge is introduced into the anaerobic digestion tank, the pH inside the tank may suddenly change to make operations thereof unstable. According to the present embodiment, therefore, acid such as hydrochloric acid is added to the thickened sludge after alkali treatment to make the pH substantially neutral. By introducing thickened sludge into the anaerobic digestion tank after pH neutralization, the pH of the tank hardly and stable operation of the tank becomes possible.

Embodiment 13

Another apparatus embodying the present invention and a process of treating organic wastewater with the apparatus is described.

Figure 23:
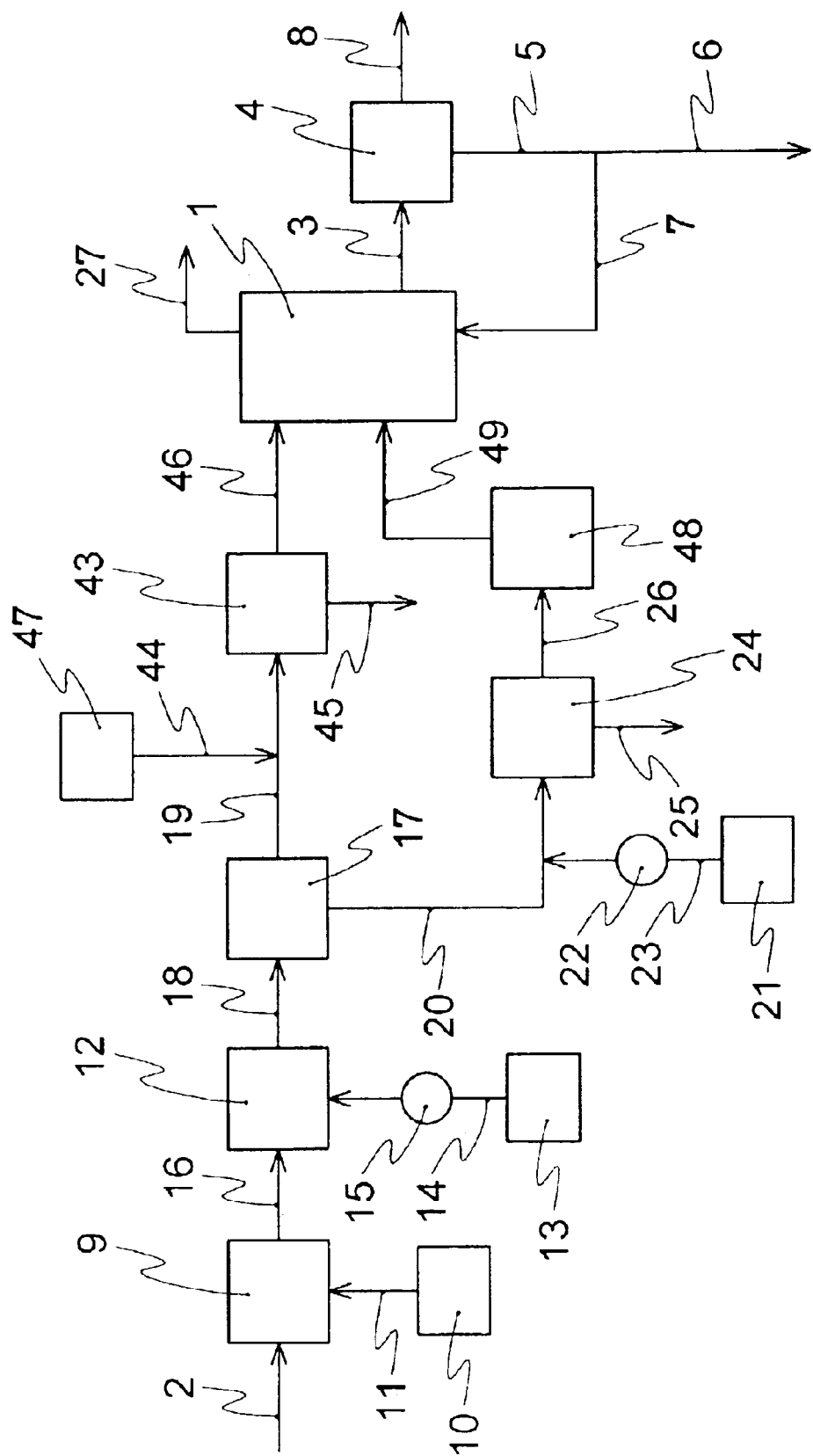
FIG. 23 is a diagram showing an apparatus embodying the present invention and a process flow of treating organic wastewater according to the present invention.

FIG. 23 is a diagram of an apparatus embodying the present invention and shows a process flow of treating organic wastewater with the apparatus. In the apparatus of the present embodiment shown in FIG. 23, the apparatus of Embodiment 1 shown in FIG. 11 is modified in such a way that rinse water supply conduit 44 connected to rinse water storage tank 47 is connected to conduit 19 for feeding treated sludge and conduit 19 is connected to hydro-extractor 43. Hydro-extractor 43 is connected to anaerobic digestion tank 1 via conduit 46 for feeding rinsed sludge. Drain 45 for extracted water is also connected to hydro-extractor 43. Meanwhile, conduit 26 for feeding phosphorus removed water is connected to ion exchanger 48 and ion exchanger 48 is connected to anaerobic digestion tank 1 via conduit 49 for feeding ion exchanged water. Other than those above, the apparatus of the present embodiment conforms to that of Embodiment 1 shown in FIG. 11.

Hereinafter, workings of the apparatus according to the present embodiment are described.

As described in Embodiment 1, organic sludge from a water treatment plant, which is a mixture of raw sludge from a primary sedimentation tank and excess sludge from an aeration tank, is introduced into ozonization tank 9 via conduit 2 and treated with ozone. The organic sludge treated with ozone is introduced into alkalization tank 12 and treated with alkali. The organic sludge treated with alkali is sent to solid-liquid separation tank 17 and separated into sludge solid component and sludge dissolved component. The sludge solid component is sent to hydro-extractor 43 via conduit 19. While sending, biologically treated water in rinse water storage tank 47 is supplied through conduit 44 and mixed with the sludge solid component flowing through the conduit 19. In hydro-extractor 43, the mixture is dehydrated, soluble ions in the sludge solid component are removed therefrom and the sludge solid component is rinsed. The rinsed sludge solid component is sent to anaerobic digestion tank 1 via conduit 46, while the extracted water is discharged from drain 45. As for the sludge dissolved component, phosphorus is removed therefrom and the sludge dissolved component after phosphorus recovery is introduced into ion exchanger 48 via conduit 26. In ion exchanger 48, ions in the sludge dissolved component after phosphorus recovery are removed and, then, the sludge dissolved component is introduced into anaerobic digestion tank 1 via conduit 49 for ion exchanged water. Other than those above, the process of the present embodiment conforms to that of Embodiment 1.

With the combination of preceding ozone and succeeding alkali treatments according to the present embodiment, organic sludge is synergistically affected by strong oxidation by ozone as well as decomposition by alkali. In other words, decomposition of organic substances by alkali treatment is highly enhanced by previously oxidizing the surface thereof with ozone. As a result of this synergistic effect, hardly soluble substances of the solids in organic sludge, such as fibers and cell walls, can be denatured and converted into easily soluble substances and, thereby, easily digested by sludge in the anaerobic digestion tank. In addition, since dissolution of cell walls is enhanced with the above synergistic effect of preceding ozone and succeeding alkali treatments, phosphorus in solids of organic sludge is efficiently eluted out. Therefore, solubility of sludge, yield of methane and the amount of eluted phosphorus are greatly increased in comparison to the effects of ozone treatment alone or alkali treatment alone and, further, the sum of the effects of these treatments.

Meanwhile, the sludge solid component separated in the solid-liquid separation tank may contain residue of sodium hydroxide from the alkali treatment and the sodium ions inhibit the activity of the microorganisms for digestion. Accordingly, the operations of the anaerobic digestion tank may become unstable if such sludge solid component is introduced into the anaerobic digestion tank. Moreover, sludge dissolved component from which phosphorus is removed is preferably introduced into the anaerobic digestion tank to produce methane effectively, as the sludge dissolved component contains a great deal of organic substances that are eluted out from the sludge throughout the treatments. However, since the sodium ion concentration of the phosphorus removed sludge dissolved component is equal to or higher than that of the above sludge solid component after separation, introduction of such sludge dissolved component may also make the operations of the anaerobic digestion tank unstable. According to the present embodiment, therefore, the sludge solid component after solid-liquid separation is rinsed and the sludge dissolved component after phosphorus removal is ion-exchanged in order to remove the sodium ions. Since the sludge solid component and the sludge dissolved component are introduced into the anaerobic digestion tank after the removal of sodium ions, deactivation of the microorganisms by sodium ions hardly occurs and stable operation of the tank becomes possible.

Accordingly, a more stable and efficient treatment of organic sludge, in which energy and resources are simultaneously recovered, is achieved by the process of the present embodiment comprising preceding ozone and succeeding alkali treatments, separation into sludge solid component and sludge dissolved component, phosphorus removal from the sludge dissolved component, sodium ion removal from the sludge solid component and sludge dissolved component, and introduction to the anaerobic digestion tank.

In the present embodiment, the sludge solid component is rinsed and the sludge dissolved component is ion-exchanged in order to remove sodium ions therefrom. However, other techniques for removing ions, such as utilizing a reverse osmosis membrane, may be applicable. Moreover, in the present embodiment, ions were removed from both the sludge solid component and the sludge dissolved component after phosphorus removal. However, depending on the effects on the anaerobic digestion tank, ions may be removed from either one of the sludge solid component after solid-liquid separation or the sludge dissolved component after phosphorus removal.

In the present embodiment, ions are removed from the sludge solid component and the sludge dissolved component after phosphorus removal and, then, the sludge solid component and the sludge dissolved component are introduced into the anaerobic digestion tank without further treatment. However, even when the pH thereof is neutralized before introduction into the anaerobic digestion tank as described in Embodiment 7, effects equal to or higher than those of the present embodiment may be obtained. Moreover, the pH of the sludge solid component and/or sludge dissolved component may be adjusted before the ions are removed therefrom and introduced into the anaerobic digestion tank.

Although biologically treated water is used for rinse water in the present embodiment, tap water, overflow effluent and rainwater are also applicable.

Embodiment 14

Another apparatus embodying the present invention and a process of treating organic wastewater with the apparatus is described.

Figure 24:
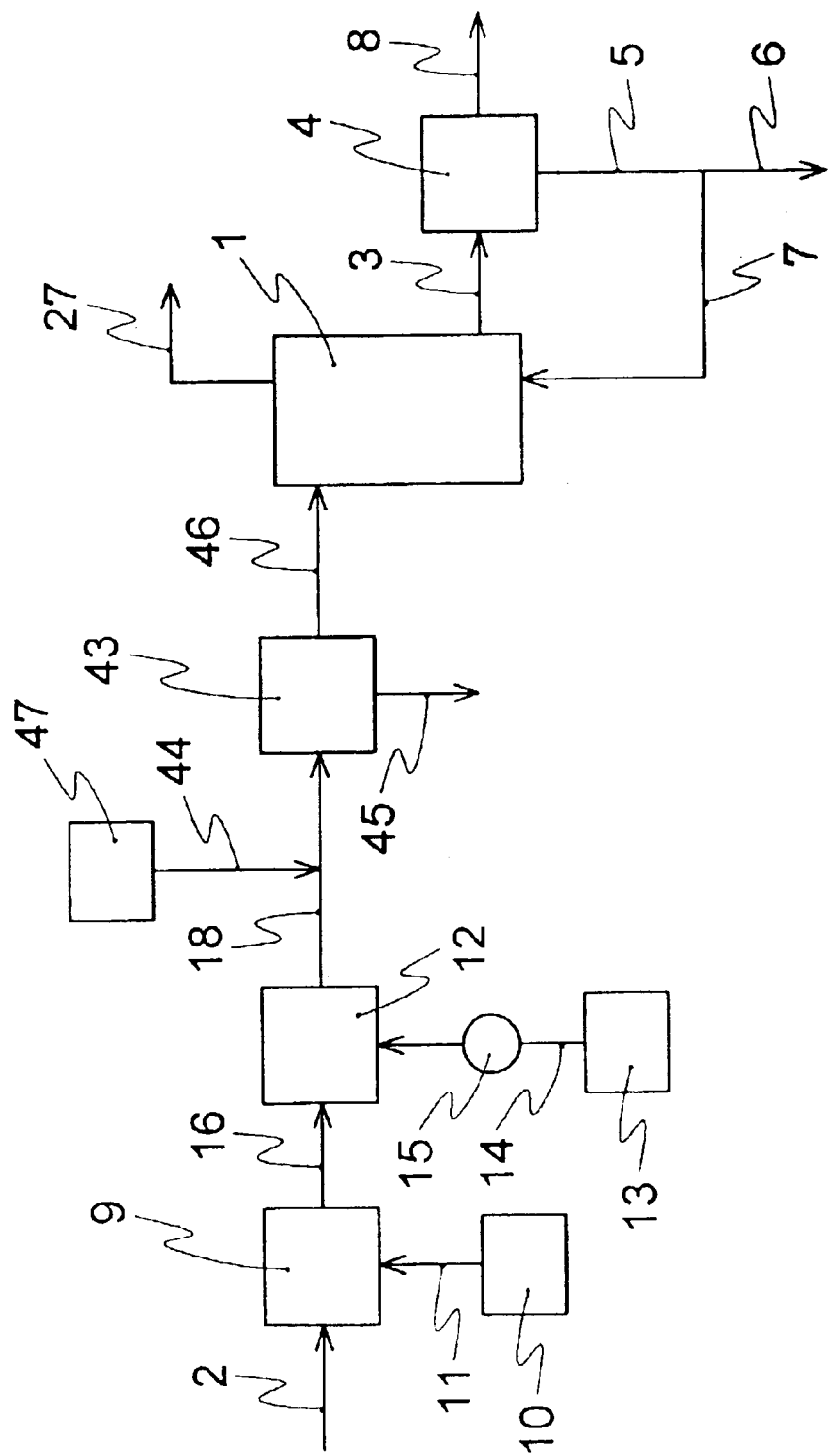
FIG. 24 is a diagram showing an apparatus embodying the present invention and a process flow of treating organic wastewater according to the present invention.

FIG. 24 is a diagram of an apparatus embodying the present invention and shows a process flow of treating organic wastewater with the apparatus. In the apparatus of the present embodiment shown in FIG. 24, components for recovering phosphorus are left out from the apparatus of Embodiment 13 shown in FIG. 23. More specifically, solid-liquid separation tank 17, conduit 19, drain 20, coagulant storage tank 21, coagulant supply pump 22, coagulant supply conduit 23, phosphorus recovery tank 24, conduit 25 for recovering phosphorus and conduit 26 for feeding phosphorus removed water are left out, rinse water supply conduit 44 connected to rinse water storage tank 47 is connected to drain 18 for alkali treated sludge and drain 18 is connected to hydro-extractor 43. Other than those above, the apparatus of the present embodiment conforms to that of Embodiment 13 shown in FIG. 23.

Hereinafter, workings of the apparatus according to the present embodiment are described.

As described in Embodiment 13, organic sludge from a water treatment plant, which is a mixture of raw sludge from a primary sedimentation tank and excess sludge from an aeration tank, is introduced into ozonization tank 9 via conduit 2 and treated with ozone. The organic sludge treated with ozone is introduced into alkalization tank 12 and treated with alkali. The organic sludge treated with alkali is sent to hydro-extractor 43 via drain 18. While sending, biologically treated water in rinse water storage tank 47 is supplied through conduit 44 and mixed with the organic sludge flowing through the drain 18. In hydro-extractor 43, the mixture is dehydrated and soluble ions in the solids of the organic sludge are removed therefrom. The organic sludge rinsed in this way is sent to anaerobic digestion tank 1 via conduit 46, while the extracted water is discharged from drain 45. Other than those above, the process of the present embodiment conforms to that of Embodiment 13.

The present embodiment is preferable when organic sludge contains little phosphorus and recovering energy from the sludge is a priority. With the above described combination of preceding ozone and succeeding alkali treatments according to the present embodiment, organic sludge is synergistically affected by strong oxidation by ozone and decomposition by alkali. In other words, decomposition of organic substances by alkali treatment is highly enhanced by previously oxidizing the surface thereof with ozone. As a result of this synergistic effect, hardly soluble substances of the solids in organic sludge, such as fibers and cell walls, can be denatured and converted into easily soluble substances and, thereby, easily digested by sludge in the anaerobic digestion tank. This improvement in solubilization is much greater than that obtained with ozone treatment alone or alkali treatment alone and, importantly, greater than the sum of these improvements so yield of methane is greatly improved and sludge to be disposed is greatly reduced.

Meanwhile, the organic sludge may contain residue of sodium hydroxide from the alkali treatment and the sodium ions inhibit the activity of the microorganisms for digestion. Accordingly, the operations of the anaerobic digestion tank may become unstable if such organic sludge is introduced into the anaerobic digestion tank. According to the present embodiment, therefore, the organic sludge after alkali treatment is rinsed in order to remove sodium ions. By introducing organic sludge from which sodium ions are removed into the anaerobic digestion tank, deactivation of the microorganisms by sodium ions hardly occurs and stable operation of the anaerobic digestion tank becomes possible.

In the present embodiment, ions are removed from the organic sludge and, then, the organic sludge is introduced into the anaerobic digestion tank without further treatment. However, even when the pH of the organic sludge is neutralized before introduction into the anaerobic digestion tank as described in Embodiment 8, effects equal to or higher than those of the present embodiment may be obtained. Moreover, the pH of the organic sludge may be adjusted before the ions are removed from the organic sludge and introduced into the anaerobic digestion tank.

Although biologically treated water is used for rinse water in the present embodiment, tap water, overflow effluent and rain water are also applicable.

Embodiment 15

Another apparatus embodying the present invention and a process of treating organic wastewater with the apparatus is described. In Embodiment 13, influent organic wastewater is treated with ozone and successively with alkali and, then, introduced into an anaerobic digestion tank after inhibitors of anaerobic digestion are removed. In the present embodiment, digested sludge drawn from an anaerobic digestion tank is treated with ozone and successively with alkali and, then, introduced into the anaerobic digestion tank after inhibitors of anaerobic digestion are removed.

Figure 25:
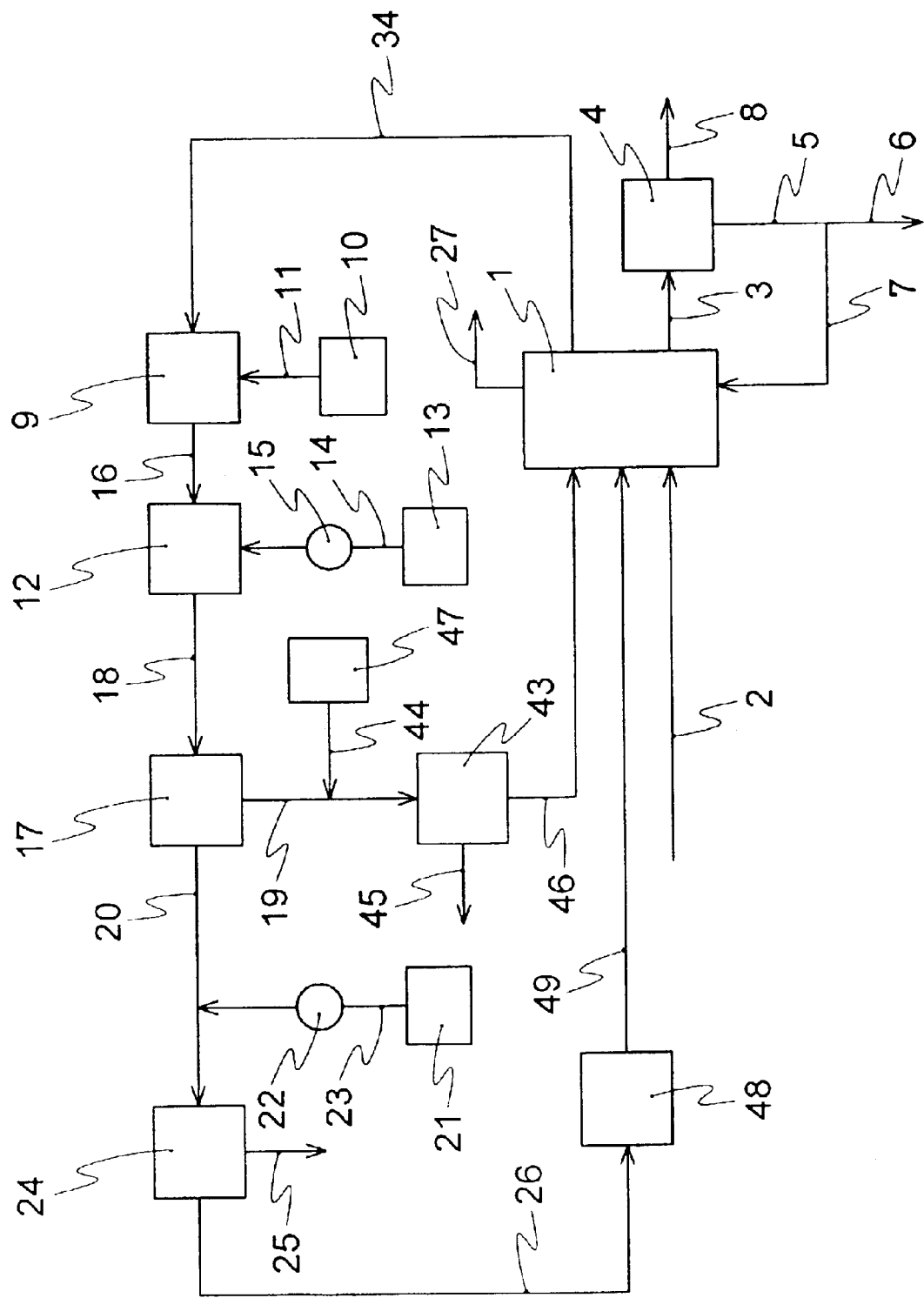
FIG. 25 is a diagram showing an apparatus embodying the present invention and a process flow of treating organic wastewater according to the present invention.

FIG. 25 is a diagram of an apparatus embodying the present invention and shows a process flow of treating organic wastewater with the apparatus. In the apparatus of the present embodiment shown in FIG. 25, the apparatus of Embodiment 3 shown in FIG. 13 is modified in such a way that rinse water supply conduit 44 connected to rinse water storage tank 47 is connected to conduit 19 for feeding treated sludge and conduit 19 is connected to hydro-extractor 43. Hydro-extractor 43 is connected to anaerobic digestion tank 1 via conduit 46 for feeding rinsed sludge. Drain 45 for extracted water is also connected to hydro-extractor 43. Meanwhile, conduit 26 for feeding phosphorus removed water is connected to ion exchanger 48 and ion exchanger 48 is connected to anaerobic digestion tank 1 via conduit 49 for feeding ion exchanged water. Other than those above, the apparatus of the present embodiment conforms to that of Embodiment 3 shown in FIG. 13.

Hereinafter, workings of the apparatus according to the present embodiment are described.

As described in Embodiment 3, organic sludge from a water treatment plant, which is a mixture of raw sludge from a primary sedimentation tank and excess sludge from an aeration tank, is introduced into anaerobic digestion tank 1 and digested with microorganisms in anaerobic digestion tank 1. In this anaerobic digestion process, the digested sludge inside anaerobic digestion tank 1 is introduced into ozonization tank 9 through conduit 34 and treated with ozone. Then, the digested sludge treated with ozone is introduced into alkalization tank 12 and treated with alkali. Thereafter, the digested sludge treated with alkali is separated into sludge solid component and sludge dissolved component in solid-liquid separation tank 17. The sludge solid component is sent to hydro-extractor 43 via conduit 19. While sending, biologically treated water in rinse water storage tank 47 is supplied through conduit 44 and mixed with the sludge solid component flowing through conduit 19. In hydro-extractor 43, the mixture is dehydrated and soluble ions in the sludge solid component are removed therefrom. The sludge solid component rinsed in this way is sent to anaerobic digestion tank 1 via conduit 46, while the extracted water is discharged from drain 45. As for the sludge dissolved component, calcium carbonate solution is added by coagulant supply pump 22 and calcium phosphate is precipitated. This precipitate is drawn out via conduit 25, while the remaining solution is introduced into ion exchanger 48 via conduit 26. In ion exchanger 48, ions in the sludge dissolved component after phosphorus recovery are removed and, then, the sludge dissolved component is introduced into anaerobic digestion tank 1 via conduit 49 for ion exchanged water. Other than those above, the process of the present embodiment conforms to that of Embodiment 3.

With the combination of preceding ozone and succeeding alkali treatments according to the present embodiment, digested sludge drawn from an anaerobic digestion tank is synergistically affected by strong oxidation by ozone as well as decomposition by alkali. In other words, decomposition of organic substances by alkali treatment is highly enhanced by previously oxidizing the surface thereof with ozone. As a result of this synergistic effect, hardly soluble substances of the solids in digested sludge, such as fibers and cell walls, can be denatured and converted into easily soluble substances and, thereby, easily digested by sludge in the anaerobic digestion tank. In addition, since dissolution of cell walls is enhanced with the above synergistic effect of preceding ozone and succeeding alkali treatments, phosphorus in the solids of digested sludge is efficiently eluted out. Therefore, solubility of sludge, yield of methane and the amount of eluted phosphorus are greatly increased in comparison to the effects of ozone treatment alone or alkali treatment alone and, further, the sum of the effects of these treatments.

Meanwhile, the sludge solid component separated in the solid-liquid separation tank after alkali treatment may contain residue of sodium hydroxide from the alkali treatment and the sodium ions inhibit the activity of the microorganisms for digestion. Accordingly, the operations of the anaerobic digestion tank may become unstable if such sludge solid component is introduced into the anaerobic digestion tank. Moreover, sludge dissolved component from which phosphorus is removed is preferably introduced into the anaerobic digestion tank to produce methane effectively, as the sludge dissolved component contains a great deal of organic substances that are eluted out from the sludge throughout the treatments. However, since the sodium ion concentration of the phosphorus removed sludge dissolved component is equal to or higher than that of the above sludge solid component after separation, introduction of such sludge dissolved component may also make the operations of the anaerobic digestion tank unstable. According to the present embodiment, therefore, the sludge solid component after solid-liquid separation is rinsed and the sludge dissolved component after phosphorus removal is ion-exchanged in order to remove the sodium ions. Since the sludge solid component and the sludge dissolved component are introduced into the anaerobic digestion tank after the removal of sodium ions, deactivation of the microorganisms by sodium ions hardly occurs and stable operation of the anaerobic digestion tank becomes possible.

Accordingly, a more stable and efficient treatment of organic sludge, in which energy and resources are simultaneously recovered, is achieved by treating the digested sludge drawn from the anaerobic digestion tank with the process comprising preceding ozone and succeeding alkali treatments, separation into sludge solid component and sludge dissolved component, phosphorus removal from the sludge dissolved component, sodium ion removal from the sludge solid component and sludge dissolved component, and introduction to the anaerobic digestion tank.

In the present embodiment, the sludge solid component is rinsed and the sludge dissolved component is ion-exchanged in order to remove sodium ions therefrom. However, other techniques for removing ions, such as utilizing a reverse osmosis membrane, may be applicable. Moreover, in the present embodiment, ions were removed from both the sludge solid component and the sludge dissolved component after phosphorus removal. However, depending on the effects on the anaerobic digestion tank, ions may be removed from either one of the sludge solid component after solid-liquid separation or the sludge dissolved component after phosphorus removal.

In the present embodiment, ions are removed from the sludge solid component and the sludge dissolved component and, then, the sludge solid component and the sludge dissolved component are introduced into the anaerobic digestion tank without further treatment. However, even when the pH thereof is neutralized before introduction into the anaerobic digestion tank as described in Embodiment 9, effects equal or higher than those of the present embodiment may be obtained. Moreover, the pH of the sludge solid component and/or sludge dissolved component may be adjusted before the ions are removed therefrom and introduced into the anaerobic digestion tank.

Although biologically treated water is used for rinse water in the present embodiment, tap water, overflow effluent and rainwater are also applicable.

Embodiment 16

Another apparatus embodying the present invention and a process of treating organic wastewater with the apparatus is described.

Figure 26:
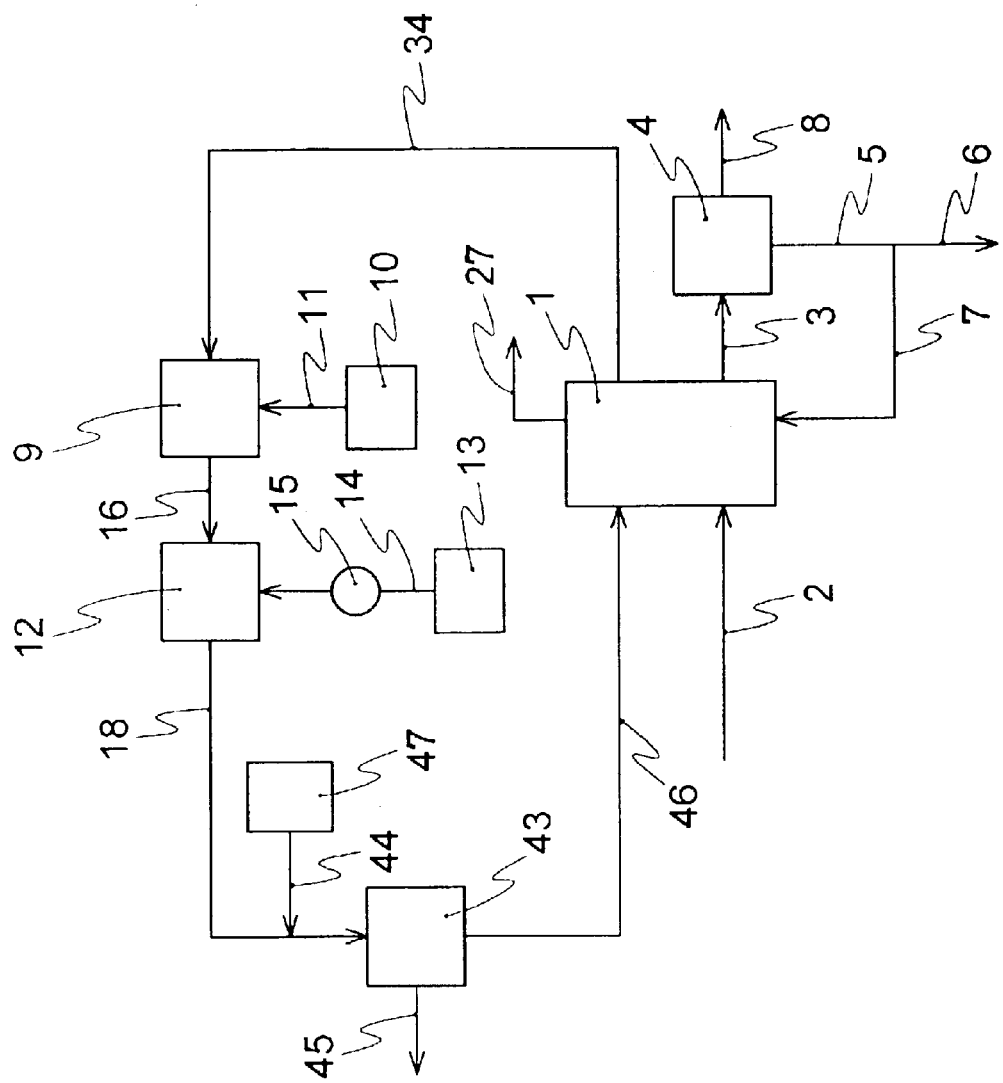
FIG. 26 is a diagram showing an apparatus embodying the present invention and a process flow of treating organic wastewater according to the present invention.

FIG. 26 is a diagram of an apparatus embodying the present invention and shows a process flow of treating organic wastewater with the apparatus. In the apparatus of the present embodiment shown in FIG. 26, components for recovering phosphorus are left out from the apparatus of Embodiment 15 shown in FIG. 25. More specifically, solid-liquid separation tank 17, conduit 19, drain 20, coagulant storage tank 21, coagulant supply pump 22, coagulant supply conduit 23, phosphorus recovery tank 24, conduit 25 for recovering phosphorus and conduit 26 for feeding phosphorus removed water are left out, rinse water supply conduit 44 connected to the rinse water storage tank 47 is connected to drain 18 for alkali treated sludge and drain 18 is connected to hydro-extractor 43. Other than those above, the apparatus of the present embodiment conforms to that of Embodiment 15 shown in FIG. 25.

Hereinafter, workings of the apparatus according to the present embodiment are described.

As described in Embodiment 15, organic sludge from a water treatment plant, which is a mixture of raw sludge from a primary sedimentation tank and excess sludge from an aeration tank, is introduced into anaerobic digestion tank 1 and digested with microorganisms in anaerobic digestion tank 1. In this anaerobic digestion process, the digested sludge inside anaerobic digestion tank 1 is introduced into ozonization tank 9 through conduit 34 and treated with ozone. Then, the digested sludge treated with ozone is introduced into alkalization tank 12 and treated with alkali. The digested sludge treated with alkali is sent to hydro-extractor 43 via drain 18. At the same time, biologically treated water in rinse water storage tank 47 is supplied through conduit 44 and mixed with the digested sludge flowing through the drain 18. In hydro-extractor 43, the mixture is dehydrated and soluble ions in the solids of the digested sludge are removed therefrom. The digested sludge rinsed in this way is sent to anaerobic digestion tank 1 via conduit 46, while the extracted water is discharged from drain 45. Other than those above, the process of the present embodiment conforms to that of Embodiment 15.

The present embodiment is preferable when digested sludge contains little phosphorus and recovering energy from the sludge is a priority. With the above described combination of preceding ozone and succeeding alkali treatments according to the present embodiment, digested sludge drawn from an anaerobic digestion tank is synergistically affected by strong oxidation by ozone and decomposition by alkali. In other words, decomposition of organic substances by alkali treatment is highly enhanced by previously oxidizing the surface thereof with ozone. As a result of this synergistic effect, hardly soluble substances of the solids in digested sludge, such as fibers and cell walls, can be denatured and converted into easily soluble substances and, thereby, easily digested by sludge in the anaerobic digestion tank. This improvement in solubilization is much greater than that obtained with ozone treatment alone or alkali treatment alone and, importantly, greater than the sum of these improvements so yield of methane is greatly improved and sludge to be disposed is greatly reduced.

Meanwhile, the digested sludge may contain residue of sodium hydroxide from the alkali treatment and the sodium ions inhibit the activity of the microorganisms for digestion. Accordingly, the operations of the anaerobic digestion tank may become unstable if such digested sludge is introduced into the anaerobic digestion tank. According to the present embodiment, therefore, the digested sludge after alkali treatment is rinsed in order to remove sodium ions. By introducing the digested sludge from which sodium ions are removed into the anaerobic digestion tank, deactivation of the microorganisms by sodium ions hardly occurs and stable operation of the anaerobic digestion tank becomes possible.

In the present embodiment, ions are removed from the digested sludge and, then, the digested sludge is introduced into the anaerobic digestion tank without further treatment. However, even when the pH of the digested sludge is neutralized before introduction to the anaerobic digestion tank as described in Embodiment 10, effects equal to of higher than those of the present embodiment may be obtained. Moreover, the pH of the digested sludge may be adjusted before the ions are removed from the digested sludge and introduced into the anaerobic digestion tank.

Although biologically treated water is used for rinse water in the present embodiment, tap water, overflow effluent and rainwater are also applicable.

Embodiment 17

Another apparatus embodying the present invention and a process of treating organic wastewater with the apparatus is described. In Embodiment 13, influent organic wastewater is treated with ozone and successively with alkali and, then, introduced into an anaerobic digestion tank after inhibitors of anaerobic digestion are removed. In Embodiment 15, digested sludge drawn from an anaerobic digestion tank is treated with ozone and successively with alkali and, then, introduced into the anaerobic digestion tank after inhibitors of anaerobic digestion are removed. In the present embodiment, digested sludge is thickened through solid-liquid separation, the thickened digested sludge is treated with ozone and successively with alkali and, then, introduced into the anaerobic digestion tank after inhibitors of anaerobic digestion are removed.

Figure 27:
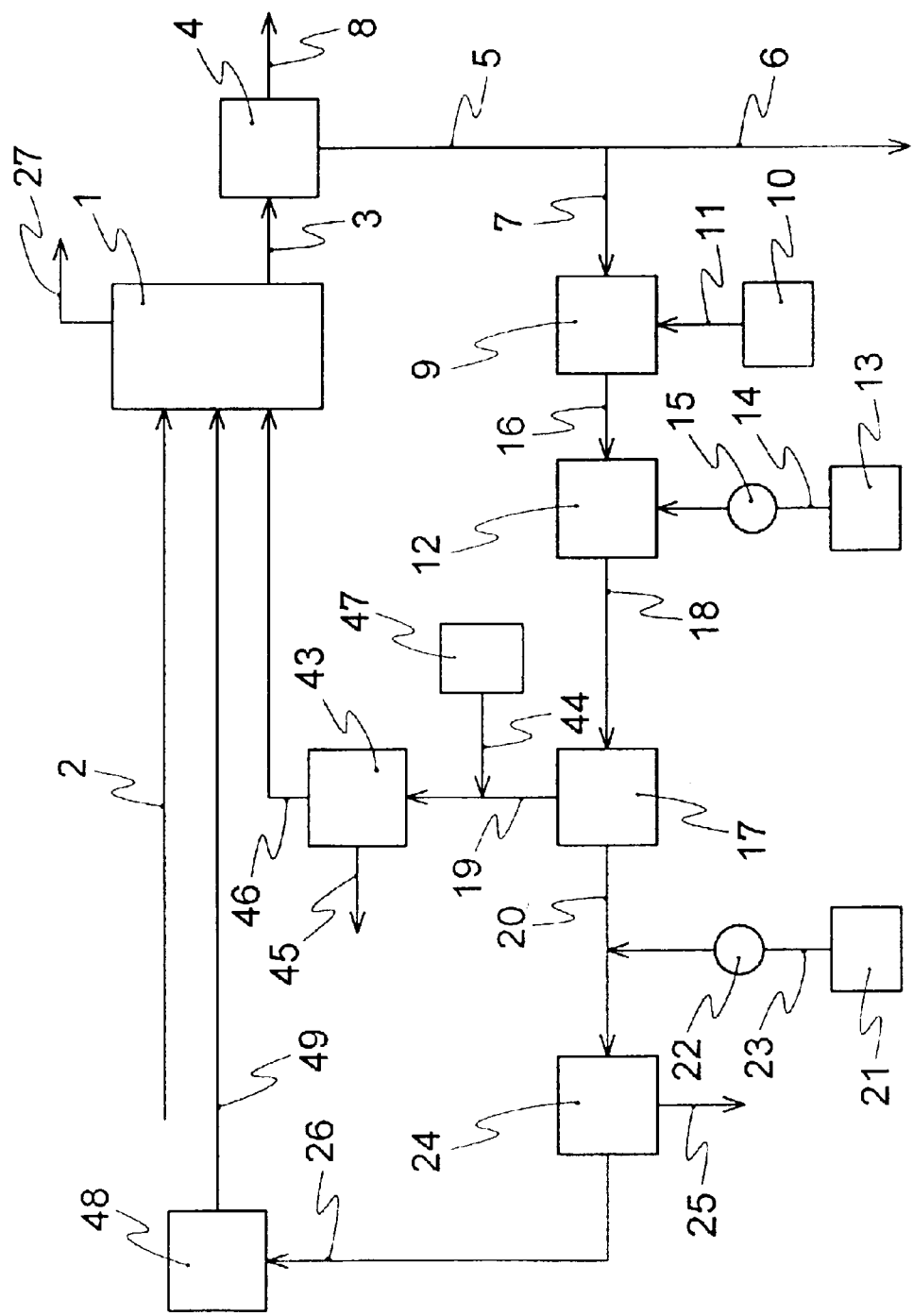
FIG. 27 is a diagram showing an apparatus embodying the present invention and a process flow of treating organic wastewater according to the present invention.

FIG. 27 is a diagram of an apparatus embodying the present invention and shows a process flow of treating organic wastewater with the apparatus. In the apparatus of the present embodiment shown in FIG. 27, the apparatus of Embodiment 5 shown in FIG. 15 is modified in such a way that rinse water supply conduit 44 connected to a rinse water storage tank 47 is connected to conduit 19 for feeding treated sludge and conduit 19 is connected to hydro-extractor 43. Hydro-extractor 43 is connected to anaerobic digestion tank 1 via conduit 46 for feeding rinsed sludge. Drain 45 for extracted water is also connected to hydro-extractor 43. Meanwhile, conduit 26 for feeding phosphorus removed water is connected to ion exchanger 48 and ion exchanger 48 is connected to anaerobic digestion tank 1 via conduit 49 for feeding ion exchanged water. Other than those above, the apparatus of the present embodiment conforms to that of Embodiment 5 shown in FIG. 15.

Hereinafter, workings of the apparatus according to the present embodiment are described.

As described in Embodiment 5, organic sludge from a water treatment plant, which is a mixture of raw sludge from a primary sedimentation tank and excess sludge from an aeration tank, is introduced into anaerobic digestion tank 1 and digested by microorganisms in anaerobic digestion tank 1. In this anaerobic digestion process, the thickened digested sludge in drain 5 is discharged through conduit 6 for disposing sludge, but part of the thickened digested sludge is introduced into ozonization tank 9 through conduit 7 and treated with ozone. Then, the thickened sludge treated with ozone is introduced into alkalization tank 12 and treated with alkali. Thereafter, the thickened sludge treated with alkali is separated into sludge solid component and sludge dissolved component in solid-liquid separation tank 17. The sludge solid component is introduced into hydro-extractor 43 via conduit 19. At the same time, biologically treated water in rinse water storage tank 47 is supplied through conduit 44 and mixed with the sludge solid component flowing through conduit 19. At hydro-extractor 43, the mixture is dehydrated so that soluble ions in the sludge solid component are removed therefrom, that is, the sludge solid component is rinsed. The rinsed sludge solid component is sent to anaerobic digestion tank 1 via conduit 46, while extracted water is discharged from drain 45. As for the sludge dissolved component, meanwhile, calcium carbonate solution is added by coagulant supply pump 22. The precipitate, i.e. calcium phosphate, is drawn out via conduit 25, while the remaining solution is introduced into ion exchanger 48 via conduit 26. In ion exchanger 48, ions in the sludge dissolved component are removed and, then, the sludge dissolved component is introduced into anaerobic digestion tank 1 via conduit 49 for ion exchanged water. Other than those above, the process of the present embodiment conforms to that of Embodiment 5.

With the combination of preceding ozone and succeeding alkali treatments according to the present embodiment, digested sludge from an anaerobic digestion tank is thickened and, then, synergistically affected by strong oxidation by ozone as well as decomposition by alkali. In other words, decomposition of organic substances by alkali treatment is highly enhanced by previously oxidizing the surface thereof with ozone. As a result of this synergistic effect, hardly soluble substances of solids in the thickened sludge, such as fibers and cell walls, can be denatured and converted into easily soluble substances which can be easily decomposed by the sludge in the anaerobic digestion tank. In addition, since dissolution of cell walls is enhanced with the above synergistic effect of preceding ozone and succeeding alkali treatments, phosphorus in solids of thickened sludge is efficiently eluted out. Therefore, solubility of sludge, yield of methane and the amount of eluted phosphorus are greatly increased in comparison to the effects of ozone treatment alone or alkali treatment alone and, further, the sum of the effects of these treatments.

Meanwhile, the sludge solid component separated in the solid-liquid separation tank may contain residue of sodium hydroxide from the alkali treatment and sodium ions inhibit the activity of the microorganisms for digestion. Accordingly, the operations of the anaerobic digestion tank may become unstable if such sludge solid component is introduced into the anaerobic digestion tank. Moreover, sludge dissolved component from which phosphorus is removed is preferably introduced into the anaerobic digestion tank to produce methane effectively, because sludge dissolved component contains a great deal of organic substances that are eluted out from the sludge through the treatments. However, since sodium ion concentration of the phosphorus removed sludge dissolved component is equal to or higher than that of the sludge solid component after the solid-liquid separation, introduction of such sludge dissolved component may also make the operations of the anaerobic digestion tank unstable. According to the present embodiment, therefore, the sludge solid component after solid-liquid separation is rinsed and the sludge dissolved component after phosphorus removal is ion-exchanged in order to remove sodium ions. Since the sludge solid component and the sludge dissolved component are introduced into the anaerobic digestion tank after removal of sodium ions, deactivation of the microorganisms by sodium ions hardly occurs and stable operation of the anaerobic digestion tank becomes possible.

Accordingly, more stable and efficient treatment of organic sludge, in which energy and resources are simultaneously recovered, is achieved by thickening the digested sludge from the anaerobic digestion tank, treating the thickened sludge with the process comprising preceding ozone and succeeding alkali treatments, separating into sludge solid component and sludge dissolved component, removing phosphorus from the sludge dissolved component, removing sodium ions from the sludge solid component and sludge dissolved component, and introducing the resulting solids and solution to the anaerobic digestion tank.

In the present embodiment, the sludge solid component is rinsed and the sludge dissolved component is ion-exchanged in order to remove sodium ions therefrom. However, another technique for removing ions, such as one utilizing a reverse osmosis membrane, may be applicable. Moreover, though the ion removal is conducted both for the sludge solid component after solid-liquid separation and sludge dissolved component after phosphorus removal in this embodiment, ions may be removed from either the sludge solid component after solid-liquid separation or the sludge dissolved component after phosphorus removal depending on the effects on the anaerobic digestion tank.

In the present embodiment, ions are removed from the sludge solid component and the sludge dissolved component and, then, the sludge solid component and the sludge dissolved component are introduced into the anaerobic digestion tank without further treatment. However, pH thereof may be adjusted to approximately neutral before the introduction to the anaerobic digestion tank as described in Embodiment 9 so that the effects of the present embodiment may be enhanced. Moreover, pH of the sludge solid component and/or sludge dissolved component may be adjusted in advance and then, ions are removed therefrom prior to the introduction to the anaerobic digestion tank.

Although biologically treated water is used for rinse water in the present embodiment, tap water, overflow effluent and rain water are also applicable.

Embodiment 18

Another apparatus embodying the present invention and a process of treating organic wastewater with the apparatus is described.

Figure 28:
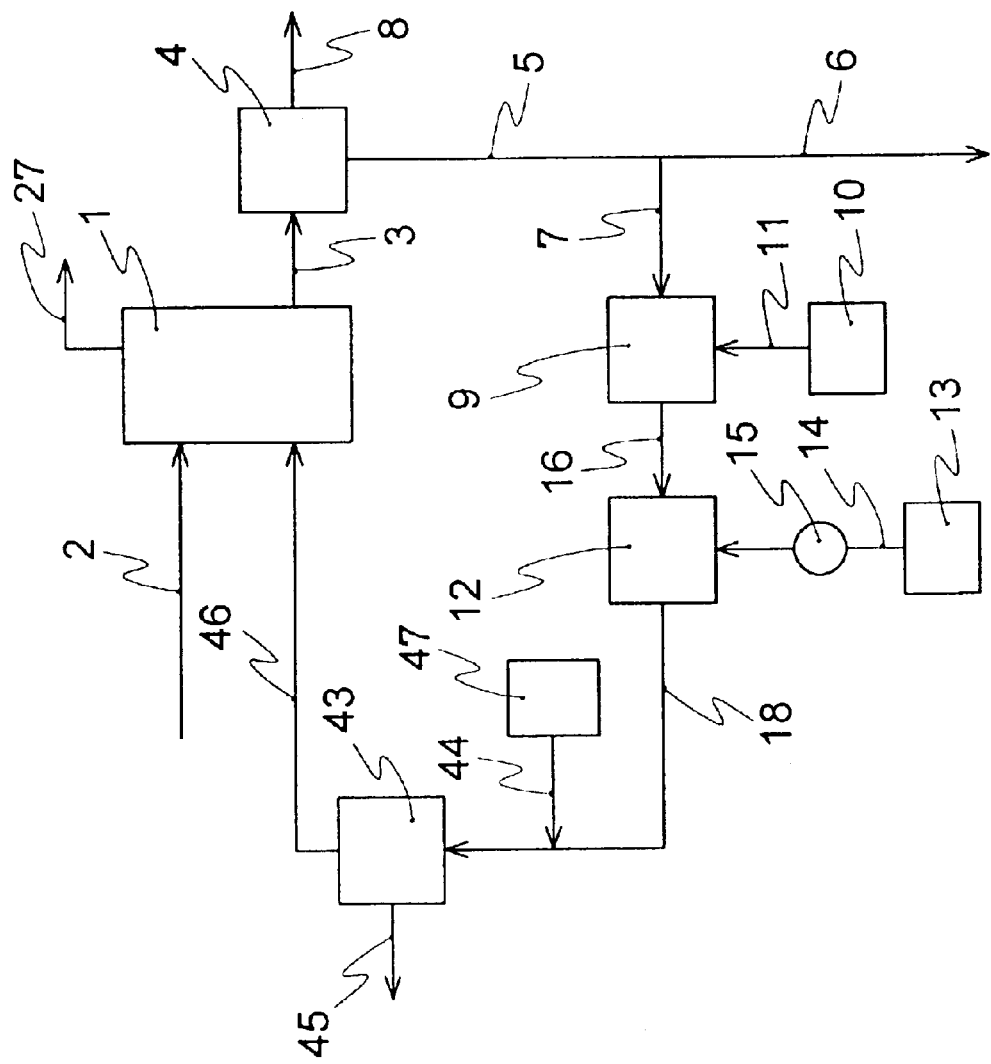
FIG. 28 is a diagram showing an apparatus embodying the present invention and a process flow of treating organic wastewater according to the present invention.

FIG. 28 is a diagram of an apparatus embodying the present invention and shows a process flow of treating organic wastewater with the apparatus. In the apparatus of the present embodiment shown in FIG. 28, components for recovering phosphorus are left out from the apparatus of Embodiment 17 shown in FIG. 27. More specifically, solid-liquid separation tank 17, conduit 19, drain 20, coagulant storage tank 21, coagulant supply pump 22, coagulant supply conduit 23, phosphorus recovery tank 24, conduit 25 for recovering phosphorus and conduit 26 for feeding phosphorus removed water are left out, rinse water supply conduit 44 connected to rinse water storage tank 47 is connected to drain 18 for alkali treated sludge and the drain 18 is connected to the hydro-extractor 43. Other than those above, the apparatus of the present embodiment conforms to that of Embodiment 17 shown in FIG. 27.

Hereinafter, workings of the apparatus according to the present embodiment are described.

As described in Embodiment 17, organic sludge from a water treatment plant, which is a mixture of raw sludge from a primary sedimentation tank and excess sludge from an aeration tank, is introduced into anaerobic digestion tank 1 and digested by microorganisms in anaerobic digestion tank 1. In this anaerobic digestion process, the thickened digested sludge in drain 5 is discharged through conduit 6 for disposing sludge, but part of the thickened digested sludge is introduced into ozonization tank 9 through the conduit 7 and treated with ozone. Then, the thickened sludge treated with ozone is introduced into alkalization tank 12 and treated with alkali. Thereafter, the thickened sludge treated with alkali is sent to hydro-extractor 43 via drain 18. At the same time, biologically treated water in rinse water storage tank 47 is supplied through conduit 44 and mixed with the thickened sludge flowing through drain 18. In hydro-extractor 43, the mixture is dehydrated so that soluble ions in the solids of the thickened sludge are removed therefrom, that is, the thickened sludge is rinsed. The rinsed thickened sludge is sent to anaerobic digestion tank 1 via conduit 46, while extracted water is discharged from drain 45. Other than those above, the process of the present embodiment conforms to that of Embodiment 17.

The present embodiment is preferable when thickened sludge contains little phosphorus and recovering energy from the sludge is a priority. With the above described combination of preceding ozone and succeeding alkali treatments according to the present embodiment, digested sludge from an anaerobic digestion tank is thickened and, then, synergistically affected by strong oxidation by ozone as well as decomposition by alkali. In other words, decomposition of organic substances by alkali treatment is highly enhanced by oxidizing the surface thereof with ozone prior to alkali treatment. As a result of this synergistic effects, hardly soluble substances of solids in thickened sludge, such as fibers and cell walls, can be denatured and converted into easily soluble substances which can be easily decomposed by the sludge in the anaerobic digestion tank. This improvement in solubilization is much greater than that obtained with ozone treatment alone or alkali treatment alone and, importantly, greater than the sum of these improvements so yield of methane is greatly improved and sludge to be disposed is greatly reduced.

Meanwhile, the thickened sludge may contain residue of sodium hydroxide from the alkali treatment and sodium ions inhibit the activity of the microorganisms for digestion. Accordingly, the operations of the anaerobic digestion tank may become unstable if such thickened sludge is introduced into the anaerobic digestion tank. According to the present embodiment, therefore, the thickened sludge after alkali treatment is rinsed in order to remove sodium ions. Since the thickened sludge is introduced into the anaerobic digestion tank after removal of sodium ions, deactivation of the microorganisms by sodium ions hardly occurs and stable operation of the anaerobic digestion tank becomes possible.

In the present embodiment, ions are removed from the thickened sludge and, then, the thickened sludge is introduced into the anaerobic digestion tank without further treatment. However, pH of the thickened sludge may be adjusted to approximately neutral before the introduction to the anaerobic digestion tank as described in Embodiment 10 so that the effects of the present embodiment may be enhanced. Moreover, pH of the thickened sludge may be adjusted in advance and then, ions are removed from the thickened sludge prior to the introduction to the anaerobic digestion tank.

Although biologically treated water is used for rinse water in the present embodiment, tap water, overflow effluent and rain water are also applicable.

Embodiment 19

Another apparatus embodying the present invention and a process of treating organic wastewater with the apparatus is described.

Figure 29:
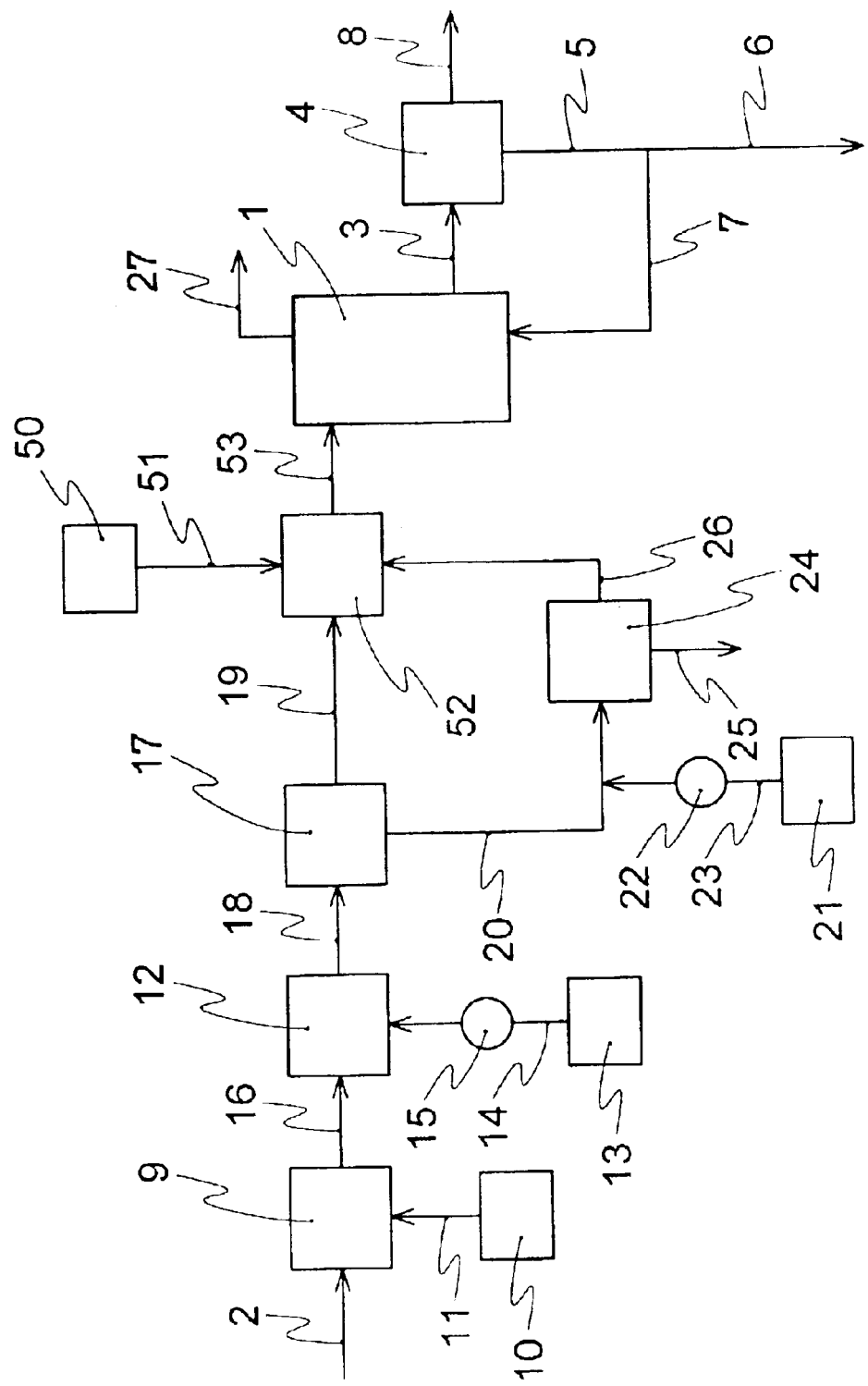
FIG. 29 is a diagram showing an apparatus embodying the present invention and a process flow of treating organic wastewater according to the present invention.

FIG. 29 is a diagram of an apparatus embodying the present invention and shows a process flow of treating organic wastewater with the apparatus. In the apparatus of the present embodiment shown in FIG. 29, the apparatus of Embodiment 1 shown in FIG. 11 is modified in such a way that the conduit 19 for feeding treated sludge and conduit 26 for feeding phosphorus removed water are connected to dilution tank 52 and dilution tank 52 is connected to anaerobic digestion tank 1 via conduit 53 for feeding diluted sludge. Moreover, diluent water supply conduit 51 is provided and connects diluent water storage tank 50 to dilution tank 52. Other than those above, the apparatus of the present embodiment conforms to that of Embodiment 1 shown in FIG. 11.

Hereinafter, workings of the apparatus according to the present embodiment are described.

As described in Embodiment 1, organic sludge from a water treatment plant, which is a mixture of raw sludge from a primary sedimentation tank and excess sludge from an aeration tank, is introduced into the ozonization tank 9 via conduit 2 and treated with ozone. The organic sludge treated with ozone is introduced into alkalization tank 12 and treated with alkali. The organic sludge treated with alkali is sent to solid-liquid separation tank 17 and separated into sludge solid component and sludge dissolved component. The sludge solid component is introduced into dilution tank 52 via conduit 19. As for the sludge dissolved component, meanwhile, calcium carbonate solution is added by coagulant supply pump 22. The precipitate, i.e. calcium phosphate, is drawn out via conduit 25, while the remaining solution is introduced into dilution tank 52 via conduit 26. In dilution tank 52, the mixture, which comprises the sludge solid component and the sludge dissolved component where phosphorus is removed, is diluted by injecting biologically treated water stored in diluent water storage tank 50 through supply conduit 51 so that the concentration of soluble ion in the mixture is lowered. Thereafter, the diluted mixture is introduced into anaerobic digestion tank 1 via conduit 53 for feeding diluted sludge. Other than those above, the process of the present embodiment conforms to that of Embodiment 1.

With the combination of preceding ozone and succeeding alkali treatments according to the present embodiment, organic sludge is synergistically affected by strong oxidation by ozone as well as decomposition with alkali. In other words, decomposition of organic substances by alkali treatment is highly enhanced by oxidizing the surface thereof with ozone prior to alkali treatment. As a result of this synergistic effect, hardly soluble substances of solids in organic sludge, such as fibers and cell walls, can be denatured and converted into easily soluble substances which can be easily decomposed by the sludge in the anaerobic digestion tank. In addition, since dissolution of cell walls is enhanced with the above synergistic effect of preceding ozone and succeeding alkali treatments, phosphorus in solids of organic sludge is efficiently eluted out. Therefore, solubility of sludge, yield of methane and the amount of eluted phosphorus are greatly increased in comparison to the effects of ozone treatment alone or alkali treatment alone and, further, the sum of the effects of these treatments.

Meanwhile, the sludge solid component separated in the solid-liquid separation tank after alkaline treatment may contain residue of sodium hydroxide from the alkali treatment and sodium ions inhibit the activity of the microorganisms for digestion. Accordingly, the operations of the anaerobic digestion tank may become unstable if such sludge solid component is introduced into the anaerobic digestion tank. Moreover, sludge dissolved component from which phosphorus is removed is preferably introduced into the anaerobic digestion tank to produce methane effectively, because sludge dissolved component contains a great deal of organic substances that are eluted out from the sludge through the treatments. However, since sodium ion concentration of the phosphorus removed sludge dissolved component is equal to or higher than that of the sludge solid component after the solid-liquid separation, introduction of such sludge dissolved component may also make the operations of the anaerobic digestion tank unstable. According to the present embodiment, therefore, the sludge solid component after solid-liquid separation and the sludge dissolved component after phosphorus removal are diluted by adding biologically treated water so that sodium ion concentration thereof is lowered. Since the sludge solid component and the sludge dissolved component of lower sodium ion concentration are introduced into the anaerobic digestion tank, deactivation of the microorganisms by sodium ions hardly occurs and stable operation of the anaerobic digestion tank becomes possible.

Accordingly, more stable and efficient treatment of organic sludge, in which energy and resources are simultaneously recovered, is achieved by the process of the present embodiment comprising preceding ozone and succeeding alkali treatments, separation into sludge solid component and sludge dissolved component, phosphorus removal from the sludge dissolved component, dilution of sodium ion in the sludge solid component and sludge dissolved component, and introduction to the anaerobic digestion tank.

In the present embodiment, the separated sludge solid component and the sludge dissolved component from which phosphorus is removed are mixed and the mixture is diluted to lower the sodium ion concentration. However, the sludge solid component and the sludge dissolved component may be diluted independently and then introduced to the anaerobic digestion tank. Moreover, depending on the effects on the anaerobic digestion tank, either the sludge solid component or the sludge dissolved component may be diluted.

In the present embodiment, the sludge solid component and the sludge dissolved component from which phosphorus is removed are diluted and, then, introduced into the anaerobic digestion tank without further treatment. However, pH thereof may be adjusted to approximately neutral before the introduction to the anaerobic digestion tank as described in Embodiment 7 so that the effects of the present embodiment may be enhanced. Moreover, pH of the sludge solid com ponent and/or sludge dissolved component may be adjusted in advance and then, diluted prior to the introduction to the anaerobic digestion tank.

Although biologically treated water is used for diluent water in the present embodiment, tap water, overflow effluent and rain water are also applicable.

Embodiment 20

Another apparatus embodying the present invention and a process of treating organic wastewater with the apparatus is described.

Figure 30:
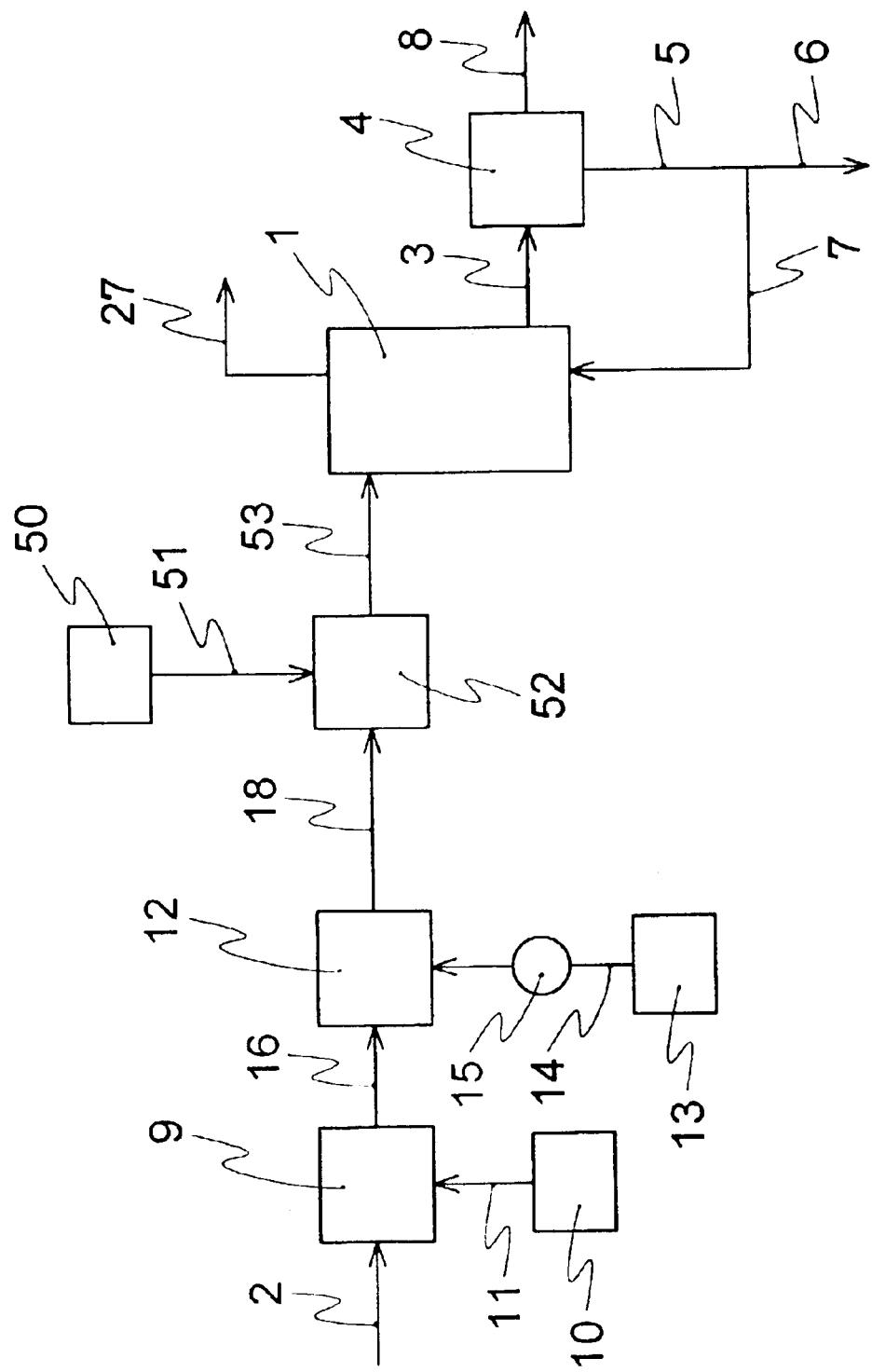
FIG. 30 is a diagram showing an apparatus embodying the present invention and a process flow of treating organic wastewater according to the present invention.

FIG. 30 is a diagram of an apparatus embodying the present invention and shows a process flow of treating organic wastewater with the apparatus. In the apparatus of the present embodiment shown in FIG. 30, components for recovering phosphorus are left out from the apparatus of Embodiment 19 shown in FIG. 29. More specifically, solid-liquid separation tank 17, conduit 19, drain 20, coagulant storage tank 21, coagulant supply pump 22, coagulant supply conduit 23, phosphorus recovery tank 24, conduit 25 for recovering phosphorus and conduit 26 for feeding phosphorus removed water are left out and drain 18 is connected to dilution tank 52. Other than those above, the apparatus of the present embodiment conforms to that of Embodiment 19 shown in FIG. 29.

Hereinafter, workings of the apparatus according to the present embodiment are described.

As described in Embodiment 19, organic sludge from a water treatment plant, which is a mixture of raw sludge from a primary sedimentation tank and excess sludge from an aeration tank, is introduced into ozonization tank 9 via conduit 2 and treated with ozone. The organic sludge treated with ozone is introduced into alkalization tank 12 and treated with alkali. The organic sludge treated with alkali is sent to dilution tank 52 via drain 18 for alkali treated sludge. In dilution tank 52, the organic sludge treated with ozone and alkali is diluted by injecting biologically treated water stored in diluent water storage tank 50 through supply conduit 51 so that the concentration of soluble ion in the organic sludge is lowered. Thereafter, the diluted sludge is introduced into anaerobic digestion tank 1 via conduit 53 for feeding diluted sludge. Other than those above, the process of the present embodiment conforms to that of Embodiment 19.

The present embodiment is preferable when organic sludge contains little phosphorus and recovering energy from the sludge is a priority. With the above described combination of preceding ozone and succeeding alkali treatments according to the present embodiment, organic sludge is synergistically affected by strong oxidation by ozone and decomposition by alkali. In other words, decomposition of organic substances by alkali treatment is highly enhanced by oxidizing the surface thereof with ozone prior to alkali treatment. As a result of this synergistic effect, hardly soluble substances of solids in organic sludge, such as fibers and cell walls, can be denatured and converted into easily soluble substances which can be easily decomposed by the sludge in the anaerobic digestion tank. This improvement in solubilization is much greater than that obtained with ozone treatment alone or alkali treatment alone and, importantly, greater than the sum of these improvements so yield of methane is greatly improved and sludge to be disposed is greatly reduced.

Meanwhile, the organic sludge may contain residue of sodium hydroxide from the alkali treatment and sodium ions inhibit the activity of the microorganisms for digestion.

Accordingly, the operations of the anaerobic digestion tank may become unstable if such organic sludge is introduced into the anaerobic digestion tank. According to the present embodiment, therefore, the organic sludge after alkali treatment is diluted by adding biologically treated water so that sodium ion concentration thereof is lowered. Since the organic sludge of lower sodium ion concentration is introduced into the anaerobic digestion tank, deactivation of the microorganisms by sodium ions hardly occurs and stable operation of the anaerobic digestion tank becomes possible.

In the preset embodiment, the organic sludge is diluted and then, introduced into the anaerobic digestion tank without further treatment. However, pH thereof may be adjusted to approximately neutral before the introduction to the anaerobic digestion tank as described in Embodiment 8 so that the effects of the present embodiment may be enhanced. Moreover, pH of the organic sludge may be adjusted in advance, the organic sludge is diluted in order to decrease the sodium ion concentration prior to the introduction to the anaerobic digestion tank.

Although biologically treated water is used for diluent water in the present embodiment, tap water, overflow effluent and rain water are also applicable.

Embodiment 21

Another apparatus embodying the present invention and a process of treating organic wastewater with the apparatus is described. In Embodiment 19, influent organic wastewater is treated with ozone and successively with alkali and then introduced into an anaerobic digestion tank after the concentration of the inhibitor against anaerobic digestion is lowered. In the present embodiment, meanwhile, digested sludge from an anaerobic digestion tank is treated with ozone and successively with alkali and then introduced into the anaerobic digestion tank after the concentration of the inhibitor against anaerobic digestion is lowered.

Figure 31:
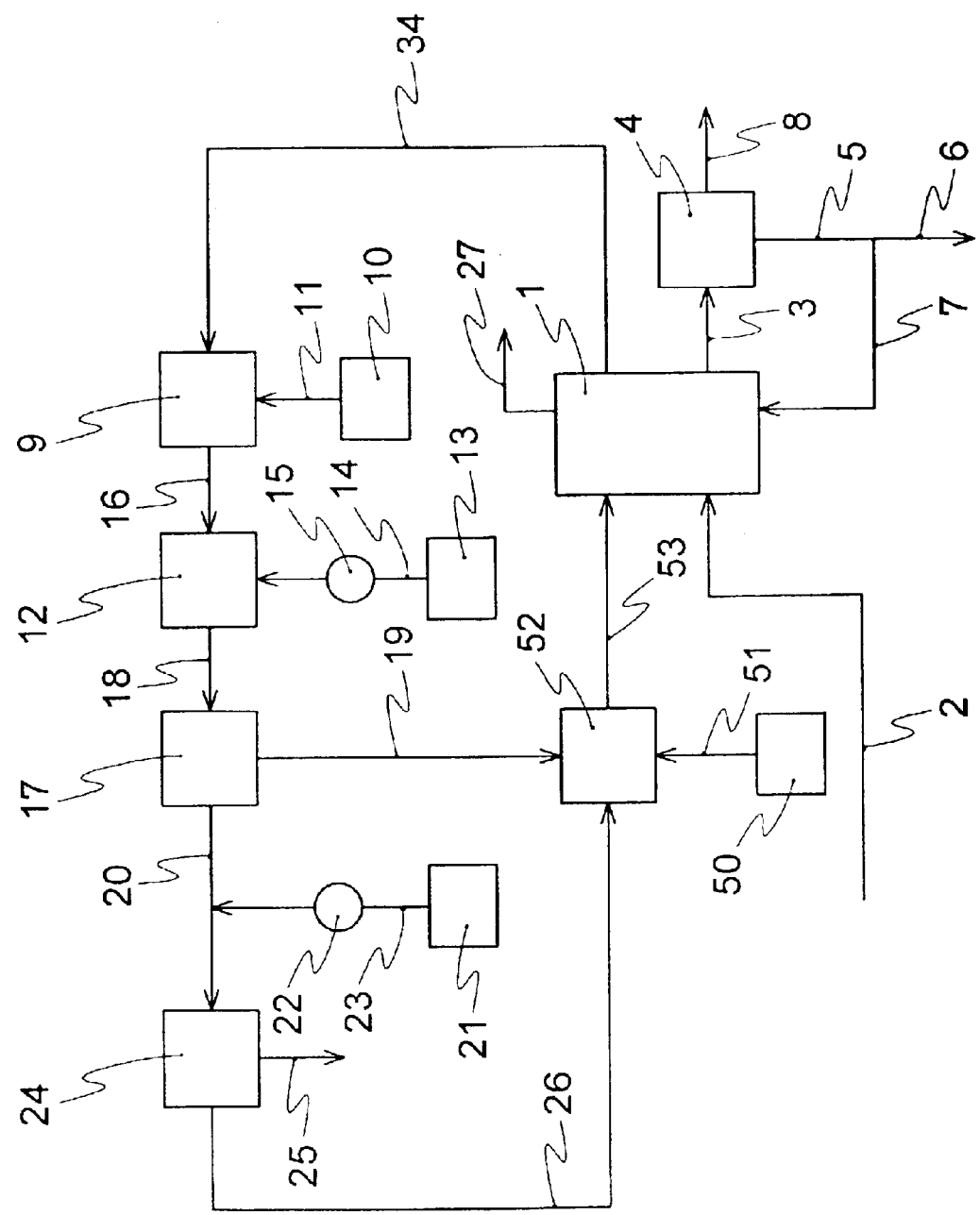
FIG. 31 is a diagram showing an apparatus embodying the present invention and a process flow of treating organic wastewater according to the present invention.

FIG. 31 is a diagram of an apparatus embodying the present invention and shows a process flow of treating organic wastewater with the apparatus. In the apparatus of the present embodiment shown in FIG. 31, the apparatus of Embodiment 3 shown in FIG. 13 is modified in such a way that conduit 19 for feeding treated sludge and conduit 26 for feeding phosphorus removed water are connected to dilution tank 52 and dilution tank 52 is connected to anaerobic digestion tank 1 via conduit 53 for feeding diluted sludge. Moreover, diluent water supply conduit 51 is provided and connects diluent water storage tank 50 to dilution tank 52. Other than those above, the apparatus of the present embodiment conforms to that of Embodiment 3 shown in FIG. 13.

Hereinafter, workings of the apparatus according to the present embodiment are described.

As described in Embodiment 3, organic sludge from a water treatment plant, which is a mixture of raw sludge from a primary sedimentation tank and excess sludge from an aeration tank, is introduced into the anaerobic digestion tank 1 and digested by microorganisms in the anaerobic digestion tank 1. In this anaerobic digestion process, the digested sludge inside the anaerobic digestion tank 1 is introduced into ozonization tank 9 through conduit 34 and treated with ozone. Then, the digested sludge treated with ozone is introduced into alkalization tank 12 and treated with alkali. Thereafter, the digested sludge treated with alkali is separated into sludge solid component and sludge dissolved component in solid-liquid separation tank 17. The sludge solid component is introduced into dilution tank 52 via conduit 19. As for the sludge dissolved component, meanwhile, calcium carbonate solution is added by coagulant supply pump 22. The precipitate, i.e. calcium phosphate, is drawn out via conduit 25, while the remaining solution is introduced into dilution tank 52 via conduit 26. In dilution tank 52, the mixture, which comprises the sludge solid component and the sludge dissolved component from which phosphorus is removed, is diluted by injecting biologically treated water stored in diluent water storage tank 50 through supply conduit 51 so that the concentration of soluble ion in the mixture is lowered. Thereafter, the diluted mixture is introduced into anaerobic digestion tank 1 via conduit 53 for feeding diluted sludge. Other than those above, the process of the present embodiment conforms to that of Embodiment 3.

With the combination of preceding ozone and succeeding alkali treatments according to the present embodiment, digested sludge from an anaerobic digestion tank is synergistically affected by strong oxidation by ozone as well as decomposition by alkali. In other words, decomposition of organic substances by alkali treatment is highly enhanced by oxidizing the surface thereof with ozone prior to alkali treatment. As a result of this synergistic effect, hardly soluble substances of solids in digested sludge, such as fibers and cell walls, can be denatured and converted into easily soluble substances which can be easily decomposed by the sludge in the anaerobic digestion tank. In addition, since dissolution of cell walls is enhanced with the above synergistic effect of preceding ozone and succeeding alkali treatments, phosphorus in solids of digested sludge is efficiently eluted out. Therefore, solubility of sludge, yield of methane and the amount of eluted phosphorus are greatly increased in comparison to the effects of ozone treatment alone or alkali treatment alone and, further, the sum of the effects of these treatments.

Meanwhile, the sludge solid component separated in the solid-liquid separation tank may contain residue of sodium hydroxide from the alkali treatment and sodium ions inhibit the activity of the microorganisms for digestion. Accordingly, the operations of the anaerobic digestion tank may become unstable if such sludge solid component is introduced into the anaerobic digestion tank. Moreover, sludge dissolved component in which phosphorus is removed is preferably introduced into the anaerobic digestion tank to produce methane effectively, because sludge dissolved component contains a great deal of organic substances that are eluted out from the sludge through the treatments. However, since the sodium ion concentration of the phosphorus removed sludge dissolved component is equal to or higher than that of the sludge solid component after the solid-liquid separation, introduction of such sludge dissolved component may also make the operations of the anaerobic digestion tank unstable. According to the present embodiment, therefore, the sludge solid component after solid-liquid separation and the sludge dissolved component after phosphorus removal are diluted by adding biologically treated water so that sodium ion concentration thereof is lowered. Since the sludge solid component and the sludge dissolved component of lower sodium ion concentration are introduced into the anaerobic digestion tank, deactivation of the microorganisms by sodium ions hardly occurs and stable operation of the anaerobic digestion tank becomes possible.

Accordingly, more stable and efficient treatment of organic sludge, in which energy and resources are simultaneously recovered, is achieved by treating the digested sludge from the anaerobic digestion tank with the process comprising preceding ozone and succeeding alkali treatments, separation into sludge solid component and sludge dissolved component, phosphorus removal from the sludge dissolved component, dilution of sodium ion concentration in the sludge solid component and sludge dissolved component, and introduction to the anaerobic digestion tank.

In the present embodiment, the separated sludge solid component and the separated sludge dissolved component from which phosphorus is removed are mixed and the mixture is diluted to lower sodium ion concentration. However, the sludge solid component and the sludge dissolved component are diluted independently to decrease the sodium ion concentration before the introduction to the anaerobic digestion tank. Moreover, though the separated sludge solid component and the separated sludge dissolved component from which phosphorus is removed are mixed and the both were diluted in this embodiment, either the sludge solid component or the sludge dissolved component may be diluted depending on the effects on the anaerobic digestion tank.

In the present embodiment, the separated sludge solid component and the separated sludge dissolved component from which phosphorus is removed are diluted and then introduced into the anaerobic digestion tank without further treatment. However, pH thereof may be adjusted to approximately neutral before the introduction to the anaerobic digestion tank as described in Embodiment 9 so that the effects of the present embodiment may be enhanced. Moreover, pH of the sludge solid component and/or sludge dissolved component may be adjusted in advance and then diluted in order to decrease the sodium ion concentration prior to the introduction to the anaerobic digestion tank.

Although biologically treated water is used for diluent water in the present embodiment, tap water, overflow effluent and rain water are also applicable.

Embodiment 22

Another apparatus embodying the present invention and a process of treating organic wastewater with the apparatus is described.

Figure 32:
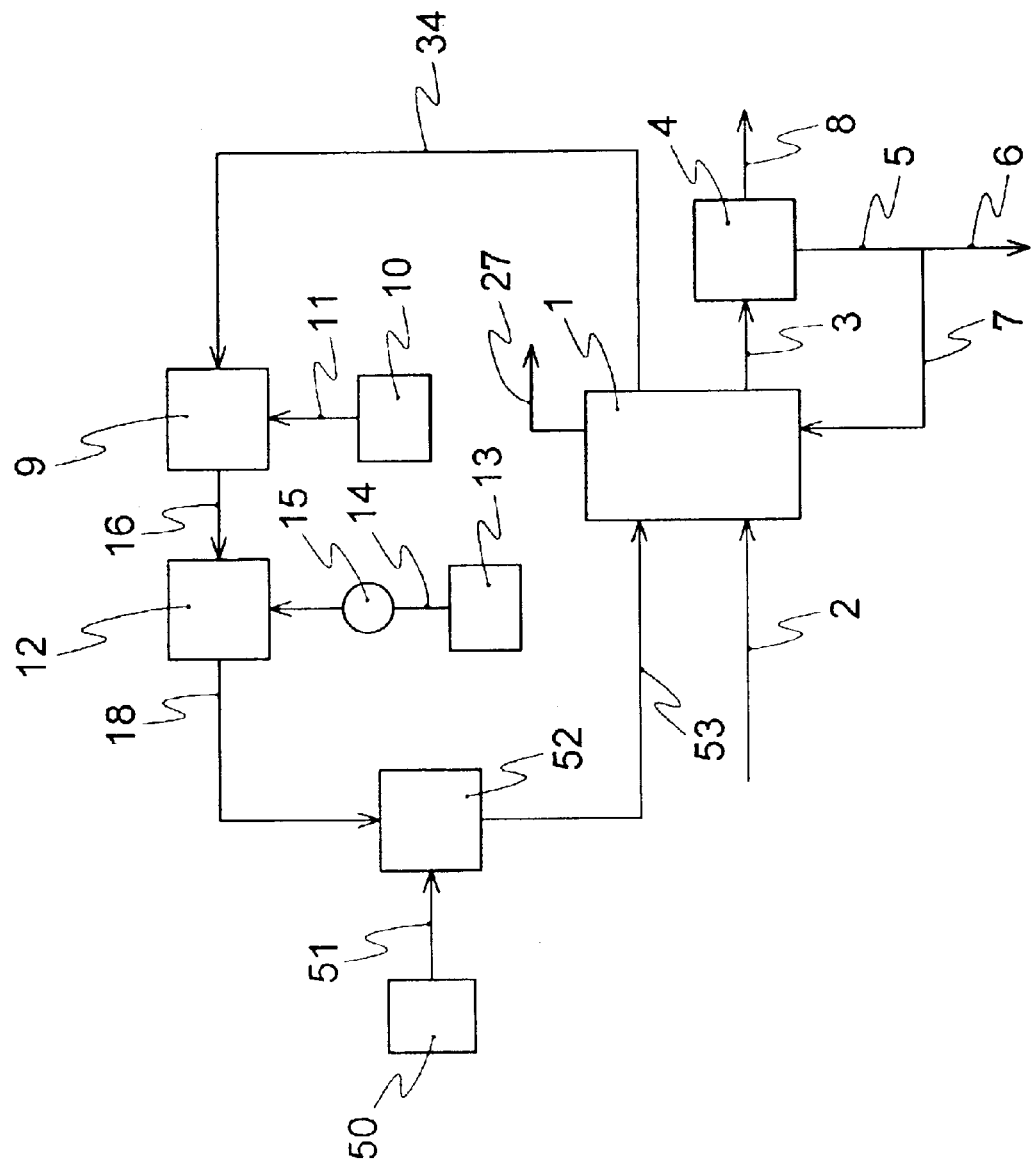
FIG. 32 is a diagram showing an apparatus embodying the present invention and a process flow of treating organic wastewater according to the present invention.

FIG. 32 is a diagram of an apparatus embodying the present invention and shows a process flow of treating organic wastewater with the apparatus. In the apparatus of the present embodiment shown in FIG. 32, components for recovering phosphorus are left out from the apparatus of Embodiment 21 shown in FIG. 31. More specifically, solid-liquid separation tank 17, conduit 19, drain 20, coagulant storage tank 21, coagulant supply pump 22, coagulant supply conduit 23, phosphorus recovery tank 24, conduit 25 for recovering phosphorus and conduit 26 for feeding phosphorus removed water are left out and drain 18 is connected to dilution tank 52. Other than those above, the apparatus of the present embodiment conforms to that of Embodiment 21 shown in FIG. 31.

Hereinafter, workings of the apparatus according to the present embodiment are described.

As described in Embodiment 21, organic sludge from a water treatment plant, which is a mixture of raw sludge from a primary sedimentation tank and excess sludge from an aeration tank, is introduced into the anaerobic digestion tank 1 and digested by microorganisms in anaerobic digestion tank 1. In this anaerobic digestion process, the digested sludge inside anaerobic digestion tank 1 is introduced into the ozonization tank 9 through conduit 34 and treated with ozone. Then, the digested sludge treated with ozone is introduced into alkalization tank 12 and treated with alkali. The digested sludge treated with alkali is sent to dilution tank 52 via drain 18 for alkali treated sludge. In dilution tank 52, the digested sludge treated with ozone and alkali is diluted by injecting biologically treated water stored in diluent water storage tank 50 through supply conduit 51 so that concentration of soluble ion in the digested sludge is lowered. Thereafter, the diluted sludge is introduced into anaerobic digestion tank 1 via conduit 53 for feeding diluted sludge. Other than those above, the process of the present embodiment conforms to that of Embodiment 21.

The present embodiment is preferable when digested sludge contains little phosphorus and recovering energy from the sludge is a priority. With the above described combination of preceding ozone and succeeding alkali treatments according to the present embodiment, digested sludge from an anaerobic digestion tank is synergistically affected by strong oxidation by ozone and decomposition by alkali. In other words, decomposition of organic substances by alkali treatment is highly enhanced by oxidizing the surface thereof with ozone prior to alkali treatment. As a result of this synergistic effect, hardly soluble substances of solids in digested sludge, such as fibers and cell walls, can be denatured and converted into easily soluble substances which can be easily decomposed by sludge in the anaerobic digestion tank. This improvement in solubilization is much greater than that obtained with ozone treatment alone or alkali treatment alone and, importantly, greater than the sum of these improvements so yield of methane is greatly improved and sludge to be disposed is greatly reduced.

Meanwhile, the digested sludge may contain residue of sodium hydroxide from the alkali treatment and sodium ions inhibit the activity of the microorganisms for digestion. Accordingly, the operations of the anaerobic digestion tank may become unstable if such digested sludge is introduced into the anaerobic digestion tank. According to the present embodiment, therefore, the digested sludge after alkali treatment is diluted by adding biologically treated water so that sodium ion concentration thereof is lowered. Since the digested sludge of lower sodium ion concentration is introduced into the anaerobic digestion tank, deactivation of the microorganisms by sodium ions hardly occurs and stable operation of the anaerobic digestion tank becomes possible.

In the preset embodiment, the digested sludge is diluted and then introduced into the anaerobic digestion tank without further treatment. However, pH thereof may be adjusted to approximately neutral before the introduction to the anaerobic digestion tank as described in Embodiment 10 so that the effects of the present embodiment may be enhanced. Moreover, pH of the digested sludge may be adjusted in advance and, then, the digested sludge is diluted to decrease the sodium ion concentration prior to the introduction to the anaerobic digestion tank.

Although biologically treated water is used for diluent water in the present embodiment, tap water, overflow effluent and rain water are also applicable.

Embodiment 23

Another apparatus embodying the present invention and a process of treating organic wastewater with the apparatus is described. In Embodiment 19, influent organic wastewater is treated with ozone and successively with alkali and then introduced into an anaerobic digestion tank after the concentration of the inhibitor against anaerobic digestion is lowered. In Embodiment 21, digested sludge from an anaerobic digestion tank is treated with ozone and successively with alkali and then introduced into the anaerobic digestion tank after the concentration of the inhibitor against anaerobic digestion is lowered. In the present embodiment, meanwhile, digested sludge is thickened through solid-liquid separation, the thickened digested sludge is treated with ozone and successively with alkali and then introduced into the anaerobic digestion tank after the concentration of the inhibitor against anaerobic digestion is lowered.

Figure 33:
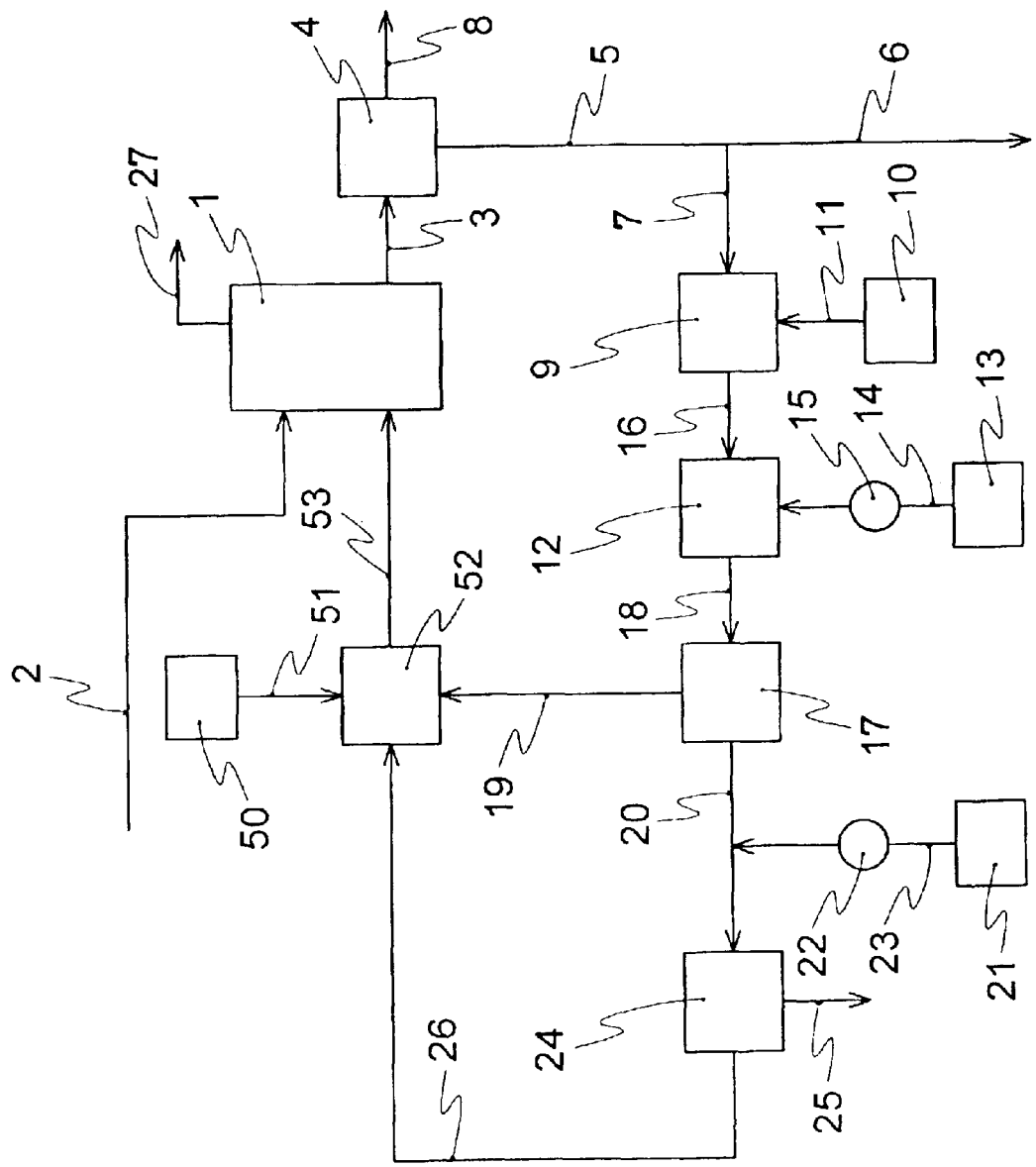
FIG. 33 is a diagram showing an apparatus embodying the present invention and a process flow of treating organic wastewater according to the present invention.

FIG. 33 is a diagram of an apparatus embodying the present invention and shows a process flow of treating organic wastewater with the apparatus. In the apparatus of the present embodiment shown in FIG. 33, the apparatus of Embodiment 5 shown in FIG. 15 is modified in such a way that conduit 19 for feeding treated sludge and conduit 26 for feeding phosphorus removed water are connected to dilution tank 52 and dilution tank 52 is connected to the anaerobic digestion tank 1 via conduit 53 for feeding diluted sludge. Moreover, diluent water supply conduit 51 is provided and connects diluent water storage tank 50 to the dilution tank 52. Other than those above, the apparatus of the present embodiment conforms to that of Embodiment 5 shown in FIG. 15.

Hereinafter, workings of the apparatus according to the present embodiment are described.

As described in Embodiment 5, organic sludge from a water treatment plant, which is a mixture of raw sludge from a primary sedimentation tank and excess sludge from an aeration tank, is introduced into anaerobic digestion tank 1 and digested by microorganisms in anaerobic digestion tank 1. In this anaerobic digestion process, the thickened digested sludge in drain 5 is discharged through conduit 6 for disposing sludge, but part of the thickened digested sludge is introduced into the ozonization tank 9 through conduit 7 and treated with ozone. Then, the thickened sludge treated with ozone is introduced into the alkalization tank 12 and treated with alkali. Thereafter, the thickened sludge treated with alkali is separated into sludge solid component and sludge dissolved component at solid-liquid separation tank 17. The sludge solid component is introduced into dilution tank 52 via conduit 19. As for the sludge dissolved component, meanwhile, calcium carbonate solution is added by the coagulant supply pump 22. The precipitate, i.e. calcium phosphate, is drawn out via conduit 25, while the remaining solution is introduced into dilution tank 52 via conduit 26. In dilution tank 52, the mixture, which comprises the sludge solid component and the sludge dissolved component from which phosphorus is removed, is diluted by injecting biologically treated water stored in diluent water storage tank 50 through supply conduit 51 so that the concentration of the soluble ion in the mixture is lowered. Thereafter, the diluted mixture is introduced into anaerobic digestion tank 1 via conduit 53 for feeding diluted sludge. Other than those above, the process of the present embodiment conforms to that of Embodiment 5.

With the combination of preceding ozone and succeeding alkali treatments according to the present embodiment, digested sludge from an anaerobic digestion tank is thickened and then synergistically affected by strong oxidation by ozone as well as decomposition by alkali. In other words, decomposition of organic substances by alkali treatment is highly enhanced by oxidizing the surface thereof with ozone prior to alkali treatment. As a result of this synergistic effect, hardly soluble substances of solids in the thickened sludge, such as fibers and cell walls, can be denatured and converted into easily soluble substances which can be easily decomposed by the sludge in the anaerobic digestion tank. In addition, since dissolution of cell walls is enhanced with the above synergistic effect of preceding ozone and succeeding alkali treatments, phosphorus in solids of thickened sludge is efficiently eluted out. Therefore, solubility of sludge, yield of methane and the amount of eluted phosphorus are greatly increased in comparison to the effects of ozone treatment alone or alkali treatment alone and, further, the sum of the effects of these treatments.

Meanwhile, the sludge solid component separated in the solid-liquid separation tank after alkali treatment may contain residue of sodium hydroxide from the alkali treatment and sodium ions inhibit the activity of the microorganisms for digestion. Accordingly, the operations of the anaerobic digestion tank may become unstable if such sludge solid component is introduced into the anaerobic digestion tank. Moreover, sludge dissolved component from which phosphorus is removed is preferably introduced into the anaerobic digestion tank to produce methane effectively, because the sludge dissolved component contains a great deal of organic substances that are eluted out from the sludge through the treatments. However, since the sodium ion concentration of the phosphorus removed sludge dissolved component is equal to or higher than that of the sludge solid component after the solid-liquid separation, introduction of such sludge dissolved component may also make the operations of the anaerobic digestion tank unstable. According to the present embodiment, therefore, the sludge solid component after solid-liquid separation and the sludge dissolved component after phosphorus removal are diluted by adding biologically treated water so that sodium ion concentration thereof is lowered. Since the sludge solid component and the sludge dissolved component of lower sodium ion concentration are introduced into the anaerobic digestion tank, deactivation of the microorganisms by sodium ions hardly occurs and stable operation of the anaerobic digestion tank becomes possible.

Accordingly, more stable and efficient treatment of organic sludge, in which energy and resources are simultaneously recovered, is achieved by thickening the digested sludge from the anaerobic digestion tank and treating the thickened sludge with the process comprising preceding ozone and succeeding alkali treatments, separation into sludge solid component and sludge dissolved component, phosphorus removal from the sludge dissolved component, dilution of sodium ion concentration in the sludge solid component and sludge dissolved component, and introduction to the anaerobic digestion tank.

In the present embodiment, the separated sludge solid component and the sludge dissolved component from which phosphorus is removed are mixed and the mixture is diluted to lower sodium ion concentration. However, the separated sludge solid component and the separated sludge dissolved component from which phosphorus is removed are diluted independently to decrease the sodium ion concentration before the introduction to the anaerobic digestion tank. Moreover, depending on the effects on the anaerobic digestion tank, either the sludge solid component or the sludge dissolved component may be diluted.

In the preset embodiment, the sludge solid component and the sludge dissolved component are diluted and then introduced into the anaerobic digestion tank without further treatment. However, pH thereof may be adjusted to approximately neutral before the introduction to the anaerobic digestion tank as described in Embodiment 11 so that the effects of the present embodiment may be enhanced. Moreover, pH of the sludge solid component and/or sludge dissolved component may be adjusted in advance and, then, diluted prior to the introduction to the anaerobic digestion tank.

Although biologically treated water is used for diluent water in the present embodiment, tap water, overflow effluent and rain water are also applicable.

Embodiment 24

Another apparatus embodying the present invention and a process of treating organic wastewater with the apparatus is described.

Figure 34:
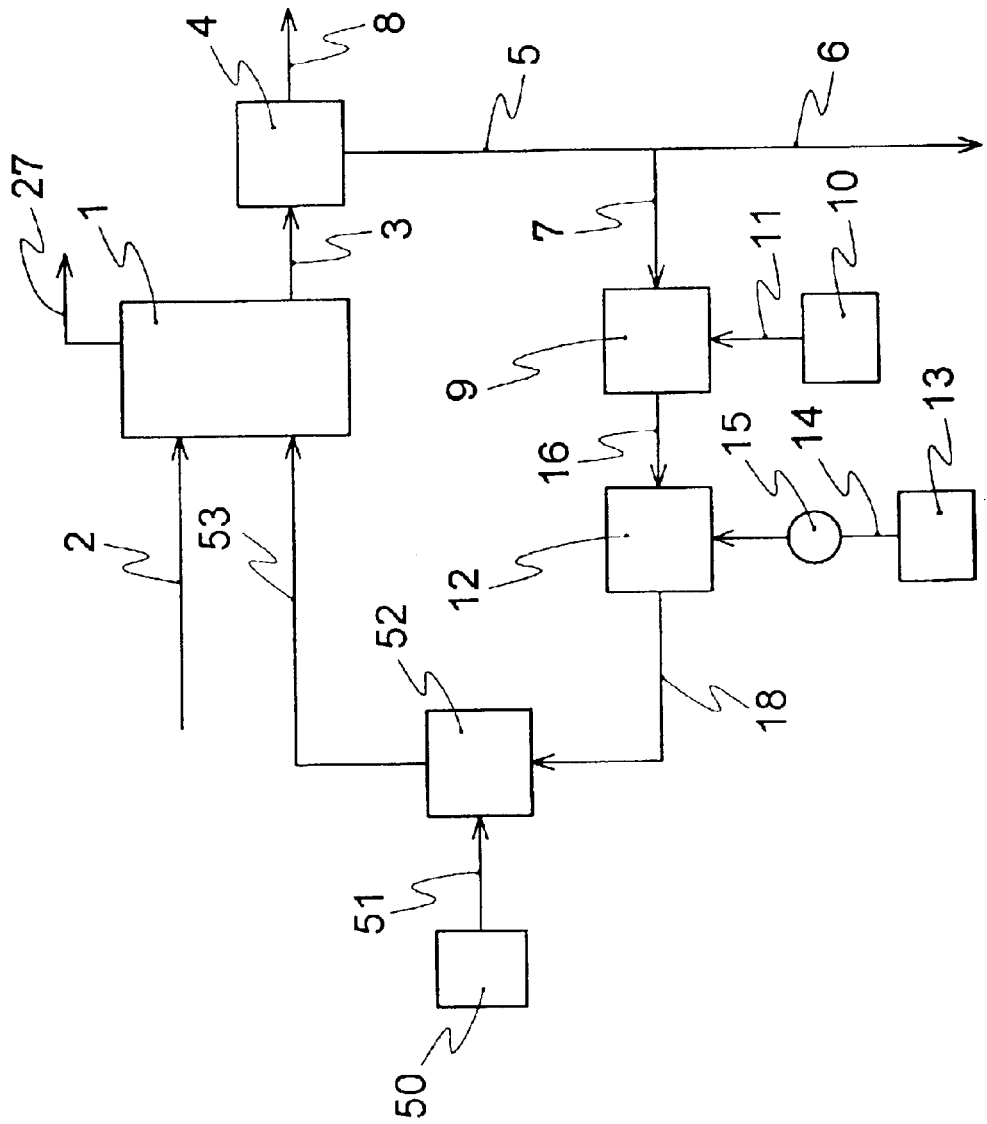
FIG. 34 is a diagram showing an apparatus embodying the present invention and a process flow of treating organic wastewater according to the present invention.

FIG. 34 is a diagram of an apparatus embodying the present invention and shows a process flow of treating organic wastewater with the apparatus. In the apparatus of the present embodiment shown in FIG. 34, components for recovering phosphorus are left out from the apparatus of Embodiment 23 shown in FIG. 33. More specifically, solid-liquid separation tank 17, conduit 19, drain 20, coagulant storage tank 21, coagulant supply pump 22, coagulant supply conduit 23, phosphorus recovery tank 24, conduit 25 for recovering phosphorus and conduit 26 for feeding phosphorus removed water are left out and drain 18 is connected to dilution tank 52. Other than those above, the apparatus of the present embodiment conforms to that of Embodiment 23 shown in FIG. 33.

Hereinafter, workings of the apparatus according to the present embodiment are described.

As described in Embodiment 23, organic sludge from a water treatment plant, which is a mixture of raw sludge from a primary sedimentation tank and excess sludge from an aeration tank, is introduced into anaerobic digestion tank 1 and digested by microorganisms in anaerobic digestion tank 1. In this anaerobic digestion process, the thickened digested sludge in drain 5 is discharged through conduit 6 for disposing sludge, but part of the thickened digested sludge is introduced into ozonization tank 9 through conduit 7 and treated with ozone. Then, the thickened sludge treated with ozone is introduced into alkalization tank 12 and treated with alkali. Thereafter, the thickened sludge treated with alkali is sent to dilution tank 52 via drain 18 for alkali treated sludge. In dilution tank 52, the thickened sludge treated with ozone and alkali is diluted by injecting biologically treated water stored in diluent water storage tank 50 through supply conduit 51 so that the concentration of soluble ion in the thickened sludge is lowered. Thereafter, the diluted sludge is introduced into anaerobic digestion tank 1 via conduit 53 for feeding diluted sludge. Other than those above, the process of the present embodiment conforms to that of Embodiment 23.

The present embodiment is preferable when thickened sludge contains little phosphorus and recovering energy from the sludge is a priority. With the above described combination of preceding ozone and succeeding alkali treatments according to the present embodiment, digested sludge from an anaerobic digestion tank is thickened and then synergistically affected by strong oxidation by ozone as well as decomposition by alkali. In other words, decomposition of organic substances by alkali treatment is highly enhanced by oxidizing the surface thereof with ozone prior to alkali treatment. As a result of this synergistic effects, hardly soluble substances of solids in thickened sludge, such as fibers and cell walls, can be denatured and converted into easily soluble substances which can be easily decomposed by sludge in the anaerobic digestion tank. This improvement in solubilization is much greater than that obtained with ozone treatment alone or alkali treatment alone and, importantly, greater than the sum of these improvements so yield of methane is greatly improved and sludge to be disposed is greatly reduced.

Meanwhile, the thickened sludge may contain residue of sodium hydroxide from the alkali treatment and sodium ions inhibit the activity of the microorganisms for digestion. Accordingly, the operations of the anaerobic digestion tank may become unstable if such thickened sludge is introduced into the anaerobic digestion tank. According to the present embodiment, therefore, the thickened sludge after alkali treatment is diluted by adding biologically treated water so that sodium ion concentration thereof is lowered. Since the thickened sludge of lower sodium ion concentration is introduced into the anaerobic digestion tank, deactivation of the microorganisms by sodium ions hardly occurs and stable operation of the anaerobic digestion tank becomes possible.

In the preset embodiment, the thickened sludge is diluted and then introduced into the anaerobic digestion tank without further treatment. However, pH thereof may be adjusted to approximately neutral before the introduction to the anaerobic digestion tank as described in Embodiment 12 so that the effects of the present embodiment may be enhanced. Moreover, pH of the thickened sludge may be adjusted in advance and then the thickened sludge is diluted prior to the introduction to the anaerobic digestion tank.

Although biologically treated water is used for diluent water in the present embodiment, tap water, overflow effluent and rain water are also applicable.

Embodiment 25

Another apparatus embodying the present invention and a process of treating organic wastewater with the apparatus is described.

Figure 35:
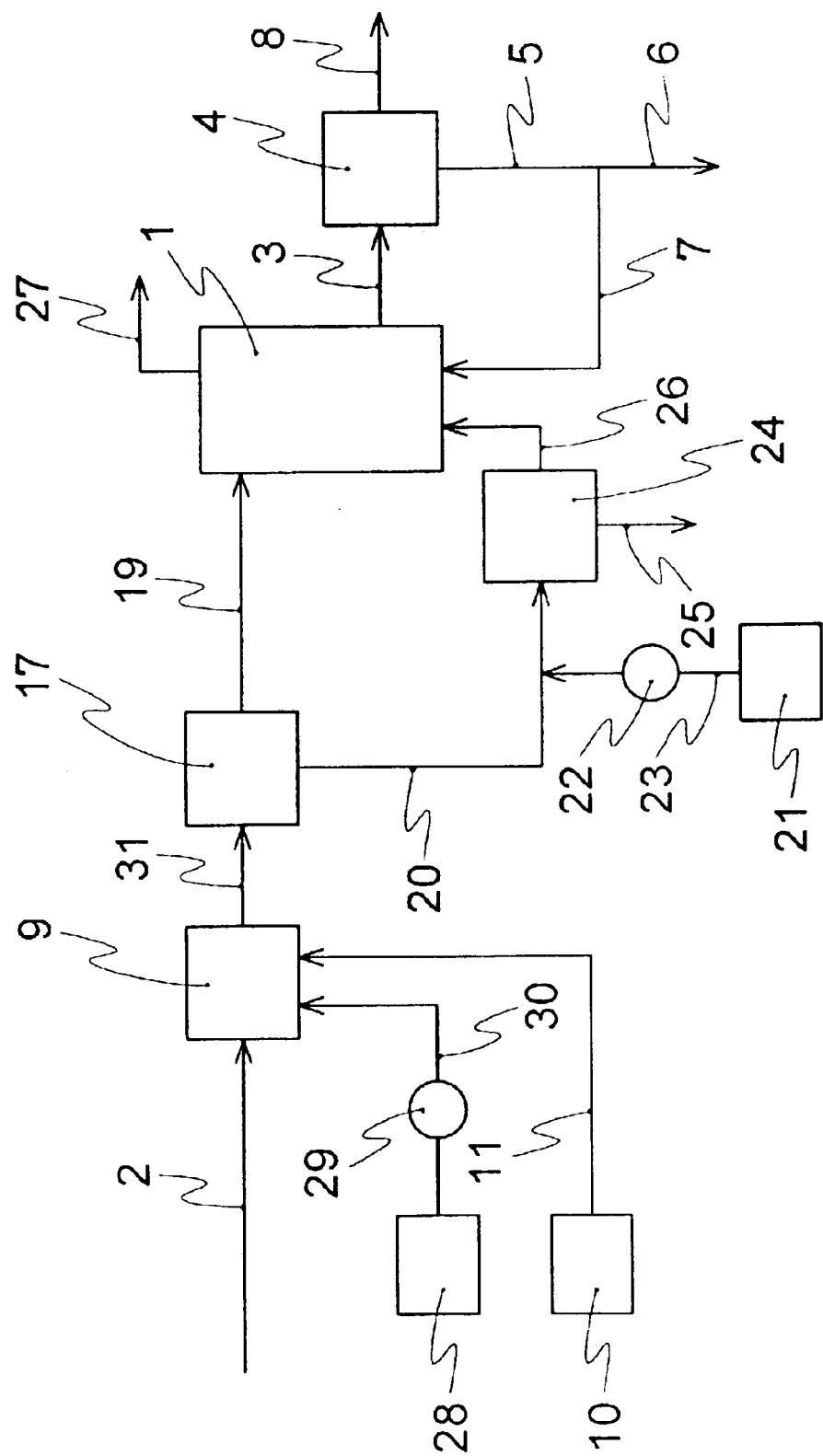
FIG. 35 is a diagram showing an apparatus embodying the present invention and a process flow of treating organic wastewater according to the present invention.

FIG. 35 is a diagram of an apparatus embodying the present invention and shows a process flow of treating organic wastewater with the apparatus. As shown in FIG. 35, ozonization tank 9 and solid-liquid separation tank 17 are arranged between anaerobic digestion tank 1 and organic wastewater feed conduit 2. Ozone generator 10 is connected to ozonization tank 9 via ozone gas supply conduit 11. Hydrogen peroxide storage tank 28 is also connected to ozonization tank 9 via hydrogen peroxide supply conduit 30 and hydrogen peroxide supply conduit 30 is provided with a hydrogen peroxide supply pump 29. Ozonization tank 9 is connected to solid-liquid separation tank 17 via drain 31 for ozone treated sludge and solid-liquid separation tank 17 is connected to anaerobic digestion tank 1 via conduit 19 for feeding treated sludge.

Solid-liquid separation tank 17 is also connected to phosphorus recovery tank 24 via drain 20 for phosphorus containing water and phosphorus recovery tank 24 is connected to anaerobic digestion tank 1 via conduit 26 for feeding phosphorus removed water. Coagulant supply conduit 23 equipped with a coagulant supply pump 22 connects coagulant storage tank 21 to drain 20.

Moreover, anaerobic digestion tank 1 is connected to solid-liquid separation tank 4 via drain 3 for discharging digested sludge. Drain 5 for thickened sludge and drain 8 for supernatant water are connected to solid-liquid separation tank 4. Drain 5 branches into two conduits, one, i.e. conduit 6, is for disposing sludge and the other, i.e. conduit 7, is for returning sludge to anaerobic digestion tank 1. Anaerobic digestion tank 1 has vent 27 for digester gas.

Hereinafter, workings of the apparatus according to the present embodiment arc described.

As organic wastewater to be treated, organic sludge from a water treatment plant, which is a mixture of raw sludge from a primary sedimentation tank and excess sludge from an aeration tank, is introduced into the ozonization tank 9 via conduit 2. The organic sludge is treated with ozone by injecting ozone gas from ozone generator 10 into ozonization tank 9 via conduit 11.

At the same time, pump 29 supplies hydrogen peroxide from hydrogen peroxide storage tank 28 to ozonization tank 9 via conduit 30 and the organic sludge is treated with ozone in the presence of hydrogen peroxide.

The amount of hydrogen peroxide is preferably 20 to 100 mg per 1 liter of the organic sludge. In case where the concentration of hydrogen peroxide is lower than 20 mg/L, organic sludge is not sufficiently denatured and digestion thereof, that is, yield of methane hardly increases. In addition thereto, phosphorus in the sludge is hardly eluted out with such lower hydrogen peroxide concentration. Although higher hydrogen peroxide concentration enhances both yield of methane and elution of phosphorus, this enhancement becomes slower with a concentration higher than 100 mg/L. Therefore, hydrogen peroxide concentration higher than 100 mg/L is considered uneconomical.

As for the amount of ozone, the ozone injection rate is preferably 0.01 to 0.10 $g-O_3/g-SS$ and more preferably 0.03 to 0.07 $g-O_3/g-SS$. With ozone injection rate of lower than 0.01 $g-O_3/g-SS$, organic sludge is not sufficiently denatured and digestion thereof, that is, yield of methane hardly increases. In addition thereto, phosphorus in the sludge is hardly eluted out with such lower ozone injection rate. Although a higher ozone injection rate enhances both yield of methane and elution of phosphorus, this enhancement becomes slower with an ozone injection rate higher than 0.10 $g-O_3/g-SS$. Therefore, an ozone injection rate higher than 0.10 $g-O_3/g-SS$ is considered uneconomical.

After being treated with ozone in the presence of hydrogen peroxide, the organic sludge is sent to solid-liquid separation tank 17 via drain 31 and separated into sludge solid component and sludge dissolved component. The sludge solid component is introduced into anaerobic digestion tank 1 via conduit 19 and anaerobically digested by microorganisms. Meanwhile, the sludge dissolved component rich in phosphorus is introduced into phosphorus recovery tank 24 via drain 20. At the same time, pump 22 on coagulant supply conduit 23 works to supply calcium carbonate solution stored in the coagulant storage tank 21 is injected into and mixed with the phosphorus containing solution flowing through the drain 20, thereby precipitating phosphorus in the sludge dissolved component as calcium phosphate. The precipitate, i.e. calcium phosphate, in phosphorus recovery tank 24, is separated from the solution and drawn out from conduit 25, and the remaining solution without phosphorus is introduced into anaerobic digestion tank 1 via conduit 26 for feeding phosphorus removed water.

The digested sludge in anaerobic digestion tank 1 is discharged from drain 3 and separated into sludge solid component and sludge dissolved component in solid-liquid separation tank 4. The sludge dissolved component is discharged from drain 8 for supernatant water and the sludge solid component is discharged from drain 5 for thickened sludge. The sludge solid component in drain 5 is discharged through conduit 6 for disposing sludge, but part of the sludge solid component is returned to anaerobic digestion tank 1 through conduit 7 for returning sludge. Meanwhile, the digester gas generated in anaerobic digestion tank 1 is recovered from vent 27.

By subjecting organic sludge to ozone treatment in the presence of hydrogen peroxide, radicals such as OH radicals, which have stronger oxidization and decomposition effects than ozone, are generated. As a result, hardly soluble substances of solids in organic sludge, such as fibers and cell walls, can be denatured and converted into easily soluble substances which can be easily decomposed by the sludge in the anaerobic digestion tank. According to the present embodiment, therefore, the soluble amount of solids in the organic sludge is increased and yield of methane is greatly increased and, correspondingly, sludge to be disposed is greatly reduced, as compared with the case of ozone treatment without hydrogen peroxide or addition of hydrogen peroxide without ozone treatment.

In addition, since decomposition of cell walls is increased owing to the activity of radicals, phosphorus in solids of organic sludge is efficiently eluted out, solidified with coagulant and recovered as reusable phosphorus. According to the present embodiment, therefore, it is possible to treat organic sludge while simultaneously recovering energy and resources, i.e. digester gas and phosphorus.

Embodiment 26

Another apparatus embodying the present invention and a process of treating organic wastewater with the apparatus is described.

Figure 36:
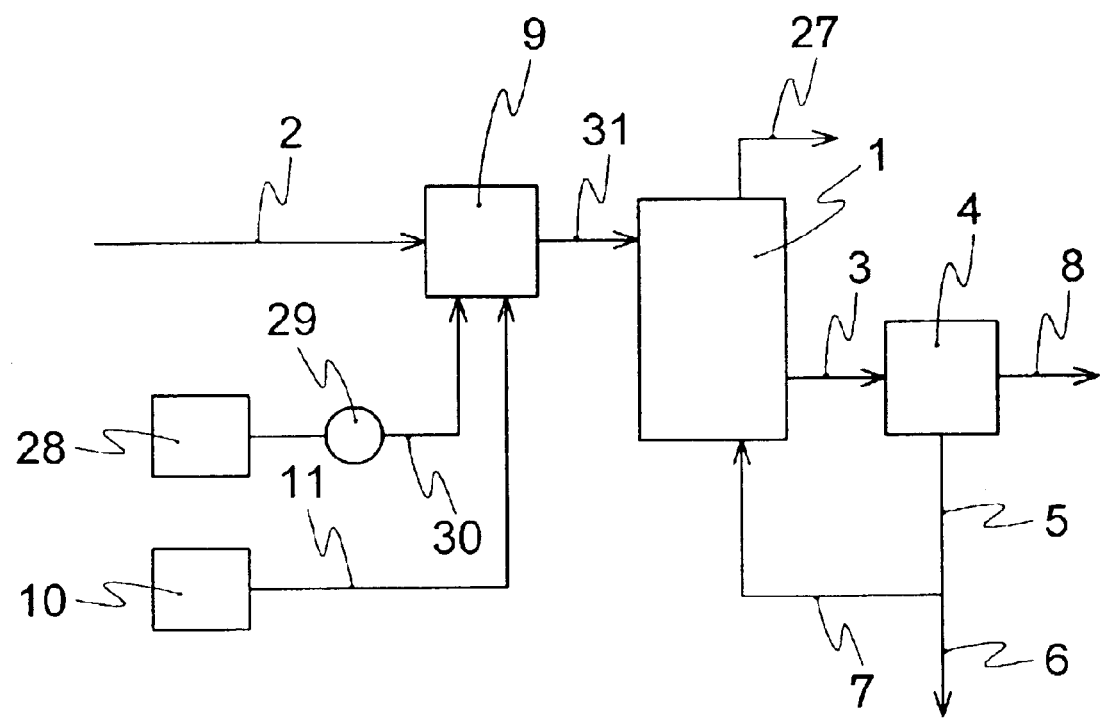
FIG. 36 is a diagram showing an apparatus embodying the present invention and a process flow of treating organic wastewater according to the present invention.

FIG. 36 is a diagram of an apparatus embodying the present invention and shows a process flow of treating organic wastewater with the apparatus. In the apparatus of the present embodiment shown in FIG. 36, components for recovering phosphorus are left out from the apparatus of Embodiment 25 shown in FIG. 35. More specifically, phosphorus recovery tank 24, solid-liquid separation tank 17 and coagulant storage tank 21 are left out and drain 31 for ozone treated sludge connects the ozonization tank 9 to anaerobic digestion tank 1.

Hereinafter, workings of the apparatus according to the present embodiment are described.

As organic wastewater to be treated, organic sludge from a water treatment plant, which is a mixture of raw sludge from a primary sedimentation tank and excess sludge from an aeration tank, is introduced into ozonization tank 9 via conduit 2. The organic sludge is treated with ozone by injecting ozone gas from ozone generator 10 into ozonization tank 9 via conduit 11.

At this time, pump 29 works to supply hydrogen peroxide from hydrogen peroxide storage tank 28 to ozonization tank 9 via conduit 30 so that the organic sludge is treated with ozone in the presence of hydrogen peroxide.

After being treated with ozone in the presence of hydrogen peroxide, the organic sludge is introduced into anaerobic digestion tank 1 via drain 31 and anaerobically digested by microorganisms.

The digested sludge in anaerobic digestion tank 1 is discharged from drain 3 and separated into sludge solid component and sludge dissolved component in solid-liquid separation tank 4. The sludge dissolved component is discharged from drain 8 for supernatant water and sludge solid component are discharged from drain 5 for thickened sludge.

The sludge solid component in drain 5 is discharged through conduit 6 for disposing sludge, but part of the sludge solid component is returned to anaerobic digestion tank 1 through conduit 7 for returning sludge. Meanwhile, the digester gas in anaerobic digestion tank 1 is recovered from vent 27.

The present embodiment is preferable when organic sludge contains little phosphorus and recovering energy from the sludge is a priority. By treating organic sludge with ozone in the presence of hydrogen peroxide, radicals are generated and, owing to the extremely strong oxidization effect of radicals, hardly soluble substances of solids in organic sludge, such as fibers and cell walls, can be denatured and converted into easily soluble substances which can be easily decomposed by sludge in the anaerobic digestion tank. According to the present embodiment, therefore, the soluble amount of solids in the organic sludge is increased and the yield of methane is greatly increased and, correspondingly, sludge to be disposed is greatly reduced as compared with the case of ozone treatment without hydrogen peroxide or addition of hydrogen peroxide without ozone treatment.

Embodiment 27

Another apparatus embodying the present invention and a process of treating organic wastewater with the apparatus is described. In Embodiment 25, influent organic wastewater is treated with ozone in the presence of hydrogen peroxide. In the present embodiment, digested sludge from the anaerobic digestion tank is treated with ozone in the presence of hydrogen peroxide.

Figure 37:
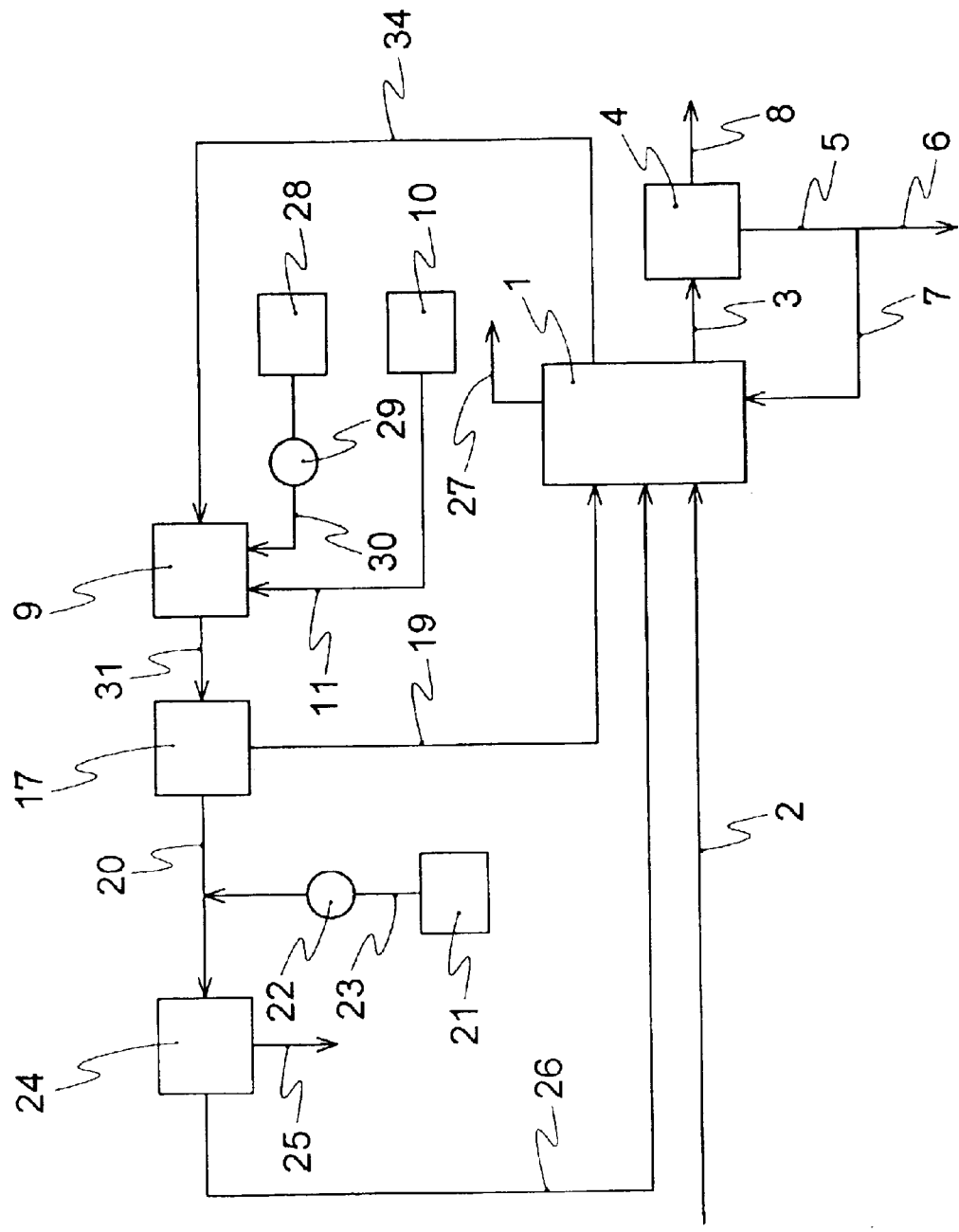
FIG. 37 is a diagram showing an apparatus embodying the present invention and a process flow of treating organic wastewater according to the present invention.

FIG. 37 is a diagram of an apparatus embodying the present invention and shows a process flow of treating organic wastewater with the apparatus. As shown in FIG. 37, organic wastewater feed conduit 2 is connected to anaerobic digestion tank 1. Conduit 34 for discharging digested sludge is connected to anaerobic digestion tank 1 and leads to ozonization tank 9. The ozonization tank 9 is connected to solid-liquid separation tank 17 via drain 31 for ozone treated sludge. Solid-liquid separation tank 17 is connected to anaerobic digestion tank 1 via conduit 19 for feeding treated sludge. Solid-liquid separation tank 17 is also connected to phosphorus recovery tank 24 via drain 20 for phosphorus containing water and phosphorus recovery tank 24 is connected to anaerobic digestion tank 1 via conduit 26 for feeding phosphorus removed water.

Moreover, ozone generator 10 and hydrogen peroxide storage tank 28 are connected to ozonization tank 9 via ozone gas supply conduit 11 and hydrogen peroxide supply conduit 30, respectively. Hydrogen peroxide supply conduit 30 is equipped with hydrogen peroxide supply pump 29.

Solid-liquid separation tank 17 is connected to phosphorus recovery tank 24 via drain 20 as described above, coagulant supply conduit 23 equipped with coagulant supply pump 22 connects coagulant storage tank 21 to drain 20.

Furthermore, anaerobic digestion tank 1 is connected to solid-liquid separation tank 4 via drain 3 for discharging digested sludge. Drain 5 for thickened sludge and drain 8 for supernatant water are connected to solid-liquid separation tank 4. Drain 5 branches into two conduits, one, i.e. conduit 6, is for disposing sludge and the other, i.e. conduit 7, is for returning sludge to anaerobic digestion tank 1, and conduit 7 for returning sludge is connected to anaerobic digestion tank 1. Anaerobic digestion tank 1 has vent 27 for digester gas.

Hereinafter, workings of the apparatus according to the present embodiment are described.

As organic wastewater to be treated, organic sludge from a water treatment plant, which is a mixture of raw sludge from a primary sedimentation tank and excess sludge from an aeration tank, is introduced into anaerobic digestion tank 1 via conduit 2. The organic sludge is digested by microorganisms in the anaerobic digestion tank 1 and, then, the sludge inside anaerobic digestion tank 1 is drawn out from drain 3. The sludge from drain 3 is separated into sludge solid component and sludge dissolved component in solid-liquid separation tank 4. The sludge dissolved component is discharged from drain 8 for supernatant water and the sludge solid component is discharged from drain 5 for thickened sludge.

The sludge solid component in drain 5 is discharged through conduit 6 for disposing sludge, but part of sludge solid component is returned to anaerobic digestion tank 1 through conduit 7 for returning sludge. Meanwhile, the digester gas in anaerobic digestion tank 1 is recovered from vent 27.

In the above anaerobic digestion process, the digested sludge inside the anaerobic digestion tank 1 is sent to ozonization tank 9 through conduit 34. The digested sludge is treated with ozone by injecting ozone gas from ozone generator 10 into ozonization tank 9 via conduit 11. At the same time, pump 29 works to supply hydrogen peroxide from hydrogen peroxide storage tank 28 to ozonization tank 9 via conduit 30 and the digested sludge is treated with ozone in the presence of hydrogen peroxide.

After being treated with ozone in the presence of hydrogen peroxide, the digested sludge is sent to solid-liquid separation tank 17 via drain 31 and separated into sludge solid component and sludge dissolved component. The sludge solid component is introduced into anaerobic digestion tank 1 via conduit 19 and anaerobically digested by microorganisms. Meanwhile, the sludge dissolved component rich in phosphorus is introduced into the phosphorus recovery tank 24 via drain 20. At this time, coagulant supply pump 22 is operated to supply calcium carbonate solution stored in coagulant storage tank 21 is injected into and mixed with the phosphorus containing solution flowing through drain 20 by the coagulant supply pump 22 via coagulant supply conduit 23 and phosphorus in the sludge dissolved component is precipitated as calcium phosphate. The precipitate in phosphorus recovery tank 24, i.e. calcium phosphate, is separated from the solution and drawn out from conduit 25, and the remaining solution without phosphorus is introduced into anaerobic digestion tank 1 via conduit 26 for feeding phosphorus removed water.

By treating digested sludge with ozone in the presence of hydrogen peroxide in this way, radicals such as OH radicals, which have stronger oxidization and decomposition effects than ozone, are generated. As a result, hardly soluble substances of solids in digested sludge, such as fibers and cell walls, can be denatured and converted into easily soluble substances which can be easily decomposed by sludge in the anaerobic digestion tank. According to the present embodiment, therefore, the soluble amount of solids in the organic sludge is increased and the yield of methane is greatly increased and, correspondingly, sludge to be disposed is greatly reduced, as compared with the case of ozone treatment without hydrogen peroxide or addition of hydrogen peroxide without ozone treatment.

In addition, since decomposition of cell walls is increased owing to the activity of radicals, phosphorus in solids of digested sludge is efficiently eluted out, solidified with coagulant and recovered as reusable phosphorus. According to the present embodiment, therefore, it is possible to treat digested sludge while simultaneously recovering energy and resources, i.e. digester gas and phosphorus.

In the digested sludge of the anaerobic digestion tank, hardly soluble substances which organisms cannot decompose, remains and accumulates. According to the present embodiment, therefore, recovery of energy is achieved more efficiently by drawing out part of digested sludge inside the anaerobic digestion tank and denaturing the solid substance in the drawn digested sludge into easily soluble substances.

Embodiment 28

Another apparatus embodying the present invention and a process of treating organic wastewater with the apparatus is described.

Figure 38:
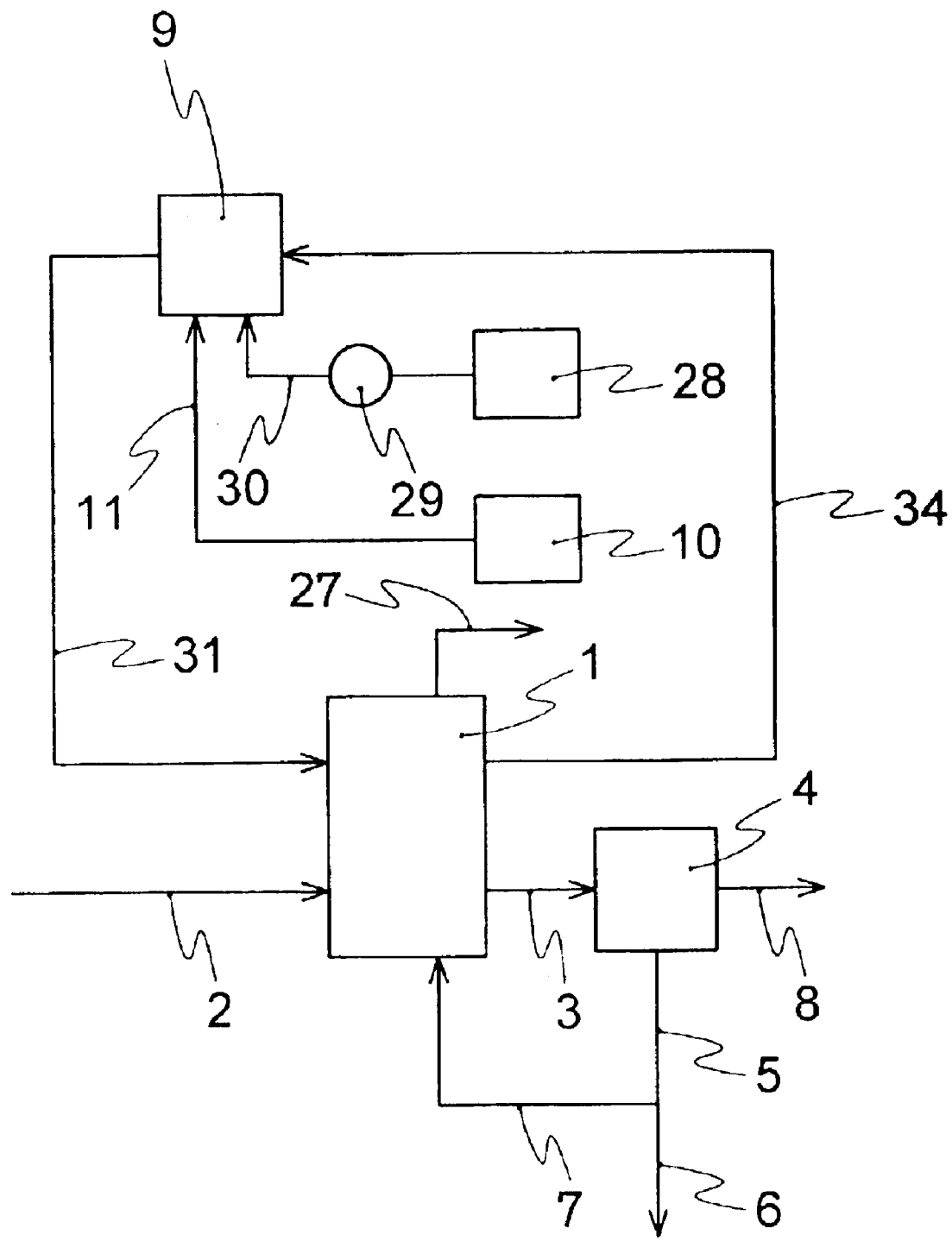
FIG. 38 is a diagram showing an apparatus embodying the present invention and a process flow of treating organic wastewater according to the present invention.

FIG. 38 is a diagram of an apparatus embodying the present invention and shows a process flow of treating organic wastewater with the apparatus. In the apparatus of the present embodiment shown in FIG. 38, components for recovering phosphorus are left out from the apparatus of Embodiment 27 shown in FIG. 37. More specifically, phosphorus recovery tank 24, solid-liquid separation tank 17 and coagulant storage tank 21 are left out and drain 31 for ozone treated sludge connects ozonization tank 9 to anaerobic digestion tank 1.

Hereinafter, workings of the apparatus according to the present embodiment are described.

As organic wastewater to be treated, organic sludge from a water treatment plant, which is a mixture of raw sludge from a primary sedimentation tank and excess sludge from an aeration tank, is introduced into anaerobic digestion tank 1 via conduit 2. The organic sludge is digested by microorganisms in anaerobic digestion tank 1 and, then, the sludge inside anaerobic digestion tank 1 is drawn out from drain 3. The sludge from drain 3 is separated into sludge solid component and sludge dissolved component in solid-liquid separation tank 4. The sludge dissolved component is discharged from drain 8 for supernatant water and the sludge solid component is discharged from drain 5 for thickened sludge.

The sludge solid component in drain 5 is discharged through conduit 6 for disposing sludge, but part of the sludge solid component is returned to anaerobic digestion tank 1 through conduit 7 for returning sludge. Meanwhile, digester gas in anaerobic digestion tank 1 is recovered from vent 27.

In the above anaerobic digestion process, the digested sludge inside anaerobic digestion tank 1 is sent to ozonization tank 9 via conduit 34. The digested sludge is treated with ozone by injecting ozone gas from ozone generator 10 into ozonization tank 9 via conduit 11. At the same time, pump 29 works to supply hydrogen peroxide from hydrogen peroxide storage tank 28 to ozonization tank 9 via conduit 30 and the digested sludge is treated with ozone in the presence of hydrogen peroxide.

After being treated with ozone in the presence of hydrogen peroxide, the digested sludge is introduced into anaerobic digestion tank 1 via drain 31 and anaerobically digested by microorganisms.

The present embodiment is preferable when digested sludge contains little phosphorus and recovering energy from the sludge is a priority. By treating digested sludge with ozone in the presence of hydrogen peroxide, radicals are generated and, owing to the extremely strong oxidization effect of radicals, hardly soluble substances of solids in organic sludge, such as fibers and cell walls, can be denatured and converted into easily soluble substances which can be easily decomposed by sludge in the anaerobic digestion tank. According to the present embodiment, therefore, the soluble amount of solids in the organic sludge is increased and the yield of methane is greatly increased and, correspondingly, sludge to be disposed is greatly reduced, as compared with the case of ozone treatment without hydrogen peroxide or addition of hydrogen peroxide without ozone treatment.

In the digested sludge of the anaerobic digestion tank, hardly soluble substances which organisms cannot decompose remains and accumulates. According to the present embodiment, therefore, recovery of energy is achieved more efficiently by drawing out part of digested sludge inside the anaerobic digestion tank and denaturing solid substances in the drawn digested sludge into easily soluble substances.

Embodiment 29

Another apparatus embodying the present invention and a process of treating organic wastewater with the apparatus is described. In Embodiment 25, influent organic wastewater is treated with ozone in presence of hydrogen peroxide. In Embodiment 27, digested sludge from the anaerobic digestion tank is treated with ozone in the presence of hydrogen peroxide. In the present embodiment, meanwhile, digested sludge is thickened through solid-liquid separation and, then, the thickened sludge is treated with ozone in the presence of hydrogen peroxide.

Figure 39:
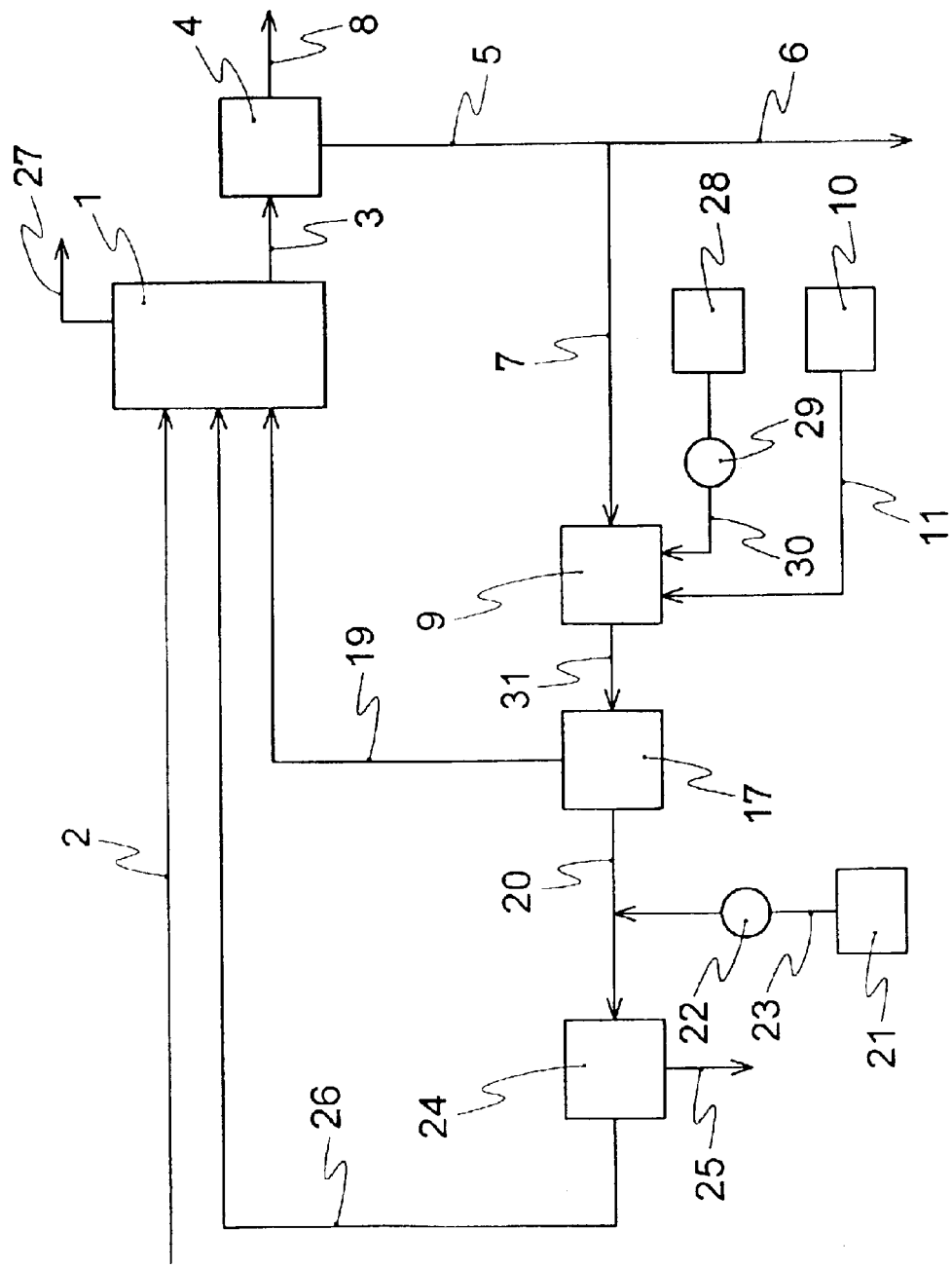
FIG. 39 is a diagram showing an apparatus embodying the present invention and a process flow of treating organic wastewater according to the present invention.

FIG. 39 is a diagram of an apparatus embodying the present invention and shows a process flow of treating organic wastewater with the apparatus. As shown in FIG. 39, organic wastewater feed conduit 2 is connected to anaerobic digestion tank 1. Anaerobic digestion tank 1 is connected to solid-liquid separation tank 4 via drain 3 for discharging digested sludge. Drain 5 for thickened sludge and drain 8 for supernatant water are connected to solid-liquid separation tank 4. Drain 5 branches into two conduits, one, i.e. conduit 6, is for disposing sludge and the other, i.e. conduit 7, is for returning sludge to ozonization tank 9, and conduit 7 for returning sludge is connected to ozonization tank 9. Ozonization tank 9 is connected to solid-liquid separation tank 17 via drain 31 for ozone treated sludge. Solid-liquid separation tank 17 is connected to anaerobic digestion tank 1 via conduit 19 for feeding treated sludge and connected to phosphorus recovery tank 24 via drain 20 for phosphorus containing water. The phosphorus recovery tank 24 is connected to anaerobic digestion tank 1 via conduit 26 for feeding phosphorus removed water. The anaerobic digestion tank 1 has vent 27 for digester gas.

Moreover, ozone generator 10 and hydrogen peroxide storage tank 28 are connected to ozonization tank 9 via ozone gas supply conduit 11 and hydrogen peroxide supply conduit 30, respectively. The hydrogen peroxide supply conduit 30 is equipped with hydrogen peroxide supply pump 29.

The solid-liquid separation tank 17 is connected to phosphorus recovery tank 24 via drain 20 as described above, coagulant supply conduit 23 equipped with coagulant supply pump 22 connects coagulant storage tank 21 to drain 20.

Hereinafter, workings of the apparatus according to the present embodiment are described.

As organic wastewater to be treated, organic sludge from a water treatment plant, which is a mixture of raw sludge from a primary sedimentation tank and excess sludge from an aeration tank, is introduced into anaerobic digestion tank 1 via conduit 2. The organic sludge is digested by microorganisms in anaerobic digestion tank 1 and, then, the sludge inside anaerobic digestion tank 1 is drawn out from drain 3. The sludge from drain 3 is separated into sludge solid component and sludge dissolved component in solid-liquid separation tank 4. The sludge dissolved component is discharged from drain 8 for supernatant water and the sludge solid component is discharged from drain 5 for thickened sludge.

The sludge solid component in drain 5 is discharged through conduit 6 for disposing sludge, but part of the sludge solid component is returned to ozonization tank 9 through conduit 7 for returning sludge. Meanwhile, the digester gas in anaerobic digestion tank 1 is recovered from vent 27.

In ozonization tank 9, the thickened sludge from conduit 7 is treated with ozone by injecting ozone gas from ozone generator 10 into ozonization tank 9 via conduit 11. At the same time, pump 29 works to supply hydrogen peroxide from hydrogen peroxide storage tank 28 to ozonization tank 9 via conduit 30 and the thickened sludge is treated with ozone in the presence of hydrogen peroxide.

After being treated with ozone in the presence of hydrogen peroxide, the thickened sludge is sent to solid-liquid separation tank 17 via drain 31 and separated into sludge solid component and sludge dissolved component. The sludge solid component is introduced into anaerobic digestion tank 1 via conduit 19 and anaerobically digested by microorganisms. Meanwhile, the sludge dissolved component rich in phosphorus is introduced into phosphorus recovery tank 24 via drain 20. At this time, coagulant supply pump 22 is operated to supply calcium carbonate solution in coagulant storage tank 21 is injected into and mixed with the phosphorus containing solution flowing through drain 20 by the coagulant supply pump 22 via coagulant supply conduit 23 and phosphorus in the sludge dissolved component is precipitated as calcium phosphate. The precipitate in phosphorus recovery tank 24, i.e. calcium phosphate, is separated from the solution and drawn out from conduit 25, and the remaining solution without phosphorus is introduced into anaerobic digestion tank 1 via conduit 26 for feeding phosphorus removed water.

By treating the thickened digested sludge with ozone in the presence of hydrogen peroxide, radicals such as OH radicals, which have stronger oxidization and decomposition effects than ozone, are generated. As a result, hardly soluble substances of solids in thickened sludge, such as fibers and cell walls, can be denatured and converted into easily soluble substances which can be easily decomposed by sludge in the anaerobic digestion tank. According to the present embodiment, therefore, the soluble amount of solids in the thickened sludge is increased and the yield of methane is greatly increased and, correspondingly, sludge to be disposed is greatly reduced, as compared with the case of ozone treatment without hydrogen peroxide or addition of hydrogen peroxide without ozone treatment.

In addition, since decomposition of cell walls is increased owing to the activity of radicals, phosphorus in solids of digested sludge is efficiently eluted out, solidified with coagulant and recovered as reusable phosphorus. According to the present embodiment, therefore, it is possible to treat digested sludge while simultaneously recovering energy and resources, i.e. digester gas and phosphorus.

In the digested sludge of the anaerobic digestion tank, hardly soluble substances which organisms cannot decompose remains and accumulates. According to the present embodiment, therefore, recovery of energy is achieved more efficiently by thickening the digested sludge inside the anaerobic digestion tank and denaturing solid substances in the thickened digested sludge into easily soluble substances.

Embodiment 30

Another apparatus embodying the present invention and a process of treating organic wastewater with the apparatus is described.

Figure 40:
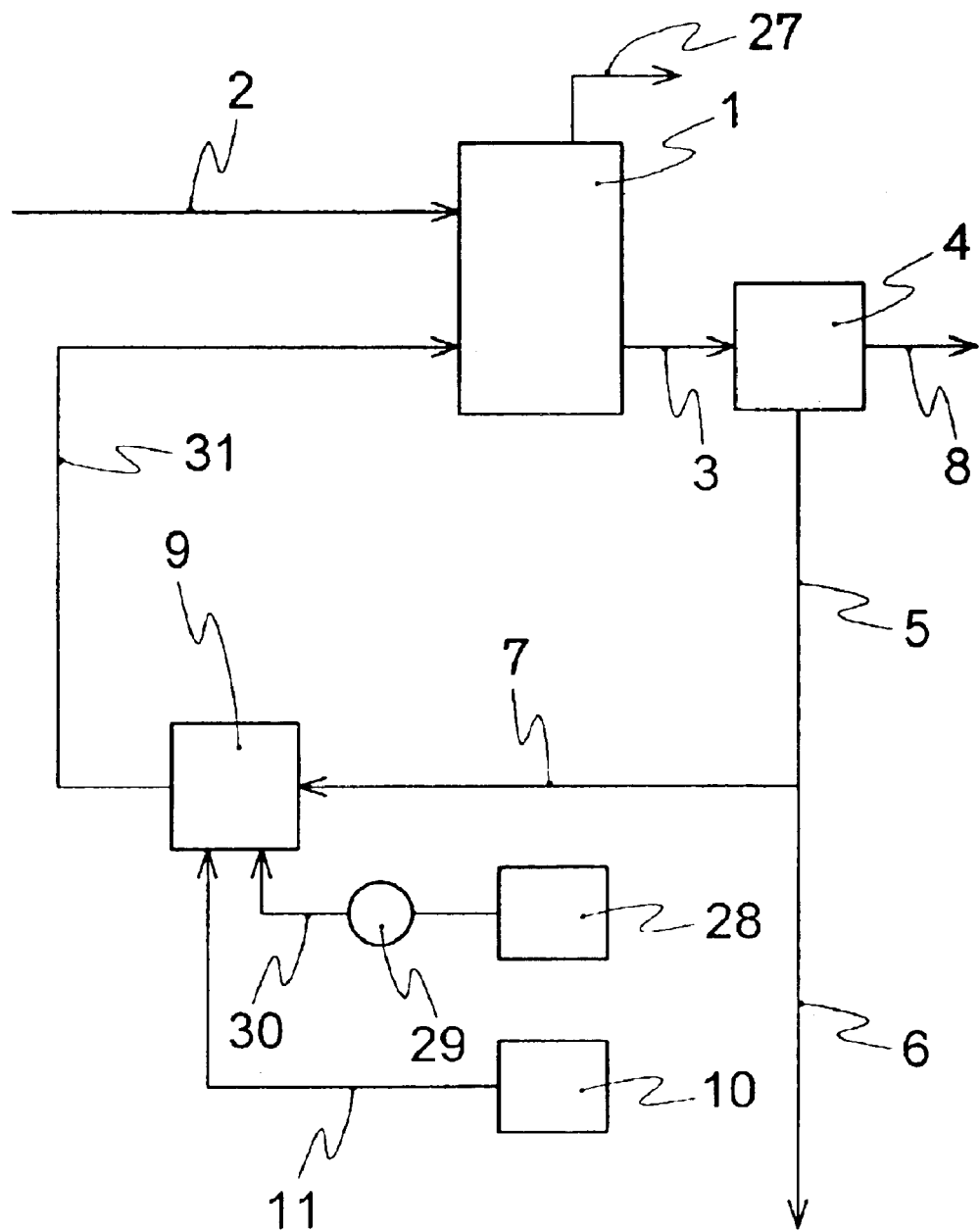
FIG. 40 is a diagram showing an apparatus embodying the present invention and a process flow of treating organic wastewater according to the present invention.

FIG. 40 is a diagram of an apparatus embodying the present invention and shows a process flow of treating organic wastewater with the apparatus. In the apparatus of the present embodiment shown in FIG. 40, components for recovering phosphorus are left out from the apparatus of Embodiment 29 shown in FIG. 39. More specifically, phosphorus recovery tank 24, solid-liquid separation tank 17 and coagulant storage tank 21 are left out and drain 31 for ozone treated sludge connects ozonization tank 9 to anaerobic digestion tank 1.

Hereinafter, workings of the apparatus according to the present embodiment are described.

As organic wastewater to be treated, organic sludge from a water treatment plant, which is a mixture of raw sludge from a primary sedimentation tank and excess sludge from an aeration tank, is introduced into anaerobic digestion tank 1 via the conduit 2. The organic sludge is digested by microorganisms in anaerobic digestion tank 1 and, then, the sludge inside anaerobic digestion tank 1 is drawn out from drain 3. The sludge from drain 3 is separated into sludge solid component and sludge dissolved component at solid-liquid separation tank 4. The sludge dissolved component is discharged from drain 8 for supernatant water and the sludge solid component is discharged from drain 5 for thickened sludge.

The sludge solid component in drain 5 is discharged through conduit 6 for disposing sludge, but part of the sludge solid component is returned to ozonization tank 9 through conduit 7 for returning sludge. Meanwhile, the digester gas in anaerobic digestion tank 1 is recovered from vent 27.

In ozonization tank 9, the thickened sludge from conduit 7 is treated with ozone by injecting ozone gas from ozone generator 10 into ozonization tank 9 via conduit 11. At the same time, pump 29 works to supply hydrogen peroxide from the hydrogen peroxide storage tank 28 to ozonization tank 9 via conduit 30 and the thickened sludge is treated with ozone in the presence of hydrogen peroxide.

After being treated with ozone in the presence of hydrogen peroxide, the thickened sludge is introduced into anaerobic digestion tank 1 via drain 31 and anaerobically digested by microorganisms.

The present embodiment is preferable when digested sludge contains little phosphorus and recovering energy from the sludge is a priority. By treating thickened digested sludge with ozone in the presence of hydrogen peroxide, radicals such as OH radicals, which have stronger oxidization and decomposition effects than ozone, are generated. As a result, hardly soluble substances of solids in thickened sludge, such as fibers and cell walls, can be denatured and converted into easily soluble substances which can be easily decomposed by sludge in the anaerobic digestion tank. According to the present embodiment, therefore, solubilization of solids in the thickened sludge is enhanced and the yield of methane is greatly increased and, correspondingly, sludge to be disposed is greatly reduced, as compared to the case of ozone treatment without hydrogen peroxide or addition of hydrogen peroxide without ozone treatment.

In the digested sludge of the anaerobic digestion tank, hardly soluble substances which organisms cannot decompose, remains and accumulates. According to the present embodiment, therefore, recovery of energy is achieved more efficiently by thickening the digested sludge in the anaerobic digestion tank and denaturing solid substances in the thickened digested sludge into easily soluble substances.

Embodiment 31

Another apparatus embodying the present invention and a process of treating organic wastewater with the apparatus is described.

Figure 41:
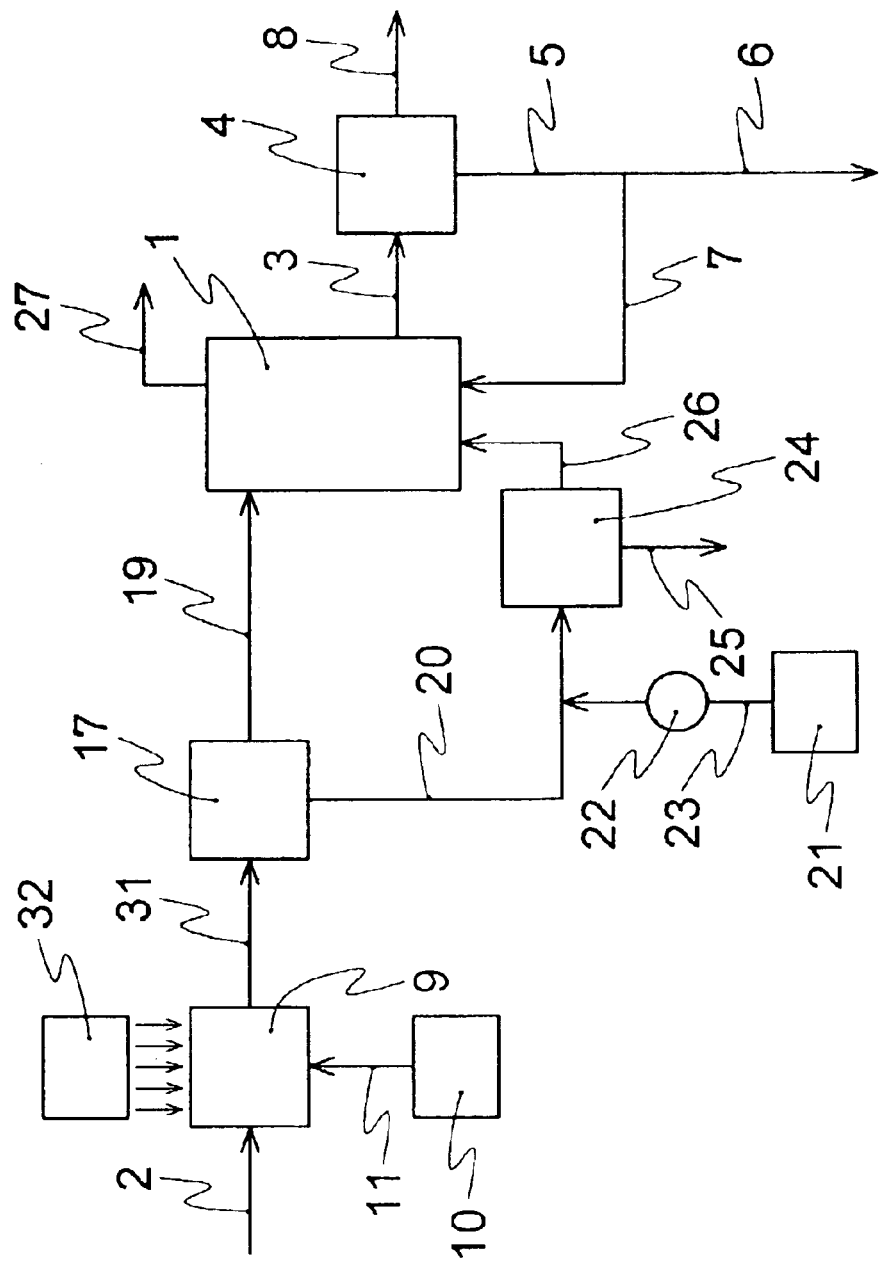
FIG. 41 is a diagram showing an apparatus embodying the present invention and a process flow of treating organic wastewater according to the present invention.

FIG. 41 is a diagram of an apparatus embodying the present invention and shows a process flow of treating organic wastewater with the apparatus. As shown in FIG. 41, ozonization tank 9 and solid-liquid separation tank 17 are arranged between anaerobic digestion tank 1 and organic wastewater feed conduit 2. Ozone generator 10 is connected to ozonization tank 9 via ozone gas supply conduit 11. The top surface of ozonization tank 9 is designed to let in ultraviolet from UV radiator 32 through, e.g. a transparent window.

Solid-liquid separation tank 17 is also connected to phosphorus recovery tank 24 via drain 20 for phosphorus containing water and phosphorus recovery tank 24 is connected to anaerobic digestion tank 1 via conduit 26 for feeding phosphorus removed water. Coagulant supply conduit 23 equipped with coagulant supply pump 22 connects coagulant storage tank 21 to drain 20.

Moreover, anaerobic digestion tank 1 is connected to solid-liquid separation tank 4 via drain 3 for drawing digested sludge. Drain 5 for thickened sludge and drain 8 for supernatant water are connected to solid-liquid separation tank 4. Drain 5 branches into two conduits; one, i.e. conduit 6, is for disposing sludge and the other, i.e. conduit 7, is for returning sludge to the anaerobic digestion tank 1. Anaerobic digestion tank 1 has vent 27 for digester gas.

Hereinafter, workings of the apparatus according to the present embodiment are described.

As organic wastewater to be treated, organic sludge from a water treatment plant, which is a mixture of raw sludge from a primary sedimentation tank and excess sludge from an aeration tank, is introduced into ozonization tank 9 via conduit 2. The organic sludge is treated with ozone by injecting ozone gas from ozone generator 10 into ozonization tank 9 via conduit 11.

At this time, the organic sludge inside the ozonization tank 9 is exposed to UV radiation from UV radiator 32 so that the organic sludge is treated with ozone under UV radiation.

In the above ozone treatment under UV radiation, the wavelength of UV radiation is preferably 180 to 300 nm, output of UV radiation is preferably 5.0 to 200 W and exposure to the UV radiation is preferably 5 to 30 minutes. In case where wavelength of UV radiation is longer than 300 nm, organic sludge is not sufficiently denatured and digestion thereof, that is, yield of methane hardly increases. In addition thereto, phosphorus in the sludge is hardly eluted out with the UV radiation of such a longer wavelength. Although shorter wavelength enhances both yield of methane and elution of phosphorus, this enhancement becomes slower with a wavelength shorter than 180 nm. Therefore, wavelength shorter than 180 nm is considered uneconomical. In case where output of the UV radiation is smaller than 5.0 W, organic sludge is not sufficiently denatured and digestion thereof, that is, yield of methane hardly increases. In addition thereto, phosphorus in the sludge is hardly eluted out with an UV radiation of such a smaller output. Although larger output enhances both yield of methane and elution of phosphorus, this enhancement becomes slower with an output larger than 200 W. Therefore, output larger than 200 W is considered uneconomical. In case where exposure to the UV radiation is shorter than 5 minutes, organic sludge is not sufficiently denatured and digestion thereof, that is, yield of methane hardly increases. In addition thereto, phosphorus in the sludge is hardly eluted out with such shorter exposure. Although longer exposure enhances both yield of methane and elution of phosphorus, this enhancement becomes slower with the exposure longer than 30 minutes. Therefore, exposure longer than 30 minutes is considered uneconomical.

As for the amount of ozone, the ozone injection rate is preferably 0.01 to 0.10 g-$O_3$/g-SS and more preferably 0.03 to 0.07 g-$O_3$/g-SS. With an ozone injection rate smaller than 0.01 g-$O_3$/g-SS, organic sludge is not sufficiently denatured and digestion thereof, that is, yield of methane hardly increases. In addition thereto, phosphorus in the sludge is hardly eluted out with such smaller ozone injection rate. Although larger ozone injection rate enhances both yield of methane and elution of phosphorus, this enhancement becomes slower with an ozone injection rate larger than 0.10 g-$O_3$/g-SS. Therefore, an ozone injection rate larger than 0.10 g-$O_3$/g-SS is considered uneconomical.

After being treated with ozone under UV radiation, the organic sludge is sent to solid-liquid separation tank 17 via drain 31 and separated into sludge solid component and sludge dissolved component. The sludge solid component is introduced into anaerobic digestion tank 1 via conduit 19 and anaerobically digested by microorganisms. Meanwhile, the sludge dissolved component rich in phosphorus is introduced into phosphorus recovery tank 24 via drain 20. At the same time, pump 22 on coagulant supply conduit 23 works and calcium carbonate solution in coagulant storage tank 21 is injected into and mixed with the phosphorus containing solution flowing through drain 20 and phosphorus in the sludge dissolved component is precipitated as calcium phosphate. The precipitate, i.e. calcium phosphate, in phosphorus recovery tank 24, is separated from the solution and drawn out from conduit 25, and the remaining solution without phosphorus is introduced into anaerobic digestion tank 1 via conduit 26 for feeding phosphorus removed water.

The digested sludge in anaerobic digestion tank 1 is discharged from drain 3 and separated into sludge solid component and sludge dissolved component in solid-liquid separation tank 4. The sludge dissolved component is discharged from drain 8 for supernatant water and the sludge solid component is discharged from drain 5 for thickened sludge.

The sludge solid component in drain 5 is discharged through conduit 6 for disposing sludge, but part of the sludge solid component is returned to anaerobic digestion tank 1 through conduit 7 for returning sludge. Meanwhile, the digester gas in anaerobic digestion tank 1 is recovered from vent 27.

As described above, this embodiment relates to an apparatus for treating organic wastewater comprising a means for treating organic wastewater with ozone under UV radiation and an anaerobic digestion tank for anaerobically digesting the ozone treated organic wastewater. This embodiment also relates to a process for treating organic wastewater by anaerobic digestion, which comprises treating organic wastewater with ozone under UV radiation and introducing said ozone treated organic wastewater into an anaerobic digestion tank.

By treating organic sludge with ozone under UV radiation in this way, radicals such as OH radicals, which have stronger oxidization and decomposition effects than ozone, are generated. As a result, hardly soluble substances of solids in organic sludge, such as fibers and cell walls, can be denatured and converted into easily soluble substances which can be easily decomposed by sludge in the anaerobic digestion tank. According to the present embodiment, therefore, solubility of solids in the organic sludge is increased and yield of methane is greatly increased and, correspondingly, sludge to be disposed is greatly reduced, as compared with the case of ozone treatment without UV radiation or UV radiation without ozone treatment.

In addition, since decomposition of cell walls is increased owing to the activity of radicals, phosphorus in solids of organic sludge is efficiently eluted out, solidified with coagulant and recovered as reusable phosphorus. According to the present embodiment, therefore, it is possible to treat organic sludge while simultaneously recovering energy and resources, i.e. digester gas and phosphorus.

Embodiment 32

Another apparatus embodying the present invention and a process of treating organic wastewater with the apparatus is described.

Figure 42:
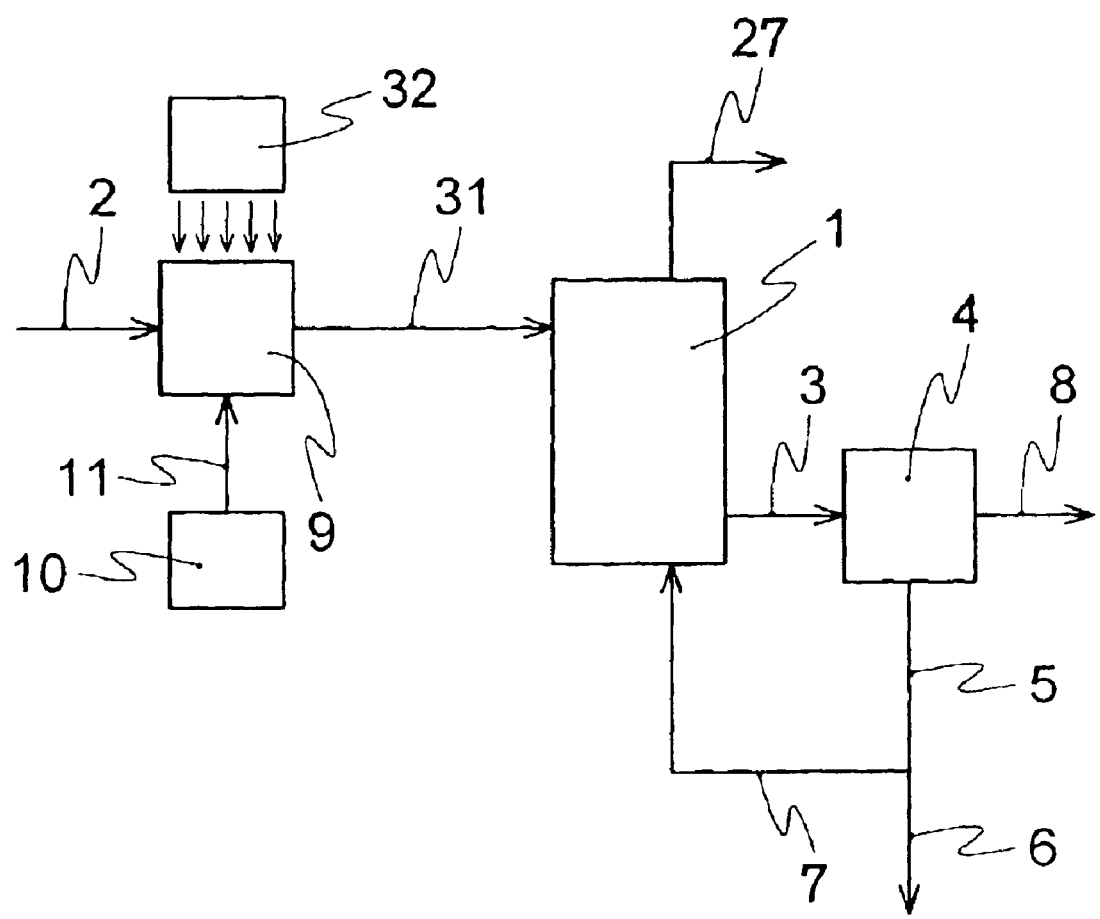
FIG. 42 is a diagram showing an apparatus embodying the present invention and a process flow of treating organic wastewater according to the present invention.

FIG. 42 is a diagram of an apparatus embodying the present invention and shows a process flow of treating organic wastewater with the apparatus. In the apparatus of the present embodiment shown in FIG. 42, components for recovering phosphorus are left out from the apparatus of Embodiment 31 shown in FIG. 41. More specifically, phosphorus recovery tank 24, solid-liquid separation tank 17 and coagulant storage tank 21 are left out and drain 31 for ozone treated sludge connects ozonization tank 9 to anaerobic digestion tank 1.

Hereinafter, workings of the apparatus according to the present embodiment are described.

As organic wastewater to be treated, organic sludge from a water treatment plant, which is a mixture of raw sludge from a primary sedimentation tank and excess sludge from an aeration tank, is introduced into ozonization tank 9 via conduit 2. The organic sludge is treated with ozone by injecting ozone gas from ozone generator 10 into ozonization tank 9 via conduit 11.

At this time, the organic sludge inside ozonization tank 9 is exposed to UV radiation from UV radiator 32 and the organic sludge is treated with ozone under UV radiation.

After being treated with ozone under UV radiation, the organic sludge is introduced into anaerobic digestion tank 1 via drain 31 and anaerobically digested by microorganisms. The digested sludge in anaerobic digestion tank 1 is discharged from drain 3 and separated into sludge solid component and sludge dissolved component in solid-liquid separation tank 4. The sludge dissolved component is discharged from drain 8 for supernatant water and the sludge solid component is discharged from drain 5 for thickened sludge.

The sludge solid component in drain 5 is discharged through conduit 6 for disposing sludge, but part of the sludge solid component is returned to anaerobic digestion tank 1 through conduit 7 for returning sludge. Meanwhile, the digester gas in anaerobic digestion tank 1 is recovered from vent 27.

The present embodiment is preferable when organic sludge contains little phosphorus and recovering energy from the sludge is a priority. By treating organic sludge with ozone under UV radiation, radicals are generated and, owing to the extremely strong oxidization effect of radicals, hardly soluble substances of solids in organic sludge, such as fibers and cell walls, can be denatured and converted into easily soluble substances which can be easily decomposed by sludge in the anaerobic digestion tank. According to the present embodiment, therefore, solubility of solids in the organic sludge is increased and yield of methane is greatly increased and, correspondingly, sludge to be disposed is greatly reduced as compared with the case of ozone treatment without UV radiation or UV radiation without ozone treatment.

Embodiment 33

Another apparatus embodying the present invention and a process of treating organic wastewater with the apparatus is described. In Embodiment 31, influent organic wastewater is treated with ozone under UV radiation. In the present embodiment, digested sludge drawn from the anaerobic digestion tank is treated with ozone under UV radiation.

Figure 43:
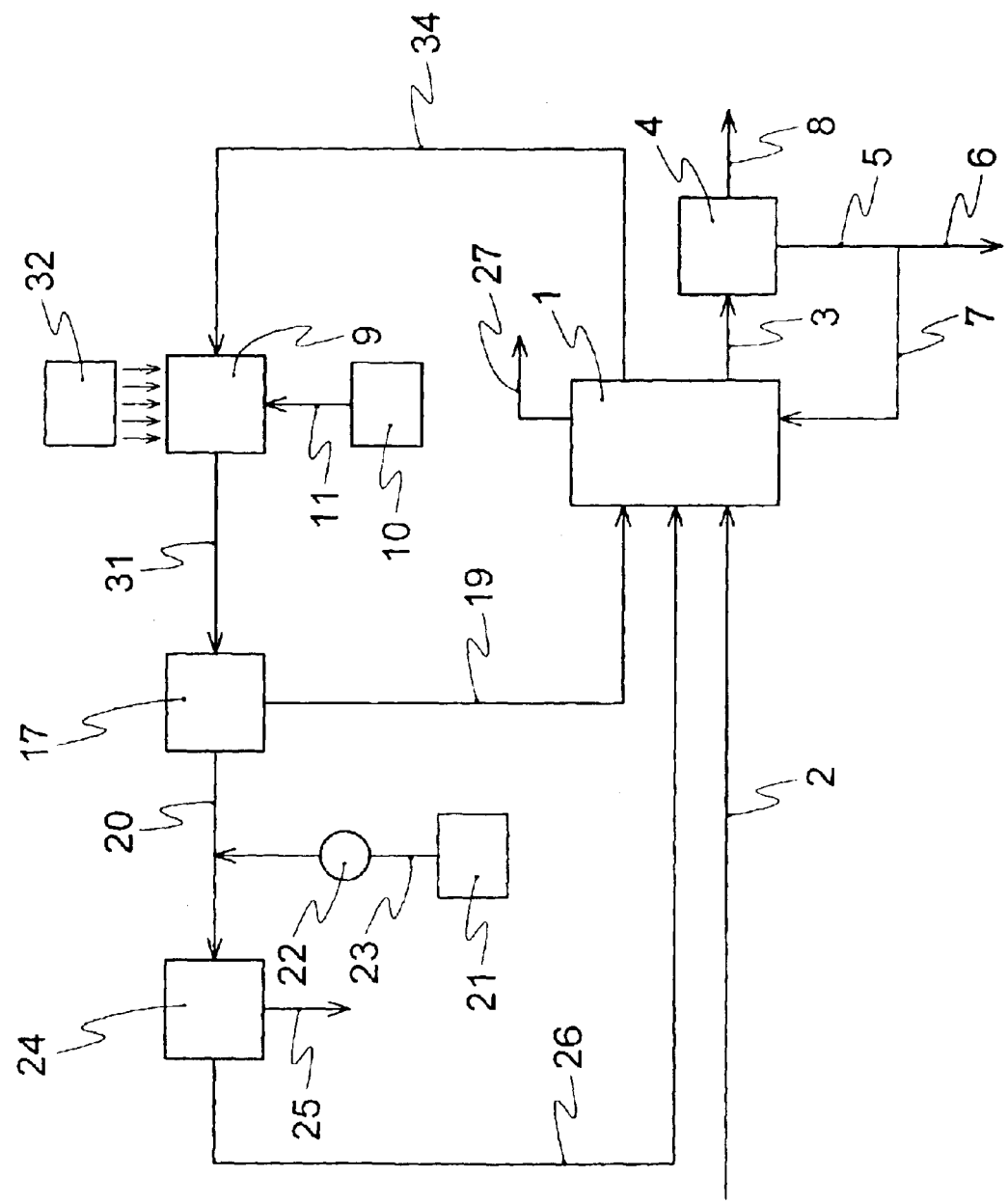
FIG. 43 is a diagram showing an apparatus embodying the present invention and a process flow of treating organic wastewater according to the present invention.

FIG. 43 is a diagram of an apparatus embodying the present invention and shows a process flow of treating organic wastewater with the apparatus. As shown in FIG. 43, organic wastewater feed conduit 2 is connected to anaerobic digestion tank 1. Conduit 34 for drawing digested sludge is connected to anaerobic digestion tank 1 and leads to ozonization tank 9. Ozonization tank 9 is connected to solid-liquid separation tank 17 via drain 31 for ozone treated sludge. Solid-liquid separation tank 17 is connected to anaerobic digestion tank 1 via conduit 19 for feeding treated sludge. Solid-liquid separation tank 17 is also connected to phosphorus recovery tank 24 via drain 20 for phosphorus containing water and phosphorus recovery tank 24 is connected to anaerobic digestion tank 1 via conduit 26 for feeding phosphorus removed water.

Moreover, ozone generator 10 is connected to ozonization tank 9 via ozone gas supply conduit 11. The top surface of the ozonization tank 9 is designed to let in ultraviolet radiation from UV radiator 32 through, e.g. a transparent window.

Solid-liquid separation tank 17 is connected to phosphorus recovery tank 24 via drain 20 as described above, and coagulant supply conduit 23 equipped with coagulant supply pump 22 connects coagulant storage tank 21 to drain 20.

Furthermore, anaerobic digestion tank 1 is connected to solid-liquid separation tank 4 via drain 3 for drawing digested sludge. Drain 5 for thickened sludge and drain 8 for supernatant water are connected to solid-liquid separation tank 4. Drain 5 branches into two conduits; one, i.e. conduit 6, is for disposing sludge and the other, i.e. conduit 7, is for returning sludge to anaerobic digestion tank 1. Anaerobic digestion tank 1 has vent 27 for digester gas.

Hereinafter, workings of the apparatus according to the present embodiment are described.

As organic wastewater to be treated, organic sludge from a water treatment plant, which is a mixture of raw sludge from a primary sedimentation tank and excess sludge from an aeration tank, is introduced into anaerobic digestion tank 1 via conduit 2. The organic sludge is digested by microorganisms in anaerobic digestion tank 1 and, then, the sludge inside anaerobic digestion tank 1 is discharged from drain 3. The sludge from drain 3 is separated into sludge solid component and sludge dissolved component at solid-liquid separation tank 4. The sludge dissolved component is discharged from drain 8 for supernatant water and the sludge solid component is discharged from drain 5 for thickened sludge.

The sludge solid component in drain 5 is discharged through conduit 6 for disposing sludge, but part of the sludge solid component is returned to anaerobic digestion tank 1 through conduit 7 for returning sludge. Meanwhile, the digester gas in anaerobic digestion tank 1 is recovered from vent 27.

In the above anaerobic digestion process, the digested sludge inside anaerobic digestion tank 1 is drawn out from the conduit 34 and sent to ozonization tank 9. The digested sludge is treated with ozone by injecting ozone gas from ozone generator 10 into ozonization tank 9 via conduit 11. At this time, the organic sludge inside ozonization tank 9 is exposed to UV radiation from UV radiator 32 so that the organic sludge is treated with ozone under UV radiation.

After being treated with ozone under UV radiation, the digested sludge is sent to solid-liquid separation tank 17 via drain 31 and separated into sludge solid component and sludge dissolved component. The sludge solid component is introduced into anaerobic digestion tank 1 via conduit 19 and anaerobically digested by microorganisms. Meanwhile, the sludge dissolved component rich in phosphorus is introduced into phosphorus recovery tank 24 via drain 20. At the same time, calcium carbonate solution in coagulant storage tank 21 is injected into and mixed with the phosphorus containing solution flowing through drain 20 by coagulant supply pump 22 via coagulant supply conduit 23 and phosphorus in the sludge dissolved component is precipitated as calcium phosphate. The precipitate in the phosphorus recovery tank 24, i.e. calcium phosphate, is separated from the solution and drawn out from conduit 25 and the remaining solution without phosphorus is introduced into anaerobic digestion tank 1 via conduit 26 for feeding phosphorus removed water.

By treating digested sludge with ozone under UV radiation, radicals such as OH radicals, which have stronger oxidization and decomposition effects than ozone, are generated. As a result, hardly soluble substances of solids in digested sludge, such as fibers and cell walls, can be denatured and converted into easily soluble substances which can be easily decomposed by sludge in the anaerobic digestion tank. According to the present embodiment, therefore, solubility of solids in the organic sludge is increased and yield of methane is greatly increased and, correspondingly, sludge to be disposed is greatly reduced as compared with the case of ozone treatment without UV radiation or UV radiation without ozone treatment.

In addition, since decomposition of cell walls is increased owing to the activity of radicals, phosphorus in solids of digested sludge is efficiently eluted out, solidified with coagulant and recovered as reusable phosphorus. According to the present embodiment, therefore, it is possible to treat digested sludge while simultaneously recovering energy and resources, i.e. digester gas and phosphorus.

In the digested sludge of the anaerobic digestion tank, hardly soluble substances which organisms cannot decompose remain and accumulate. According to the present embodiment, therefore, recovery of energy is achieved more efficiently by drawing out part of digested sludge inside the anaerobic digestion tank and denaturing solid substances in the drawn digested sludge into easily soluble substances.

Embodiment 34

Another apparatus embodying the present invention and a process of treating organic wastewater with the apparatus is described.

Figure 44:
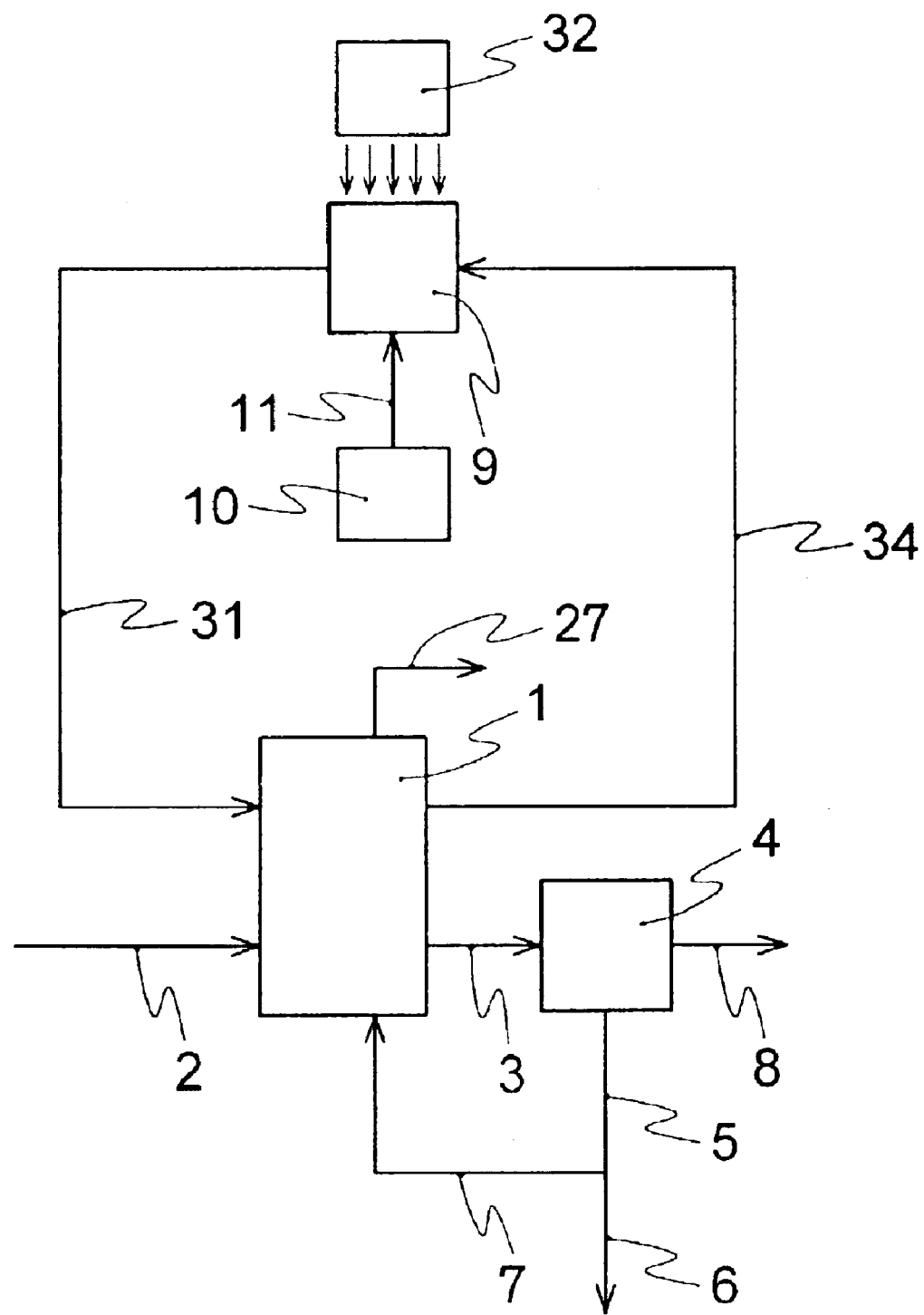
FIG. 44 is a diagram showing an apparatus embodying the present invention and a process flow of treating organic wastewater according to the present invention.

FIG. 44 is a diagram of an apparatus embodying the present invention and shows a process flow of treating organic wastewater with the apparatus. In the apparatus of the present embodiment shown in FIG. 44, components for recovering phosphorus are left out from the apparatus of Embodiment 33 shown in FIG. 43. More specifically, phosphorus recovery tank 24, solid-liquid separation tank 17 and coagulant storage tank 21 are left out and drain 31 for ozone treated sludge connects ozonization tank 9 to anaerobic digestion tank 1.

Hereinafter, workings of the apparatus according to the present embodiment are described.

As organic wastewater to be treated, organic sludge from a water treatment plant, which is a mixture of raw sludge from a primary sedimentation tank and excess sludge from an aeration tank, is introduced into anaerobic digestion tank 1 via conduit 2. The organic sludge is digested by microorganisms in anaerobic digestion tank 1 and, then, the sludge inside anaerobic digestion tank 1 is drawn out from drain 3. The sludge from drain 3 is separated into sludge solid component and sludge dissolved component in solid-liquid separation tank 4. The sludge dissolved component is discharged from drain 8 for supernatant water and the sludge solid component is discharged from drain 5 for thickened sludge.

The sludge solid component in drain 5 is discharged through conduit 6 for disposing sludge, but part of the sludge solid component is returned to anaerobic digestion tank 1 through conduit 7 for returning sludge. Meanwhile, the digester gas in anaerobic digestion tank 1 is recovered from vent 27.

In the above anaerobic digestion process, the digested sludge inside anaerobic digestion tank 1 is drawn out from conduit 34 and sent to ozonization tank 9. The digested sludge is treated with ozone by injecting ozone gas from ozone generator 10 into ozonization tank 9 via conduit 11. At the same time, the organic sludge inside ozonization tank 9 is exposed to UV radiation from UV radiator 32 so that the organic sludge is treated with ozone under UV radiation.

After being treated with ozone under UV radiation, the digested sludge is introduced into anaerobic digestion tank 1 via drain 31 and anaerobically digested by microorganisms.

The present embodiment is preferable when digested sludge contains little phosphorus and recovering energy from the sludge is a priority. By treating digested sludge with ozone under UV radiation, radicals such as OH radicals, which have stronger oxidization and decomposition effects than ozone, are generated. As a result, hardly soluble substances of solids in digested sludge, such as fibers and cell walls, can be denatured and converted into easily soluble substances which can be easily decomposed by sludge in the anaerobic digestion tank. According to the present embodiment, therefore, solubility of solids in the organic sludge is increased and yield of methane is greatly increased and, correspondingly, sludge to be disposed is greatly reduced, as compared with the case of ozone treatment without UV radiation or UV radiation without ozone treatment.

In the digested sludge of the anaerobic digestion tank, hardly soluble substances which organisms cannot decompose, remains and accumulates. According to the present embodiment, therefore, recovery of energy is achieved more efficiently by drawing out part of digested sludge inside the anaerobic digestion tank and denaturing solid substances in the drawn digested sludge into easily soluble substances.

Embodiment 35

Another apparatus embodying the present invention and a process of treating organic wastewater with the apparatus is described. In Embodiment 31, influent organic wastewater is treated with ozone under UV radiation. In Embodiment 33, digested sludge drawn from the anaerobic digestion tank is treated with ozone under UV radiation. In the present embodiment, meanwhile, digested sludge is thickened through solid-liquid separation and, then, the thickened sludge is treated with ozone under UV radiation.

Figure 45:
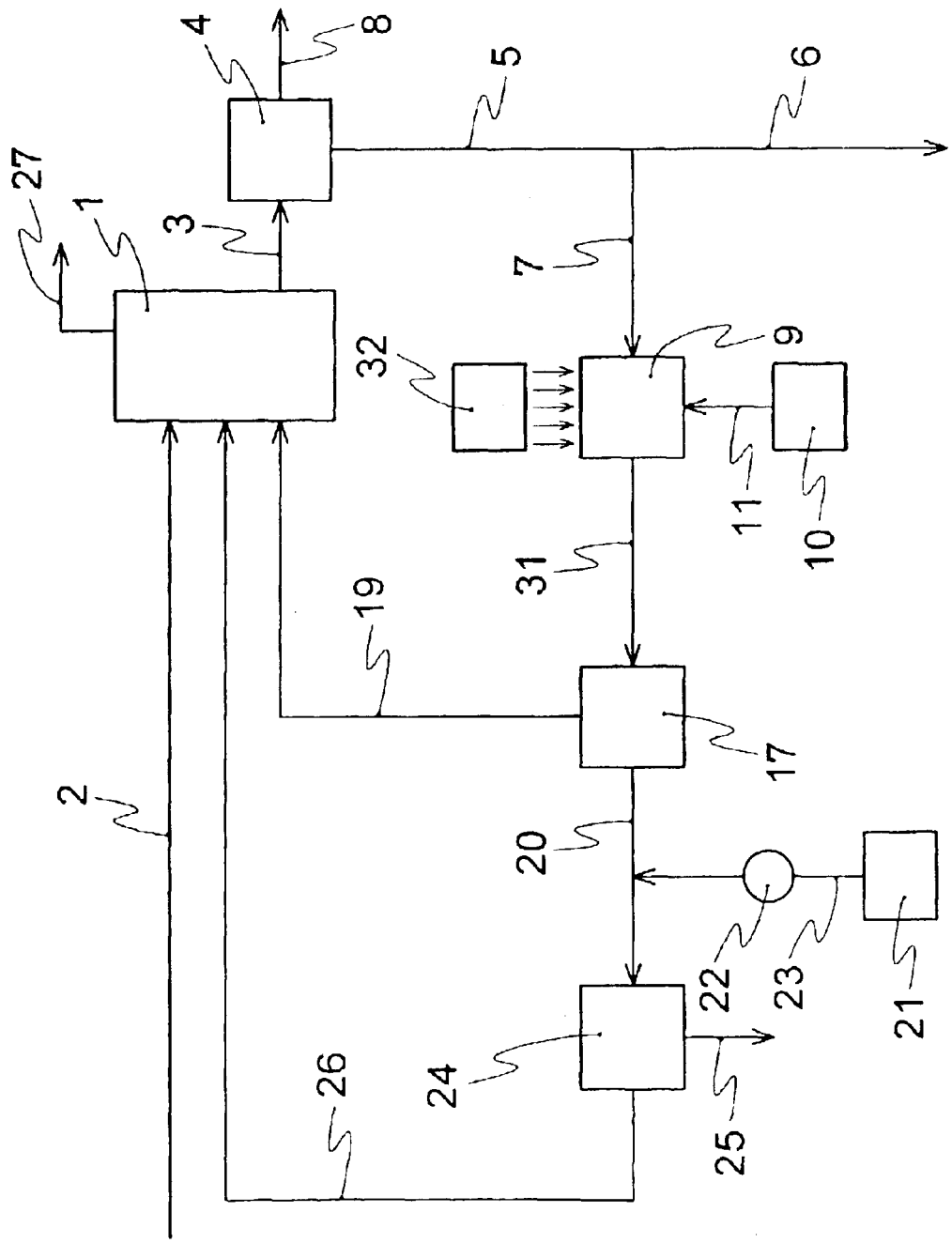
FIG. 45 is a diagram showing an apparatus embodying the present invention and a process flow of treating organic wastewater according to the present invention.

FIG. 45 is a diagram of an apparatus embodying the present invention and shows a process flow of treating organic wastewater with the apparatus. As shown in FIG. 45, organic wastewater feed conduit 2 is connected to anaerobic digestion tank 1. Anaerobic digestion tank 1 is connected to solid-liquid separation tank 4 via drain 3 for drawing digested sludge. Drain 5 for thickened sludge and drain 8 for supernatant water are connected to solid-liquid separation tank 4. Drain 5 branches into two conduits; one, i.e. conduit 6, is for disposing sludge and the other, i.e. conduit 7, is for returning sludge to ozonization tank 9. Anaerobic digestion tank 1 has vent 27 for digester gas.

The ozonization tank 9 is connected to solid-liquid separation tank 17 via drain 31 for ozone treated sludge. Solid-liquid separation tank 17 is connected to anaerobic digestion tank 1 via conduit 19 for feeding treated sludge and connected to phosphorus recovery tank 24 via drain 20 for phosphorus containing water. Phosphorus recovery tank 24 is connected to anaerobic digestion tank 1 via conduit 26 for feeding phosphorus removed water.

Moreover, ozone generator 10 is connected to ozonization tank 9 via ozone gas supply conduit 11. The top surface of ozonization tank 9 is designed to let in ultraviolet radiation from UV radiator 32 through, e.g. a transparent window.

Solid-liquid separation tank 17 is connected to phosphorus recovery tank 24 via drain 20 as described above, coagulant supply conduit 23 equipped with coagulant supply pump 22 connects coagulant storage tank 21 to drain 20.

Hereinafter, workings of the apparatus according to the present embodiment are described.

As organic wastewater to be treated, organic sludge from a water treatment plant, which is a mixture of raw sludge from a primary sedimentation tank and excess sludge from an aeration tank, is introduced into anaerobic digestion tank 1 via conduit 2. The organic sludge is digested by microorganisms in anaerobic digestion tank 1 and, then, the sludge inside anaerobic digestion tank 1 is drawn out from drain 3. The sludge from drain 3 is separated into sludge solid component and sludge dissolved component in solid-liquid separation tank 4. The sludge dissolved component is discharged from drain 8 for supernatant water and the sludge solid component is discharged from drain 5 for thickened sludge.

The sludge solid component in drain 5 is discharged through conduit 6 for disposing sludge, but part of the sludge solid component is returned to ozonization tank 9 through conduit 7 for returning sludge. Meanwhile, the digester gas in anaerobic digestion tank 1 is recovered from the vent 27.

In ozonization tank 9, the thickened sludge from conduit 7 is treated with ozone by injecting ozone gas from ozone generator 10 into ozonization tank 9 via conduit 11. At the same time, the digested sludge inside ozonization tank 9 is exposed to UV radiation from UV radiator 32 so that the digested sludge is treated with ozone under UV radiation.

After being treated with ozone under UV radiation, the thickened sludge is sent to solid-liquid separation tank 17 via drain 31 and separated into sludge solid component and sludge dissolved component. The sludge solid component is introduced into anaerobic digestion tank 1 via conduit 19 and anaerobically digested by microorganisms. Meanwhile, the sludge dissolved component rich in phosphorus is introduced into phosphorus recovery tank 24 via drain 20. At the same time, calcium carbonate solution in coagulant storage tank 21 is injected into and mixed with the phosphorus containing solution flowing through drain 20 by coagulant supply pump 22 via coagulant supply conduit 23 and phosphorus in the sludge dissolved component is precipitated as calcium phosphate. The precipitate in phosphorus recovery tank 24, i.e. calcium phosphate, is separated from the solution and drawn out from conduit 25, and the remaining solution without phosphorus is introduced into anaerobic digestion tank 1 via conduit 26 for feeding phosphorus removed water.

By treating thickened digested sludge with ozone under UV radiation in this way, radicals such as OH radicals, which have stronger oxidization and decomposition effects than ozone, are generated. As a result, hardly soluble substances of solids in thickened sludge, such as fibers and cell walls, can be denatured and converted into easily soluble substances which can be easily decomposed by sludge in the anaerobic digestion tank. According to the present embodiment, therefore, solubility of solids in the thickened sludge is increased and yield of methane is greatly increased and, correspondingly, sludge to be disposed is greatly reduced as compared with the case of ozone treatment without UV radiation or UV radiation without ozone treatment.

In addition, since decomposition of cell walls is increased owing to the activity of radicals, phosphorus in solids of digested sludge is efficiently eluted out, solidified with coagulant and recovered as reusable phosphorus. According to the present embodiment, therefore, it is possible to treat digested sludge while simultaneously recovering energy and resources, i.e. digester gas and phosphorus.

In the digested sludge of the anaerobic digestion tank, hardly soluble substances which organisms cannot decompose remains and accumulates. According to the present embodiment, therefore, recovery of energy is achieved more efficiently by thickening the digested sludge inside the anaerobic digestion tank and denaturing solid substances in the thickened digested sludge into easily soluble substances.

Embodiment 36

Another apparatus embodying the present invention and a process of treating organic wastewater with the apparatus is described.

Figure 46:
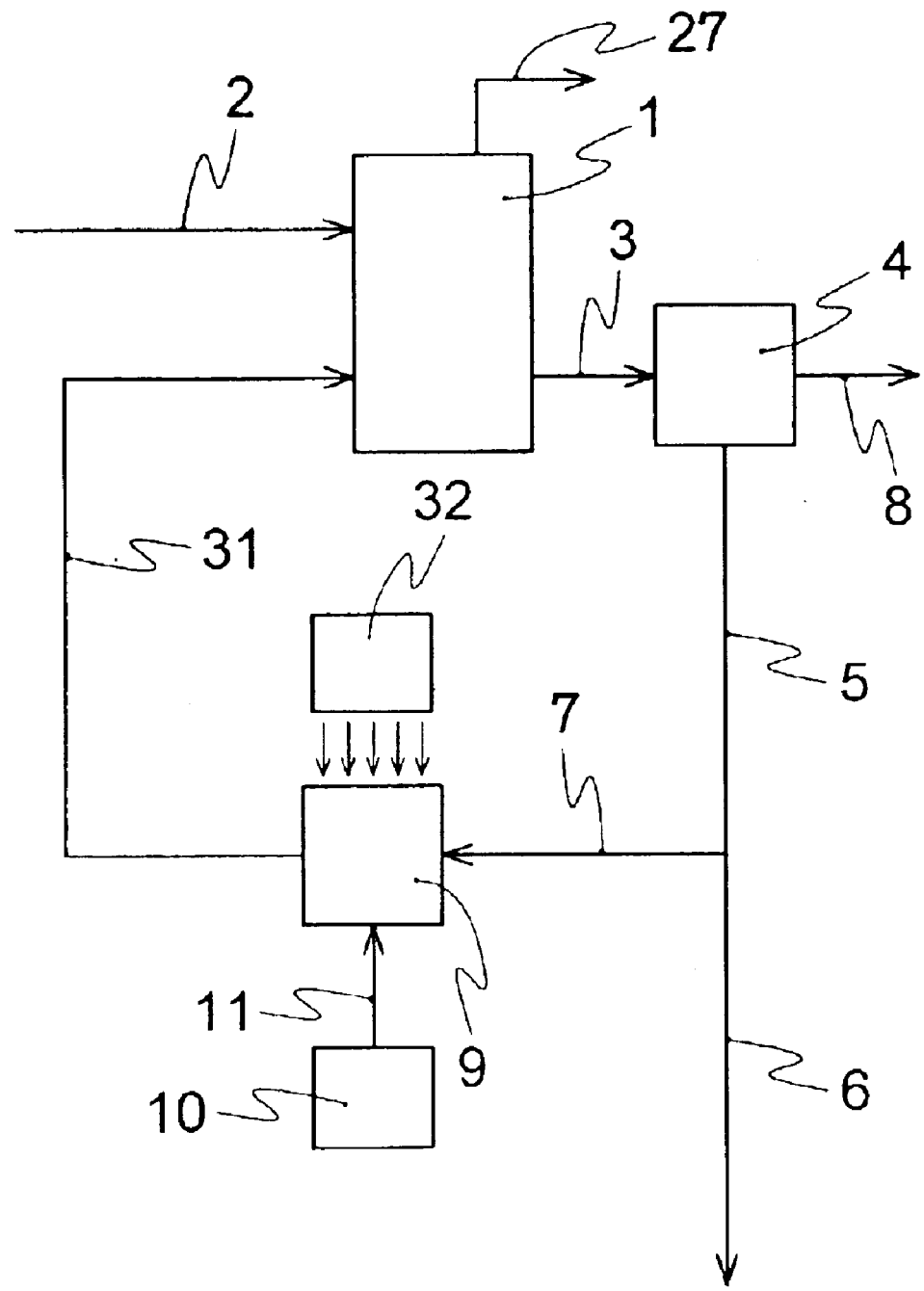
FIG. 46 is a diagram showing an apparatus embodying the present invention and a process flow of treating organic wastewater according to the present invention.

FIG. 46 is a diagram of an apparatus embodying the present invention and shows a process flow of treating organic wastewater with the apparatus. In the apparatus of the present embodiment shown in FIG. 46, components for recovering phosphorus are left out from the apparatus of Embodiment 35 shown in FIG. 45. More specifically, phosphorus recovery tank 24, solid-liquid separation tank 17 and coagulant storage tank 21 are left out and drain 31 for ozone treated sludge connects ozonization tank 9 to anaerobic digestion tank 1.

Hereinafter, workings of the apparatus according to the present embodiment are described.

As organic wastewater to be treated, organic sludge from a water treatment plant, which is a mixture of raw sludge from a primary sedimentation tank and excess sludge from an aeration tank, is introduced into anaerobic digestion tank 1 via conduit 2. The organic sludge is digested by microorganisms in anaerobic digestion tank 1 and, then, the sludge inside anaerobic digestion tank 1 is drawn out from drain 3. The sludge from drain 3 is separated into sludge solid component and sludge dissolved component in solid-liquid separation tank 4. The sludge dissolved component is discharged from drain 8 for supernatant water and the sludge solid component is discharged from drain 5 for thickened sludge.

The sludge solid component in drain 5 is discharged through conduit 6 for disposing sludge, but part of the sludge solid component is returned to ozonization tank 9 through conduit 7 for returning sludge. Meanwhile, the digester gas in anaerobic digestion tank 1 is recovered from vent 27.

In ozonization tank 9, the thickened sludge from conduit 7 is treated with ozone by injecting ozone gas from ozone generator 10 into ozonization tank 9 via conduit 11. At the same time, the thickened sludge inside ozonization tank 9 is exposed to UV radiation from UV radiator 32 so that the thickened sludge is treated with ozone under UV radiation.

After being treated with ozone under UV radiation, the thickened sludge is introduced into anaerobic digestion tank 1 via drain 31 and anaerobically digested by microorganisms.

The present embodiment is preferable when digested sludge contains little phosphorus and recovering energy from the sludge is a priority. By treating thickened digested sludge with ozone under UV radiation in this way, radicals such as OH radicals, which have stronger oxidization and decomposition effects than ozone, are generated. As a result, hardly soluble substances of solids in thickened sludge, such as fibers and cell walls, can be denatured and converted into easily soluble substances which can be easily decomposed by sludge in the anaerobic digestion tank. According to the present embodiment, therefore, solubility of solids in the thickened sludge is increased and yield of methane is greatly increased and, correspondingly, sludge to be disposed is greatly reduced as compared with the case of ozone treatment without UV radiation or UV radiation without ozone treatment.

In the digested sludge of the anaerobic digestion tank, hardly soluble substances which organisms cannot decompose remains and accumulates. According to the present embodiment, therefore, recovery of energy is achieved more efficiently by thickening the digested sludge in the anaerobic digestion tank and denaturing solid substances in the thickened digested sludge into easily soluble substances.

Embodiment 37

In the above Embodiments 1 to 36 and the following Examples 1 to 9, the organic wastewater is anaerobically digested in one anaerobic digestion tank. However, the present invention is not limited thereto. The apparatus and the process according to the present invention are also applicable to the case in which two tanks, i.e. one for producing acids and the other for producing methane, are utilized to anaerobically digest the organic wastewater and the same effects as described above such as efficient denaturation of hardly soluble substances and increase of the recovery rate of phosphorus can be obtained.

In the above Embodiments 3, 4, 9, 10, 15, 16, 21, 22, 27, 28, 33 and 34, digested sludge in the anaerobic digestion tank is drawn out and treated. In case where anaerobic digestion is conducted using two tanks; one for producing acids and the other for producing methane, a similar or higher effect can be obtained by drawing out the sludge in the former and treating.

In the above Embodiments 5, 6, 11, 12, 17, 18, 23, 24, 29, 30, 35 and 36, digested sludge in the anaerobic digestion tank is drawn out, thickened and, then, treated. In case where anaerobic digestion is conducted using two tanks; one for producing acids and the other for producing methane, a similar or higher effect can be obtained by thickening the sludge in the former and treating the thickened sludge.

Embodiment 38

In the above Embodiments, 1, 3, 5, 7, 9, 11, 13, 15, 17, 19, 21, 23, 25, 27, 29, 31, 33 and 35, calcium carbonate is used as a coagulant to recover eluted phosphorus. However, the coagulant used in the present invention is not limited thereto. For example, a compound containing calcium such as calcium hydrogen carbonate is also applicable to attain the same effects as those of the above Embodiments. Moreover, common coagulant such as polychlorinated aluminum (PAC) is also applicable. Furthermore, another technique for solidifying phosphorus such as crystallization may replace the technique of the above Embodiments in which eluted phosphorus is recovered using coagulant.

Although the phosphorus removed water is returned to the anaerobic digestion tank 1 via conduit 26 in the above Embodiments, the phosphorus removed water may be separately treated without returning to anaerobic digestion tank 1.

Embodiment 39

In the above Embodiments and the following Examples, a mixture comprising raw sludge and excess sludge both from a water treatment plant is treated as organic wastewater. However, the organic wastewater to be treated is not limited thereto and the same or greater effects as those of the above Embodiments can be obtained even when treating sludge, waste and effluent rich in organic substances, such as raw sludge from a water treatment plant, excess sludge from the same, raw garbage, food waste, animal waste, human waste, industrial waste and mixture thereof.

Although sodium hydroxide is used for alkali treatment in the above Embodiments 1 to 36 and the following Examples, another alkali agent such as potassium hydroxide may be applicable.

Embodiment 40

In the above Embodiments 31 to 36, UV ray is radiated through the top surface of the ozonization tank where the transparent windows is provided. However, transparent window(s) may be provided at the side or bottom of the ozonization tank to introduce UV radiation. Moreover, the effect equal to or higher than that of the above Embodiments can also be obtained even when the UV radiator is arranged inside the ozonization tank.

EXAMPLES 1 TO 3 AND COMPARATIVE EXAMPLES 1 TO 3

Excess sludge was drawn out from a wastewater treatment plant, treated with ozone and, then, treated with alkali. In the ozone treatment, the ozone injection rate was 0.05 g-$O_3$/g-SS. In the alkali treatment, sodium hydroxide was added and pH 12 was maintained for 10 minutes. 1.0 L of digested sludge having a TS concentration of about 25,000 mg/L was drawn out from an aerobic digestion tank and, then, introduced into a culture flask having an effective volume of 3.0 L. 1.0 L of the above treated sludge (sludge treated with ozone and alkali) of which the pH was adjusted to approximately neutral and the TS concentration was adjusted to about 25,000 mg/L was introduced into the culture flask. 2.0 L of the sludge mixture having a TS concentration of 25,000 mg/L obtained in this way was anaerobically digested at 50° C. (Example 1).

For comparison, the above excess sludge was treated with ozone (without alkali treatment) or treated with alkali (without ozone treatment). The ozone injection rate was 0.05 g-$O_3$/g-SS in this ozone treatment and pH 12 was maintained for 10 minutes in this alkali treatment. 1.0 L of an aerobically digested sludge having a TS concentration of about 25,000 mg/L was introduced into a culture flask having an effective volume of 3.0 L. 1.0 L of the above treated sludge (sludge treated with ozone or sludge treated with alkali) of which the pH was approximately neutral and the TS concentration was about 25,000 mg/L was introduced into the culture flask. 2.0 L of a sludge mixture having a TS concentration of 25,000 mg/L obtained in this way was anaerobically digested at 50° C. (Comparative Example 1 or 2).

In order to estimate the influence of the pH in the alkali treatment upon anaerobic digestion, the above excess sludge treated with ozone and alkali was mixed with the anaerobically digested sludge without adjusting pH and, then, anaerobically digested at 50° C. (Example 2).

In order to estimate the influence of sodium ion in the alkali treatment, the above excess sludge treated with ozone and alkali was centrifuged and the sediment was suspended in pure water twice to rinse the sludge. Then, the pH of this sludge after rinsing was adjusted to approximately neutral, this sludge was mixed with the anaerobically digested sludge and, then, anaerobically digested at 50° C. (Example 3).

For reference, 2.0 L of digested sludge having a TS concentration of about 25,000 mg/L without any treatment was anaerobically digested at 50° C. (Comparative Example 3).

TABLE 1

| Ex. No. | Treatment |
|---|---|
| Ex. 1 | ozone (O) + alkali (A) + pH neutralization (N) |
| Ex. 2 | ozone (O) + alkali (A) |
| Ex. 3 | ozone (O) + alkali (A) + rinse (R) + pH neutralization (N) |
| Com. Ex. 1 | ozone (O) |
| Com. Ex. 2 | alkali (A) |
| Com. Ex. 3 | none |

Figure 1:
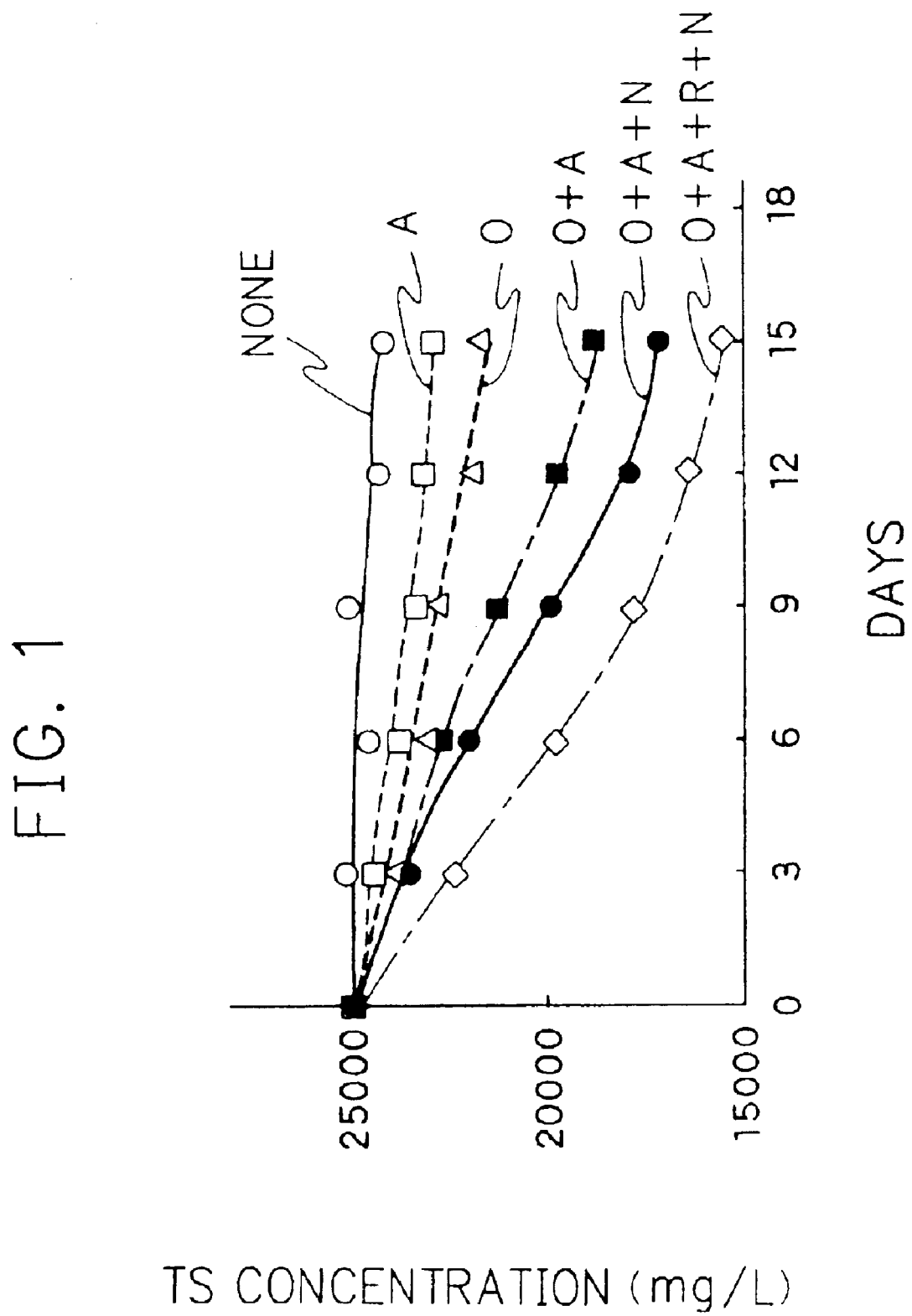
FIG. 1 is a graph showing the effect of time on TS concentration in a process of treating organic wastewater according to the present invention.
Figure 2:
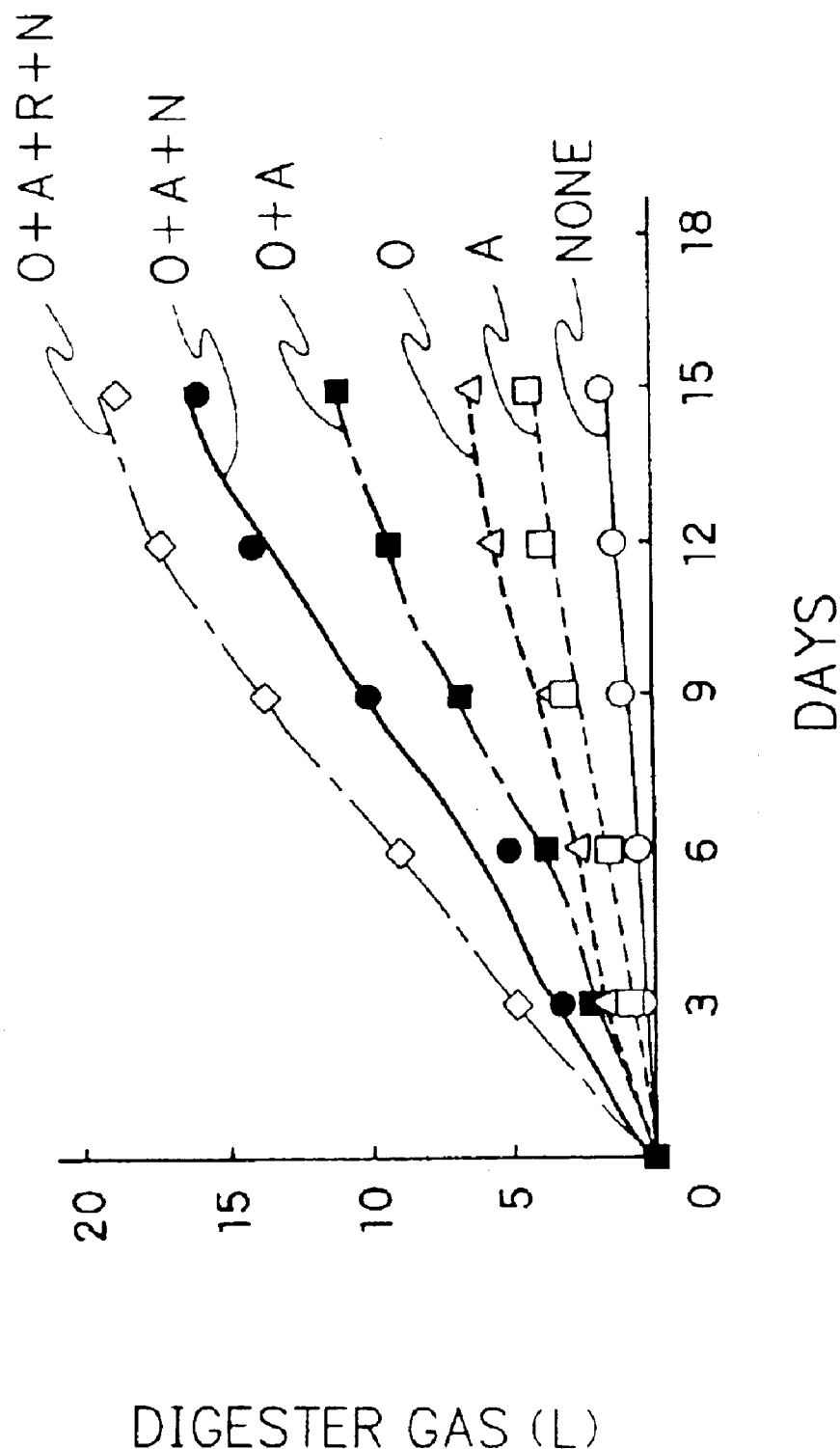
FIG. 2 is a graph showing the effect of time on total amount of digester gas in a process of treating organic wastewater according to the present invention.

For Examples 1 to 3 and Comparative Examples 1 to 3, variation in TS concentration was shown in FIG. 1 and amount of digester gas produced (in total) was shown in FIG. 2. In FIGS. 1 and 2, white circles represent Comparative Example 1 in which sludge was not treated, white squares represent Comparative Example 2 in which sludge was treated with alkali alone, white triangles represent Comparative Example 3 in which sludge was treated with ozone alone, black circles represent Example 1 in which the pH of the sludge treated with ozone and alkali was adjusted to neutral, black squares represent Example 2 in which the pH of the sludge treated with ozone and alkali was not adjusted to neutral, and white diamonds represent Example 3 in which sludge treated with ozone and alkali was rinsed, respectively.

As shown in FIG. 1, decomposition of solids in the sludge advances and the TS concentration decreases over time. In case where the sludge is treated with ozone or alkali, decomposition of solids is promoted and the TS concentration decreases rapidly. In case where the sludge is denatured through the combined process of ozone and alkali treatments according to the present invention, decomposition of solids is further promoted and TS concentration is significantly decreased.

For example, although decrease in TS concentration for 15 days is about 3,000 mg/L for the sludge treated with ozone alone and about 1,500 mg/L for the sludge treated with alkali alone, that for the sludge treated with ozone and alkali in combination is about 8,000 mg/L which is greater than the sum of the above decreases of ozone treatment alone and alkali treatment alone.

Although combination of ozone and alkali treatments is effective, decrease in TS concentration was reduced by half when the pH of the sludge was not adjusted. Since a higher pH due to the alkali treatment may inhibit the activity of the microorganisms for anaerobic digestion, the pH of the sludge treated with ozone and alkali is preferably adjusted to approximately neutral to ensure the above decrease in TS concentration, i.e. effect of decomposing the sludge.

In case where the sludge is treated with ozone and alkali in combination and, then, rinsed, decrease in TS concentration was further enhanced as compared with the case without rinsing. Since the sodium ion added in the alkali treatment may inhibit the activity of the microorganisms for anaerobic digestion, sodium ions are preferably removed, for example, by rinsing the sludge or the solution is diluted, to ensure the above decrease in TS concentration, i.e. effect of decomposing the sludge.

As shown in FIG. 2, the amount of produced digester gas from the sludge treated with ozone and alkali in combination is greater than that from ozone treated sludge or alkali treated sludge. Since the amount of produced digester gas from the sludge treated with ozone and alkali in combination is greater than the sum of the yields from ozone treated sludge and alkali treated sludge, the combination of ozone and alkali treatments has found to be synergistic. Furthermore, the amount of produced digester gas from the rinsed sludge increased as compared with the case without rinsing, indicating the remarkable effect of removing sodium ion.

Figure 3:
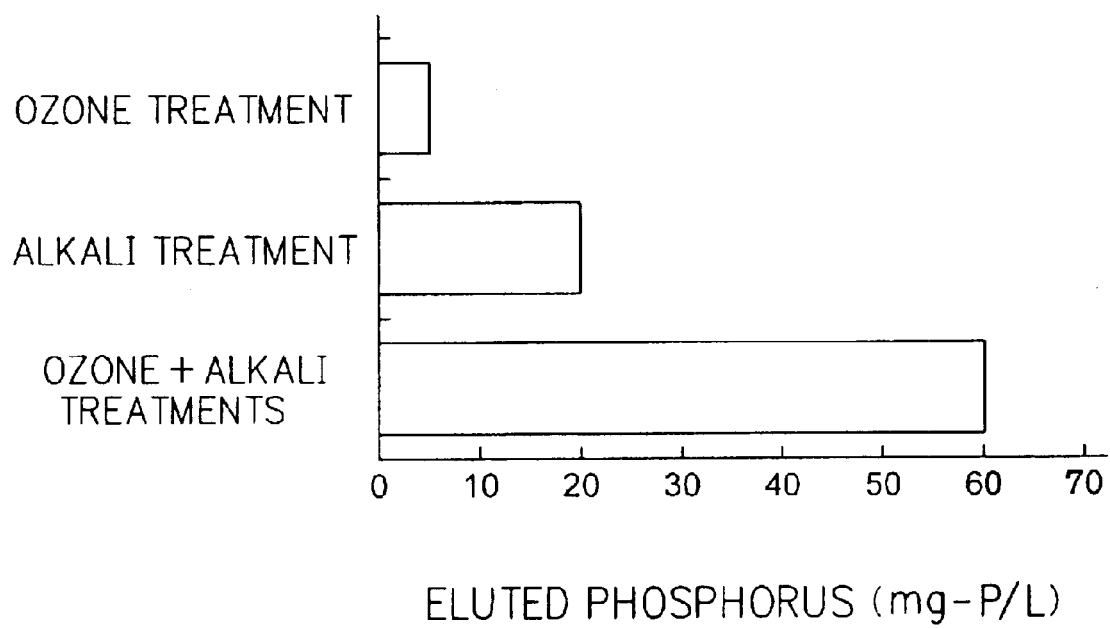
FIG. 3 is a graph showing concentration of eluted phosphorus in a process of treating organic wastewater according to the present invention.

Immediately after the treatments with ozone and alkali in combination, treatment with ozone alone or treatment with alkali alone, sludge was centrifuged and concentration of phosphorus in the supernatant water was measured. The results are shown in FIG. 3. In case where sludge is treated with ozone and alkali in combination, the concentration of eluted phosphorus is higher than that of ozone treatment alone or alkali treatment alone. Since the concentration of eluted phosphorus in the sludge treated with ozone and alkali in combination is greater than the sum of those in ozone treated sludge and alkali treated sludge, the combination of ozone and alkali treatments has found to be synergistic. Eluted phosphorus in the supernatant water was precipitated as calcium phosphate by adding and mixing calcium carbonate solution and recovered as solid phosphorus by centrifugal separation. The amount of recovered phosphorus was greatest when the sludge was treated with ozone and alkali in combination.

Further, sodium ions were removed from the above phosphorus removed water by ion exchange and, then, the resultant solution was mixed with the rinsed sludge treated with ozone and alkali in combination. Thereafter, the pH and TS concentration of the mixture were adjusted and the mixture was anaerobically digested according to the above Examples. As a result, the same effect was obtained in decrease in TS concentration and the amount of produced digester gas was increased as compared with Example in which sludge was rinsed.

As described above, the process of the present invention, in which ozone treatment and succeeding alkali treatment are combined, is highly effective in decreasing the solids in the sludge, i.e. decomposition, promoting production of digester gas and eluting and recovering phosphorus in the sludge. In anaerobic digestion of thus treated sludge, the above effects can be increased by adjusting the pH of the sludge to neutral and/or removing sodium ions of alkali treatment from the sludge. Furthermore, it is found that organic substances eluted along with phosphorus can be converted into methane and generation of digester gas can be increased by anaerobically digesting after removing sodium ions added in alkali treatment and/or adjusting the pH of the phosphorus removed water.

In the above ozone treatment process, the ozone injection rate is preferably 0.01 to 0.10 g-$O_3$/g-SS and more preferably 0.03 to 0.07 g-$O_3$/g-SS. With an ozone injection rate smaller than 0.01 g-$O_3$/g-SS, organic sludge is not sufficiently denatured and digestion thereof, that is, yield of methane hardly increases. In addition thereto, phosphorus in the sludge is hardly eluted out with such a small ozone injection rate. Although a larger ozone injection rate enhances both yield of methane and elution of phosphorus, this enhancement becomes slower with an ozone injection rate larger than 0.10 g-$O_3$/g-SS. Therefore, an ozone injection rate larger than 0.10 g-$O_3$/g-SS is considered uneconomical.

In the above alkali treatment process, the sludge is preferably treated with alkali for 5 to 30 minutes maintaining pH within a range of 9 to 13. With a pH smaller than 9, organic sludge is not sufficiently denatured and digestion thereof, that is, yield of methane hardly increases. In addition thereto, phosphorus in the sludge is hardly eluted out with a pH smaller than 9. Although a higher alkalinity enhances both yield of methane and elution of phosphorus, this enhancement becomes slower with a pH higher than 13. Therefore, a pH higher than 13 is considered uneconomical. Similarly, in case where the treatment time is shorter than 5 minutes, organic sludge is not sufficiently denatured and digestion thereof, that is, yield of methane hardly increases. In addition thereto, phosphorus in the sludge is hardly eluted out with a treatment time shorter than 5 minutes. Although a longer alkali treatment time enhances both yield of methane and elution of phosphorus, this enhancement becomes slower with a treatment time longer than 30 minutes. Therefore, an alkali treatment time longer than 30 minutes is considered uneconomical.

EXAMPLE 4 AND COMPARATIVE EXAMPLES 4 TO 6

Excess sludge was drawn out from a wastewater treatment plant and hydrogen peroxide was added to the excess sludge. Immediately thereafter, the sludge was treated with ozone. The amount of hydrogen peroxide was 20 to 100 mg per 1 liter of the sludge and the ozone injection rate was 0.05 g-$O_3$/g-SS. 1.0 L of anaerobically digested sludge having a TS concentration of about 25,000 mg/L was introduced into a culture flask having an effective volume of 3.0 L. 1.0 L of the above treated sludge (sludge treated with ozone in the presence of hydrogen peroxide) of which the TS concentration was adjusted to about 25,000 mg/L was introduced into the culture flask. 2.0 L of the sludge mixture having a TS concentration of 25,000 mg/L obtained in this way anaerobically digested at 50° C. (Example 4).

For comparison, hydrogen peroxide was added to the above excess sludge (without ozone treatment) or the above excess sludge was treated with ozone (without adding hydrogen peroxide). The amount of hydrogen peroxide was 20 to 100 mg per 1 liter of the sludge and the ozone injection rate was 0.05 g-$O_3$/g-SS. 1.0 L of anaerobically digested sludge having a TS concentration of about 25,000 mg/L was introduced into a culture flask having an effective volume of 3.0 L. 1.0 L of the above treated sludge (sludge with hydrogen peroxide or sludge treated with ozone) of which the pH was adjusted to approximately neutral and the TS concentration was about 25,000 mg/L was introduced into the culture flask. 2.0 L of the sludge mixture having a TS concentration of 25,000 mg/L obtained in this way was anaerobically digested at 50° C. (Comparative Example 4 or 5).

For reference, 2.0 L of digested sludge having TS concentration of about 25,000 mg/L without any treatment was anaerobically digested at 50° C. (Comparative Example 6).

TABLE 2

| Ex. No. | Treatment |
|---|---|
| Ex. 4 | hydrogen peroxide (H) + ozone (O) |
| Com. Ex. 4 | hydrogen peroxide (H) |
| Com. Ex. 5 | ozone (A) |
| Com. Ex. 6 | NONE |

Figure 4:
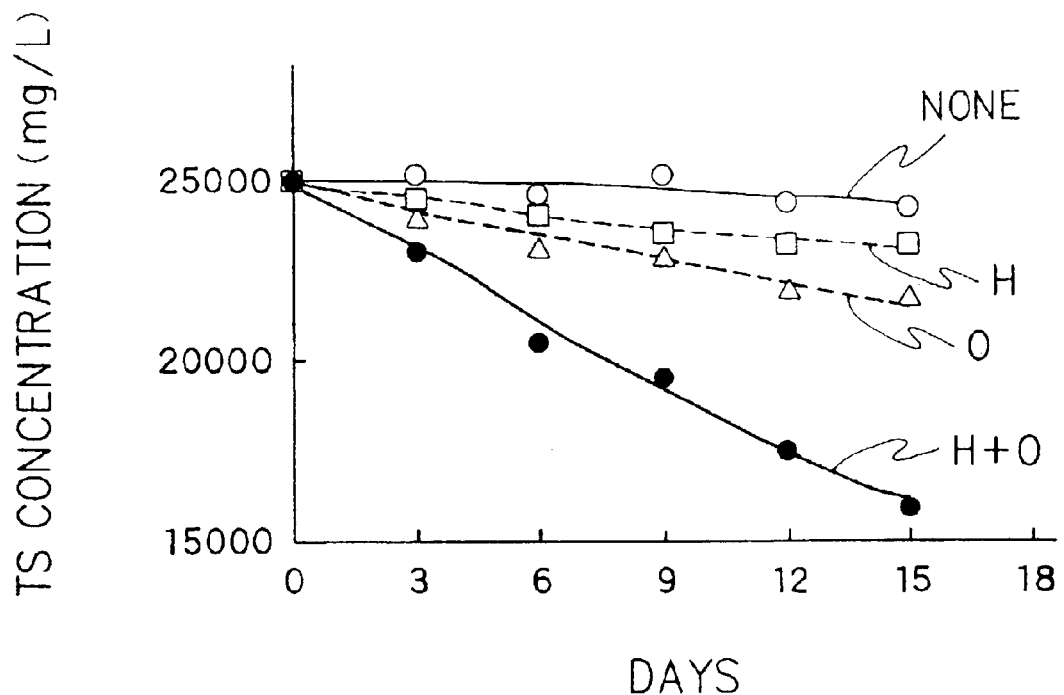
FIG. 4 is a graph showing the effect of time on TS concentration in a process of treating organic wastewater according to the present invention.
Figure 5:
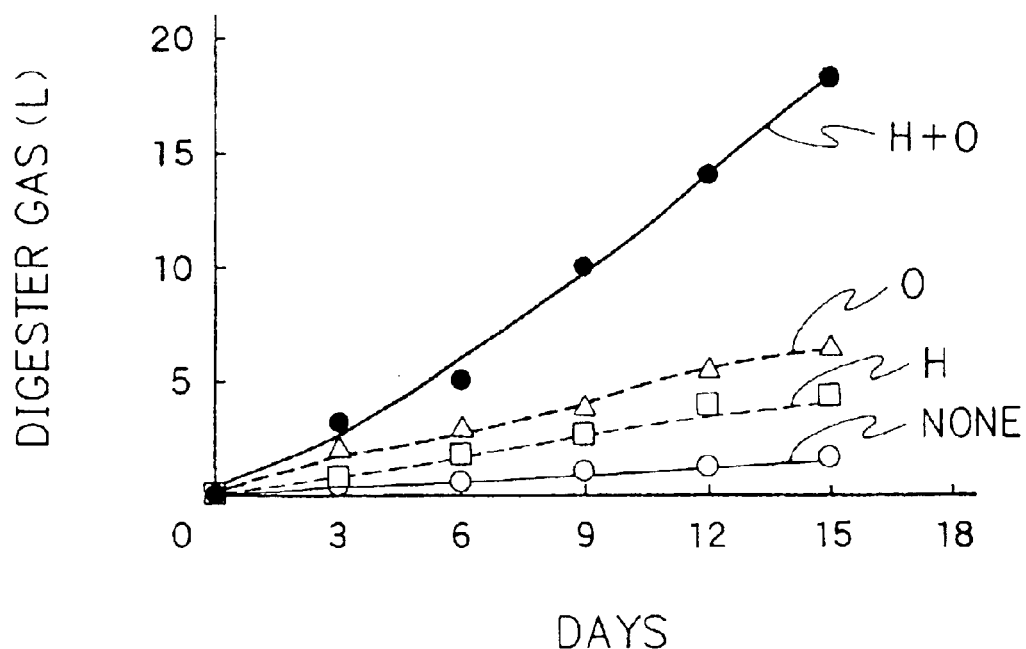
FIG. 5 is a graph showing the effect of time on total amount of digester gas in a process of treating organic wastewater according to the present invention.

For Example 4 and Comparative Examples 4 to 6, variation in TS concentration over time was shown in FIG. 4 and amount of digester gas produced (in total) was shown in FIG. 5. In FIGS. 4 and 5, white circles represent Comparative Example 6 in which sludge was not treated by any treatment, white squares represent Comparative Example 4 in which only hydrogen peroxide was added, white triangles represent Comparative Example 5 in which sludge was treated with ozone alone, and black circles represent Example 4 in which sludge was treated with ozone in the presence of hydrogen peroxide.

As shown in FIG. 4, solids in the sludge are dissolved over time and the TS concentration decreases. By adding hydrogen peroxide to the sludge or treating the sludge with ozone, dissolution of solids is promoted and the TS concentration decreases rapidly. By treating the sludge with ozone immediately after adding hydrogen peroxide, i.e. by the process of the present invention where the sludge is treated with ozone in the presence of hydrogen peroxide, dissolution of solids is further promoted and TS concentration is significantly decreased.

For example, the decrease in TS concentration in 15 days was approximately 1,300 mg/L for sludge to which only hydrogen peroxide was added and approximately 3,000 mg/L for sludge treated only with ozone. However, for sludge treated with ozone immediately after adding hydrogen peroxide, the decrease was approximately 9,000 mg/L and the TS concentration was decreased significantly in comparison to the sum of when adding hydrogen peroxide and ozone treatment were conducted independently.

As shown in FIG. 5, the amount produced of digester gas from the sludge to which hydrogen peroxide is added and treated with ozone was greater than that from sludge with only hydrogen peroxide or sludge treated with ozone only. As the yield of digester gas from the sludge to which hydrogen peroxide is added and treated with ozone was greater than the sum of those from sludge with only hydrogen peroxide and sludge treated with ozone only, the combination of hydrogen peroxide and ozone treatment was found to be synergistic.

Figure 6:
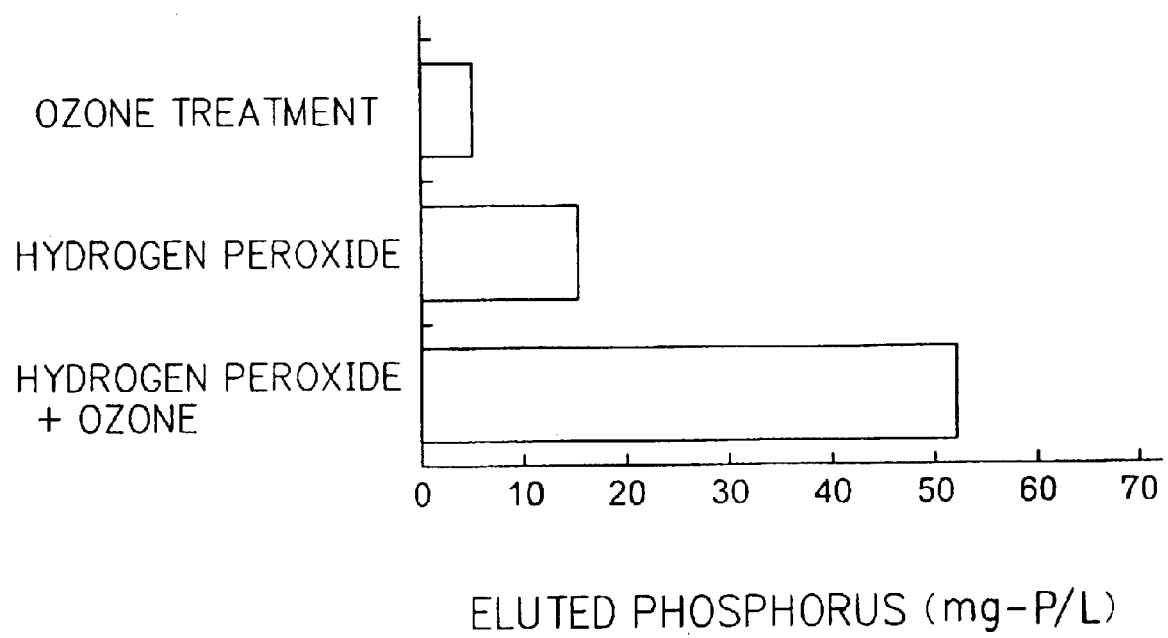
FIG. 6 is a graph showing concentration of eluted phosphorus in a process of treating organic wastewater according to the present invention.

Immediately after adding hydrogen peroxide, treatment with ozone or treatment with ozone in the presence hydrogen peroxide, the sludge was centrifuged and concentration of phosphorus in the supernatant water was measured. The results are shown in FIG. 6. In the case that sludge is treated with ozone in the presence of hydrogen peroxide, the concentration of eluted phosphorus was greater than that of ozone treatment alone or adding only hydrogen peroxide and, further, greater than the sum of these. Also, the eluted phosphorus in the supernatant water was precipitated as calcium phosphate by adding calcium carbonate solution and then mixing and recovered as solid phosphorus through centrifugal separation. The amount of recovered phosphorus was greatest when the sludge was treated with ozone in the presence of hydrogen peroxide.

As described above, the process of the present invention, in which sludge is treated with ozone in the presence of hydrogen peroxide, is highly effective in decreasing, i.e. dissolving, the solids in the sludge, promoting production of digester gas and eluting and recovering the phosphorus in the sludge.

The hydrogen peroxide is added so that the concentration preferably becomes 20 to 100 mg/L. In the case that the concentration of hydrogen peroxide is lower than 20 mg/L, organic sludge is not sufficiently denatured and digestion thereof, that is, yield of methane hardly increases. In addition thereto, phosphorus in the sludge is hardly eluted out with such low hydrogen peroxide concentration. Although a higher hydrogen peroxide concentration enhances both yield of methane and elution of phosphorus, this enhancement becomes slower with a concentration higher than 100 mg/L. Therefore, concentration of hydrogen peroxide higher than 100 mg/L is considered uneconomical.

The ozone injection rate may preferably be 0.01 to 0.10 g-$O_3$/g-SS and more preferably 0.03 to 0.07 g-$O_3$/g-SS. With an ozone injection rate smaller than 0.01 g-$O_3$/g-SS, organic sludge is not sufficiently denatured and digestion thereof, that is, yield of methane hardly increases. In addition thereto, phosphorus in the sludge is hardly eluted out with such a small ozone injection rate. Although a larger ozone injection rate enhances both yield of methane and elution of phosphorus, this enhancement becomes slower with an ozone injection rate larger than 0.10 g-$O_3$/g-SS. Therefore, an ozone injection rate larger than 0.10 g-$O_3$/g-SS is considered uneconomical.

EXAMPLE 5 AND COMPARATIVE EXAMPLES 7 TO 9

Excess sludge was taken out from a wastewater treatment plant and treated with ozone while introducing UV radiation. The sludge was exposed to an UV lamp having a wavelength of 260 nm and an output of 100 W for 30 minutes. For ozone treatment, the ozone injection rate was 0.05 g-$O_3$/g-SS. 1.0 L of anaerobically digested sludge having a TS concentration of approximately 25,000 mg/L was introduced into a culture flask having effective volume of 3.0 L. The above treated sludge (sludge treated with ozone under UV radiation) was prepared to have a TS concentration of approximately 25,000 mg/L and, then, 1.0 L of the sludge was introduced into the culture flask so that 2.0 L of a mixture having a TS concentration of approximately 25,000 mg/L was obtained. The mixture of sludge thus obtained was anaerobically digested at 50° C. (Example 5).

For comparison, the above excess sludge was exposed to UV radiation only (without ozone treatment) or treated with ozone only (without UV radiation). Irradiation was conducted by exposing the sludge to an UV lamp having a wavelength of 260 nm and an output of 100 W for 30 minutes. In the ozone treatment, ozone was injected at a rate of 0.05 g-$O_3$/g-SS. 1.0 L of anaerobically digested sludge having a TS concentration of approximately 25,000 mg/L was introduced into a culture flask having effective volume of 3.0 L. The above treated sludge (sludge exposed to UV radiation only or sludge treated with ozone only) was prepared to have a TS concentration of approximately 25,000 mg/L and, then, 1.0 L of the sludge was introduced into the culture flask so that 2.0 L of a mixture having a TS concentration of 25,000 mg/L was obtained. The mixture of sludge thus obtained was anaerobically digested at 50° C. (Comparative Example 7 or 8).

For reference, 2.0 L of digested sludge having a TS concentration of approximately 25,000 mg/L without any treatment was anaerobically digested at 50° C. (Comparative Example 9).

TABLE 3

| Ex. No. | Treatment |
| --- | --- |
| Ex. 5 | UV radiation (UV) + ozone (O) |
| Com. Ex. 7 | UV radiation (UV) |
| Com. Ex. 8 | ozone (O) |
| Com. Ex. 9 | None |

Figure 7:
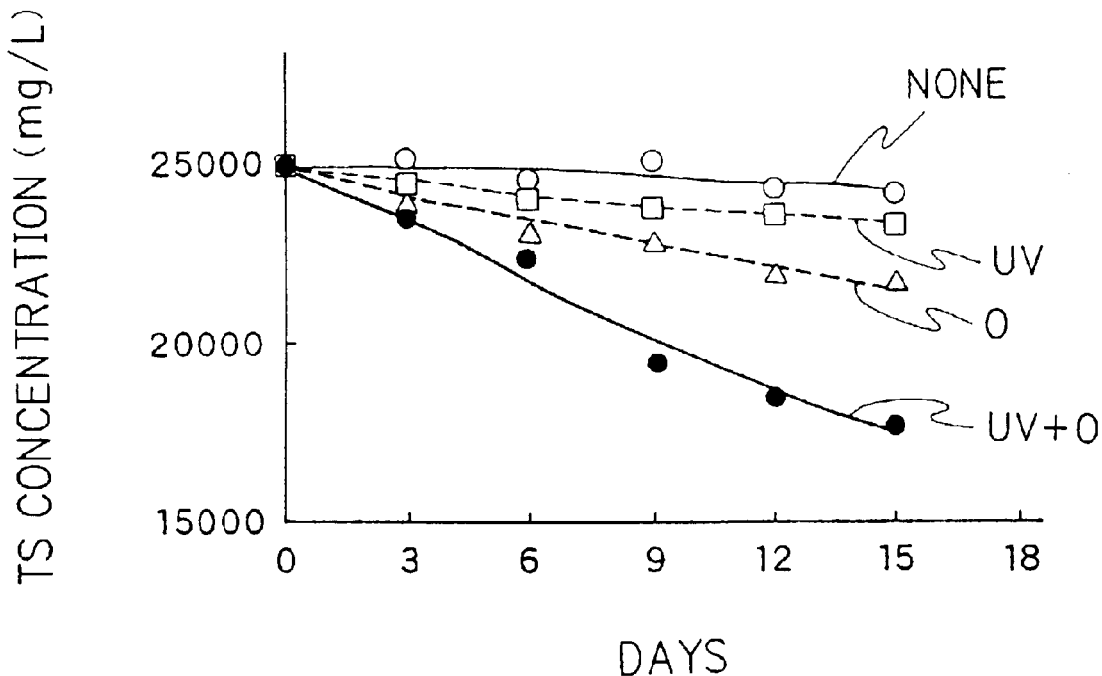
FIG. 7 is a graph showing the effect of time on TS concentration in a process of treating organic wastewater according to the present invention.
Figure 8:
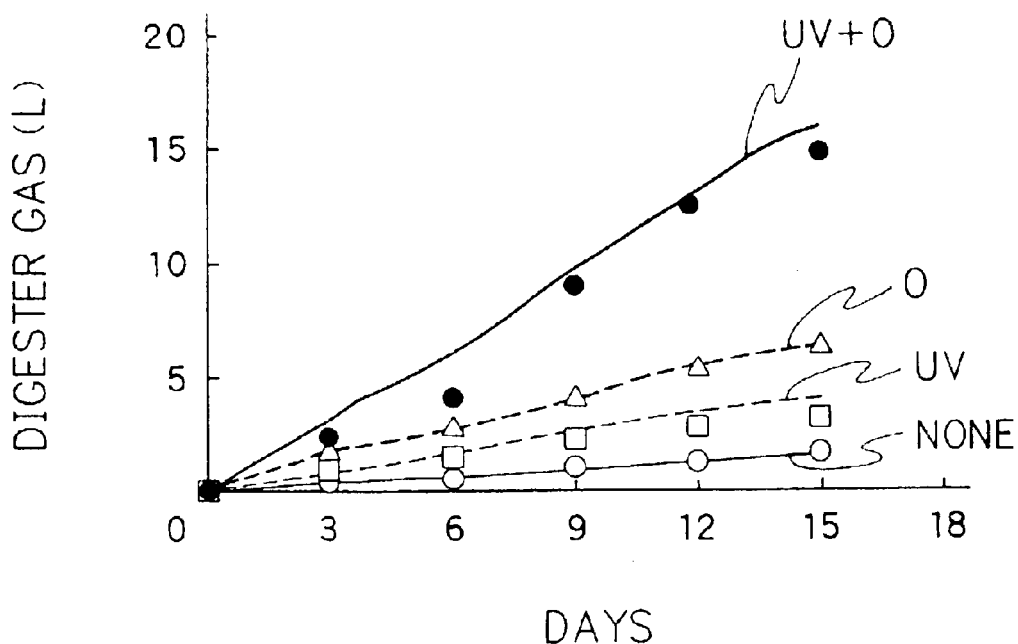
FIG. 8 is a graph showing the effect of time on total amount of digester gas in a process of treating organic wastewater according to the present invention.

For Example 5 and Comparative Examples 7 to 9, variation in TS concentration over time was shown in FIG. 7 and the amount of digester gas produced (in total) was shown in FIG. 8. In FIGS. 7 and 8, white circles represent Comparative Example 9 in which sludge was not treated with any treatment, white squares represent Comparative Example 7 in which sludge was exposed to UV radiation only, white triangles represent Comparative Example 8 in which sludge was treated with ozone alone, and black circles represent Example 5 in which sludge was treated with ozone under UV radiation.

As shown in FIG. 7, solids in the sludge are dissolved over time and the TS concentration decreases. By exposing the sludge to UV radiation or treating the sludge with ozone, dissolution of solids is promoted and TS concentration decreases rapidly. By the process of denaturing the sludge according to the present invention in which sludge is treated with ozone under UV radiation, dissolution of solids is further promoted so that the TS concentration is decreased significantly.

For example, the decrease in TS concentration in 15 days was approximately 800 mg/L for the sludge exposed to UV radiation and approximately 3,000 mg/L for the sludge treated with ozone. However, for the sludge treated with ozone under UV radiation, the decrease was approximately 7,000 mg/L and the TS concentration was decreased significantly in comparison to the sum of when exposure to UV radiation and ozone treatment were conducted independently.

As shown in FIG. 8, the amount produced of digester gas from the sludge treated with ozone under UV radiation is greater than that from sludge exposed to UV radiation only or sludge treated with ozone only and, furthermore, greater than the sum of these.

Figure 9:
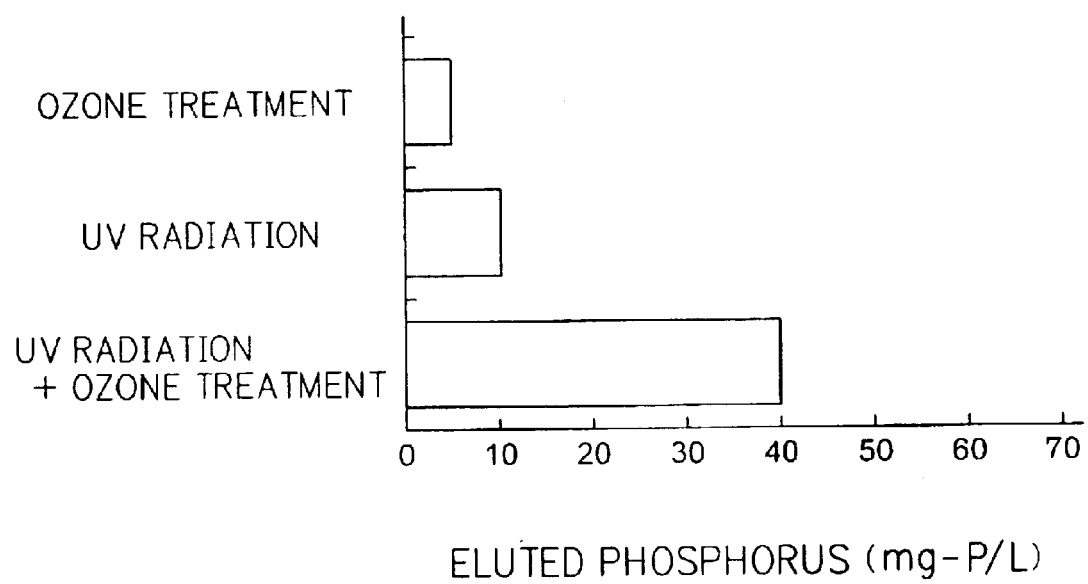
FIG. 9 is a graph showing concentration of eluted phosphorus in a process of treating organic wastewater according to the present invention.

Immediately after exposure to UV radiation, treatment with ozone or treatment with ozone under UV radiation, the sludge was centrifuged and concentration of phosphorus in the supernatant water was measured. The results are shown in FIG. 9. In the case that sludge was treated with ozone under UV radiation, eluted phosphorus was greater than that of ozone treatment only or exposure to UV radiation only and, further, greater than the sum of these. Eluted phosphorus in the supernatant water was precipitated as calcium phosphate by adding calcium carbonate solution and mixing and recovered as solid phosphorus through centrifugal separation. The amount of recovered phosphorus was greatest when the sludge was treated with ozone under UV radiation.

As described above, the process of the present invention, in which sludge is treated with ozone under UV radiation, is highly effective in decreasing, i.e. dissolving, the solids in the sludge, promoting production of digester gas and eluting and recovering phosphorus in the sludge.

In the above process, the wavelength of the UV radiation is preferably 180 to 300 nm, output of the UV radiation is preferably 5.0 to 200 W and exposure to the UV radiation is preferably 5 to 30 minutes. Although shorter wavelength enhances both yield of methane and elution of phosphorus, this enhancement becomes slower with the wavelength shorter than 180 nm. Therefore, wavelength shorter than 180 nm is considered uneconomical. In the case that the wavelength of the UV radiation is longer than 300 nm, organic sludge is not sufficiently denatured and digestion thereof, that is, yield of methane hardly increases. In addition thereto, phosphorus in the sludge is hardly eluted out with UV radiation of such long wavelength. In the case that the output of the UV radiation is smaller than 5.0 W, organic sludge is not sufficiently denatured and digestion thereof, that is, yield of methane hardly increases. In addition thereto, phosphorus in the sludge is hardly eluted out with UV radiation of such small output. Although a larger output enhances both yield of methane and elution of phosphorus, this enhancement becomes slower with an output larger than 200 W. Therefore, an output larger than 200 W is considered uneconomical. In the case that exposure to UV radiation is shorter than 5 minutes, organic sludge is not sufficiently denatured and digestion thereof, that is, yield of methane hardly increases. In addition thereto, phosphorus in the sludge is hardly eluted out with such short exposure. Although longer exposure enhances both yield of methane and elution of phosphorus, this enhancement becomes slower with exposure longer than 30 minutes. Therefore, exposure longer than 30 minutes is considered uneconomical.

In the ozone treatment, the ozone injection rate is preferably 0.01 to 0.10 g-$O_3$/g-SS and more preferably 0.03 to 0.07 g-$O_3$/g-SS. When the ozone injection rate is smaller than 0.01 g-$O_3$/g-SS, organic sludge is not sufficiently denatured and digestion thereof, that is, yield of methane hardly increases. In addition thereto, phosphorus in the sludge is hardly eluted out with such a small ozone injection rate. Although a larger ozone injection rate enhances both yield of methane and elution of phosphorus, this enhancement becomes slower with an ozone injection rate larger than 0.10 g-$O_3$/g-SS. Therefore, an ozone injection rate larger than 0.10 g-$O_3$/g-SS is considered uneconomical.

EXAMPLES 6 TO 9 AND COMPARATIVE EXAMPLE 10

In Examples 1 to 5, sludge was not added to the culture flask and digested sludge was not drawn out from the culture flask. In an actual sludge treatment plant, however, introduction of sludge and extraction of digested sludge are carried out continuously or periodically. Accordingly, continuous digestion in which excess sludge from a wastewater treatment plant is continuously introduced was conducted.

Five culture flasks each having effective volume of 5.0 were charged with 4.0 L of digested sludge having a TS concentration of approximately 25,000 mg/L and the sludge was anaerobically digested at 50° C. Meanwhile, excess sludge was treated according to the present invention, prepared to have TS concentration of approximately 25,000 mg/L and, then, 0.8 L, 0.4 L, 0.26 L, 0.2 L and 0.13 L of the treated excess sludge were introduced into the respective culture flasks once a day. Immediately before the introduction of treated excess sludge, the same amount of sludge was extracted from the respective culture flask so that the amount of sludge inside the flask remained the same. With the above introduction and extraction, retention time of the sludge in each culture flask was 5, 10, 15, 20 and 30 days, respectively.

As for the treatment to excess sludge, ozone and successive alkali treatments (Example 6), ozone treatment under presence of hydrogen peroxide (Example 7) and ozone treatment under UV radiation (Example 8) were carried out according to the conditions of Examples 1, 4 and 5, respectively. With respect to the ozone and successive alkali treatments, the excess sludge was rinsed (Example 9) according to the conditions of Example 3. For reference, untreated excess sludge was used (Comparative Example 10) instead of the treated excess sludge.

TABLE 4

| Ex. No. | Treatment |
| --- | --- |
| Ex. 6 | ozone (O) + alkali (A) + pH neutralization (N) |
| Ex. 7 | hydrogen peroxide (H) + ozone (O) |
| Ex. 8 | UV radiation (UV) + ozone (O) |
| Ex. 9 | ozone (O) + alkali (A) + rinse (R) + pH neutralization (N) |
| Com. Ex. 10 | None |

For Examples 6 to 9 and Comparative Example 10, anaerobic digestion was carried out for 3 months while introducing and extracting the above prescribed amount of sludge. The TS reduction rate, i.e. percentage of solids being digested, was calculated from the total TS amount in the introduced sludge and the remaining TS amount which did not dissolve.

Figure 10:
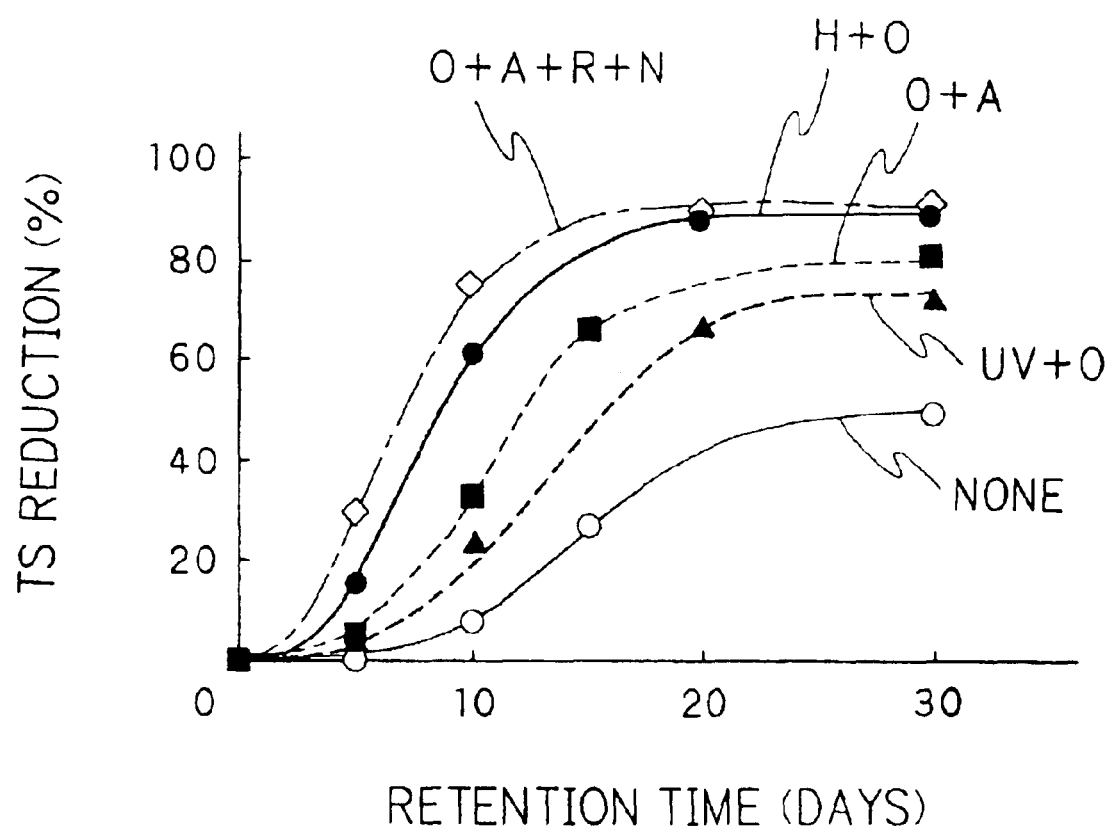
FIG. 10 is a graph showing the effect of sludge retention time on TS reduction in a process of treating organic wastewater according to the present invention.

The effect of retention time on the TS reduction rate is shown in FIG. 10. In FIG. 10, white circles represent Comparative Example 10 in which the excess sludge was not treated, black squares represent Example 6 in which excess sludge was treated with ozone and alkali, black circles represent Example 7 in which excess sludge was treated with ozone under presence of hydrogen peroxide, black triangles represent Example 8 in which excess sludge was treated with ozone under UV radiation, and white diamonds represent Example 9 in which excess sludge treated with ozone and alkali was rinsed.

As shown in FIG. 10, in the case that excess sludge was not treated, solids in the sludge were hardly dissolved during the retention time of 10 days and the TS reduction rate finally reached 50% at a retention time of 30 days. In the case that sludge was denatured with the process of the present invention, that is, sludge was treated with ozone and alkali, treated with ozone in the presence of hydrogen peroxide or treated with ozone under UV radiation, TS reduction was observed within a retention time of 10 days. In Examples 6 to 9, a TS reduction rate of 20 to 60% was obtained at a retention time of 10 days and a high TS reduction rate of approximately 80% was obtained at a retention time of 30 days. Moreover, in the case that sludge was rinsed, the TS reduction decreased faster and a higher TS reduction rate was obtained at the retention time of 30 days, when compared to the combination of ozone and alkali treatment.

From the Examples 6 to 9 and Comparative Example 10, by the process of the present invention, digestion of excess sludge is carried out in shorter time and the TS reduction rate is enhanced.

INDUSTRIAL APPLICABILITY

According to the present invention in which at least one of influent organic wastewater, digested sludge drawn from an aerobic digestion tank and digested sludge thickened through solid-liquid separation or a mixture of these sludge is treated with ozone and successively with alkali, solubilization of sludge and transformation into methane are greatly enhanced. As a result, sludge to be disposed is also greatly reduced.

By adjusting the pH of the sludge and/or reducing inhibitors of anaerobic digestion after alkali treatment, deactivation of the microorganisms in the anaerobic digestion tank hardly occurs and the above advantageous effects of solubilization of solids, transformation into methane and reduction in disposed sludge are constantly ensured.

According to the present invention in which at least one of influent organic wastewater, digested sludge drawn from an aerobic digestion tank and digested sludge thickened through solid-liquid separation or a mixture of these sludge is treated with ozone and successively with alkali, the amount of eluted phosphorus is greatly increased, in addition to solubilization of sludge and transformation into methane. The eluted phosphorus is recovered as reusable phosphorus by coagulation and membrane separation and energy and phosphorus are simultaneously recovered from the sludge.

By adjusting the pH of the sludge and/or reducing inhibitors of anaerobic digestion after alkali treatment, deactivation of the microorganisms in the anaerobic digestion tank hardly occurs and the above advantageous effects of eluting out phosphorus and simultaneously recovering energy and phosphorus are constantly ensured.

According to the present invention in which at least one of influent organic wastewater, digested sludge drawn from an aerobic digestion tank and digested sludge thickened through solid-liquid separation or a mixture of these sludge is treated with ozone in the presence of hydrogen peroxide, solubilization of sludge and transformation into methane are greatly enhanced. As a result, sludge to be disposed is also greatly reduced.

According to the present invention in which at least one of influent organic wastewater, digested sludge drawn from an aerobic digestion tank and digested sludge thickened through solid-liquid separation or a mixture of these sludge is treated with ozone in the presence of hydrogen peroxide, the amount of eluted phosphorus is greatly increased in addition to solubilization of sludge and transformation into methane. The eluted phosphorus is recovered as reusable phosphorus by coagulation and membrane separation and energy and phosphorus are simultaneously recovered from the sludge.

According to the present invention in which at least one of influent organic wastewater, digested sludge drawn from an aerobic digestion tank and digested sludge thickened through solid-liquid separation or a mixture of these sludge is treated with ozone under UV radiation, solubilization of sludge and transformation into methane are greatly enhanced. As a result, sludge to be disposed is also greatly reduced.

According to the present invention in which at least one of influent organic wastewater, digested sludge drawn from an aerobic digestion tank and digested sludge thickened through solid-liquid separation or a mixture of these sludge is treated with ozone under UV radiation, the amount of eluted phosphorus is greatly increased in addition to solubilization of sludge and transformation into methane. The eluted phosphorus is recovered as reusable phosphorus by coagulation and membrane separation and energy and phosphorus are simultaneously recovered from the sludge.

What is claimed is:

1. A process for treating organic wastewater by anaerobic digestion, comprising:
   treating organic wastewater with ozone and successively with alkali; and
   introducing the organic wastewater after treating with alkali into an anaerobic digestion tank.

2. The process for treating organic wastewater according to claim 1, including adjusting pH of the organic waste water to neutral after treating with alkali and before introduction into the anaerobic digestion tank.

3. The process for treating organic wastewater according to claim 1, including reducing concentration of an inhibitor of anaerobic digestion in the organic waste water after treating with alkali and before introduction into the anaerobic digestion tank.

4. The process for treating organic wastewater according to claim 1, further comprising separating the organic wastewater after treating with alkali into a solid part and a solution part, introducing the solid part into the anaerobic digestion tank and removing phosphorus from the solution part.

5. The process for treating organic wastewater according to claim 4, including adjusting pH of the solid part and/or the solution part to neutral after recovering phosphorus, and introducing the solid part and/or solution part into the anaerobic digestion tank.

6. The process for treating organic wastewater according to claim 4, including reducing concentration of an inhibitor of anaerobic digestion in the solid part and/or the solution part after recovering phosphorus, and introducing the solid part and/or solution part into the anaerobic digestion tank.

7. A process for treating organic wastewater by anaerobic digestion, comprising:
   treating organic wastewater with ozone in the presence of hydrogen peroxide;
   separating the organic wastewater, after treating with ozone, into a solid part and a solution part;
   introducing the solid part into an anaerobic digestion tank; and
   removing phosphorus from the solution part.

8. An apparatus for treating organic wastewater comprising:
   means for treating organic wastewater with ozone;
   means for treating the organic wastewater with alkali after treatment with ozone; and
   an anaerobic digestion tank for anaerobically digesting the organic wastewater after treatment with alkali.

9. The apparatus for treating organic wastewater according to claim 8, including a pH regulator for adjusting pH of the organic wastewater to neutral, the pH regulator being provided between the means for treating with alkali and the anaerobic digestion tank.

10. The apparatus for treating organic wastewater according to claim 8, including means for reducing concentration of an inhibitor of anaerobic digestion in the organic wastewater provided between the means for alkali treatment and the anaerobic digestion tank.

11. The apparatus for treating organic wastewater according to claim 8, including means for separating the organic wastewater into a solid part and a solution part, the means for separating being provided between the means for alkali treatment and the anaerobic digestion tank, and a means for recovering phosphorus from the solution part.

12. The apparatus for treating organic wastewater according to claim 11, including a pH regulator for adjusting pH of the solid part and/or the solution part to neutral after recovering phosphorus, the pH regulator being provided between the means for separating the organic wastewater and the anaerobic digestion tank and/or between the means for recovering phosphorus and the anaerobic digestion tank.

13. The apparatus for treating organic wastewater according to claim 11, including means for reducing concentration of an inhibitor of anaerobic digestion in the solid part and/or the solution part after recovering phosphorus, the means for reducing being provided between the means for separating the organic wastewater and the anaerobic digestion tank and/or between the means for recovering phosphorus and the anaerobic digestion tank.

14. An apparatus for treating organic wastewater comprising:
- means for treating organic wastewater with ozone in the presence of hydrogen peroxide;
- an anaerobic digestion tank for anaerobically digesting the organic wastewater after treating with ozone;
- means for separating the organic wastewater into a solid part and a solution part, the means for separating being provided between the means for treating with ozone and the anaerobic digestion tank; and
- means for recovering phosphorus from the solution part.

* * * * *